US011911112B2

(12) United States Patent
Crawford et al.

(10) Patent No.: US 11,911,112 B2
(45) Date of Patent: Feb. 27, 2024

(54) ROBOTIC NAVIGATIONAL SYSTEM

(71) Applicant: GLOBUS MEDICAL, INC., Audubon, PA (US)

(72) Inventors: Neil R. Crawford, Chandler, AZ (US); Norbert Johnson, North Andover, MA (US); Thomas Calloway, Pelham, NH (US); Dana Wisniewski, Audubon, PA (US)

(73) Assignee: Globus Medical, Inc., Audubon, PA (US)

( * ) Notice: Subject to any disclaimer, the term of this patent is extended or adjusted under 35 U.S.C. 154(b) by 35 days.

(21) Appl. No.: 17/080,901

(22) Filed: Oct. 27, 2020

(65) Prior Publication Data

US 2022/0125520 A1 Apr. 28, 2022

(51) Int. Cl.
| | |
|---|---|
| A61B 34/20 | (2016.01) |
| A61B 34/30 | (2016.01) |
| A61B 90/00 | (2016.01) |
| B25J 15/00 | (2006.01) |

(52) U.S. Cl.
CPC .............. *A61B 34/20* (2016.02); *A61B 34/30* (2016.02); *A61B 90/37* (2016.02); *B25J 15/0019* (2013.01); *A61B 2034/2057* (2016.02); *A61B 2034/2068* (2016.02); *A61B 2090/3762* (2016.02)

(58) Field of Classification Search
CPC ......... A61B 34/20; A61B 34/30; A61B 90/39; A61B 2034/2057; A61B 90/37; A61B 2090/3762; A61B 2034/2068; B25J 5/0019
See application file for complete search history.

(56) References Cited

U.S. PATENT DOCUMENTS

| | | | |
|---|---|---|---|
| 4,150,293 | A | 4/1979 | Franke |
| 5,246,010 | A | 9/1993 | Gazzara et al. |
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 5,987,960 | A | 11/1999 | Messner et al. |
| 6,012,216 | A | 1/2000 | Esteves et al. |

(Continued)

FOREIGN PATENT DOCUMENTS

| | | |
|---|---|---|
| JP | 2015531624 A | 11/2015 |
| JP | 2018509949 A | 4/2018 |

(Continued)

OTHER PUBLICATIONS

US 8,231,638 B2, 07/2012, Swarup et al. (withdrawn)

*Primary Examiner* — Chao Sheng

(57) ABSTRACT

Devices, systems, and methods for a robot-assisted surgery. Navigable instrumentation, which are capable of being navigated by a surgeon using the surgical robot system, and navigation software allow for the navigated placement of interbody fusion devices or other surgical devices.

15 Claims, 49 Drawing Sheets

(56) References Cited

U.S. PATENT DOCUMENTS

| | | |
|---|---|---|
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |

(56) References Cited

U.S. PATENT DOCUMENTS

| | | |
|---|---|---|
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Akin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |

(56) References Cited

U.S. PATENT DOCUMENTS

| | | |
|---|---|---|
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0100325 A1* | 5/2007 | Jutras .................. A61B 90/39 606/1 |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |

(56) References Cited

U.S. PATENT DOCUMENTS

| | | |
|---|---|---|
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2009/0324009 A1 * | 12/2009 | Schulz .................. G06T 7/73 382/103 |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0254922 A1 * | 10/2011 | Schaerer ............... A61B 90/39 348/46 |
| 2011/0276058 A1 | 11/2011 | Choi et al. |
| 2011/0282189 A1 | 11/2011 | Graumann |
| 2011/0286098 A1 * | 11/2011 | Hauri .................... A61B 34/20 359/543 |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0135732 A1 * | 5/2013 | Shafer .................... G02B 5/134 359/545 |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |

(56) References Cited

U.S. PATENT DOCUMENTS

| | | |
|---|---|---|
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0086941 A1 * | 3/2017 | Marti ............... A61B 34/20 |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0258535 A1 * | 9/2017 | Crawford ......... A61B 17/7074 |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2020/0315737 A1 | 10/2020 | Crawford et al. |

FOREIGN PATENT DOCUMENTS

| | | |
|---|---|---|
| JP | 2020096833 A | 6/2020 |
| WO | 2005087125 A2 | 9/2005 |

* cited by examiner

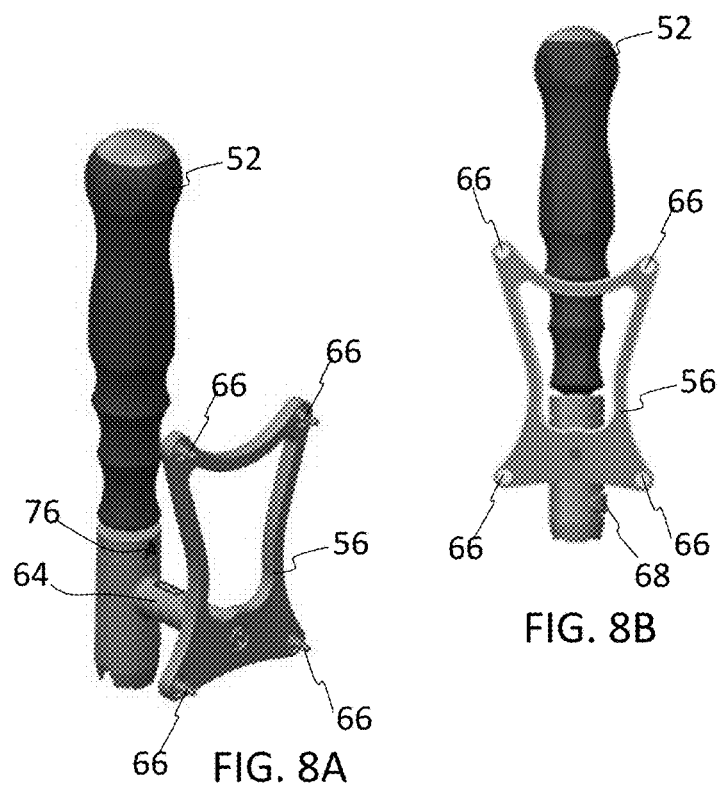
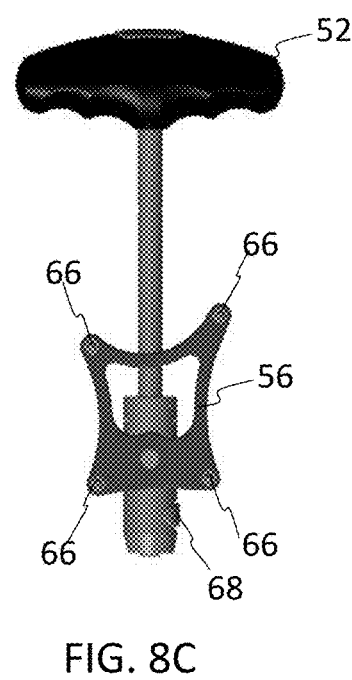
FIG. 8A  FIG. 8B  FIG. 8C
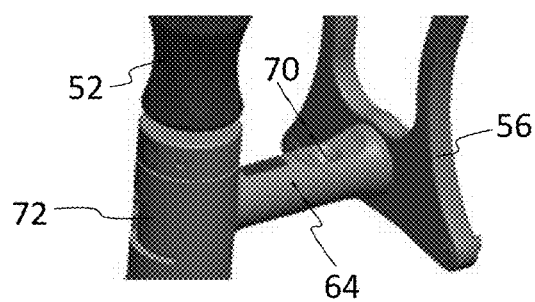
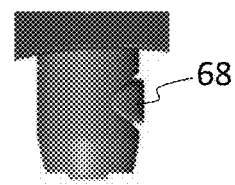
FIG. 8D  FIG. 8E

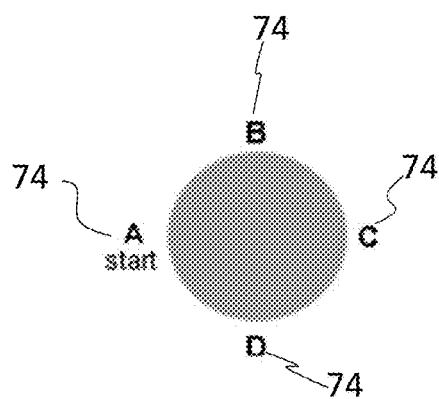
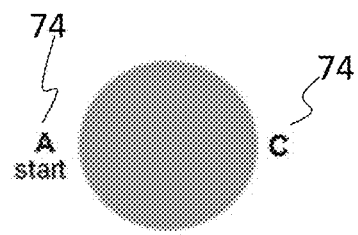
FIG. 10A    FIG. 10B
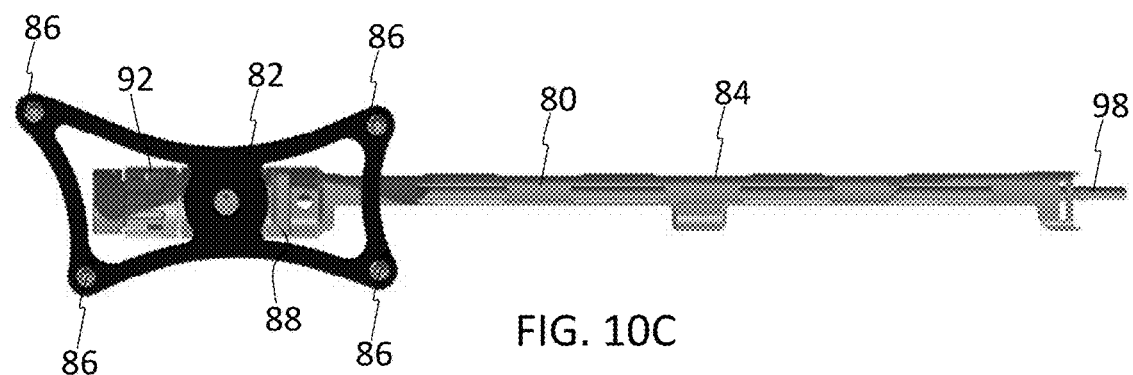
FIG. 10C
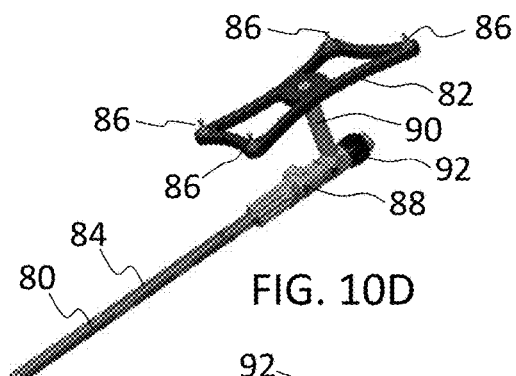
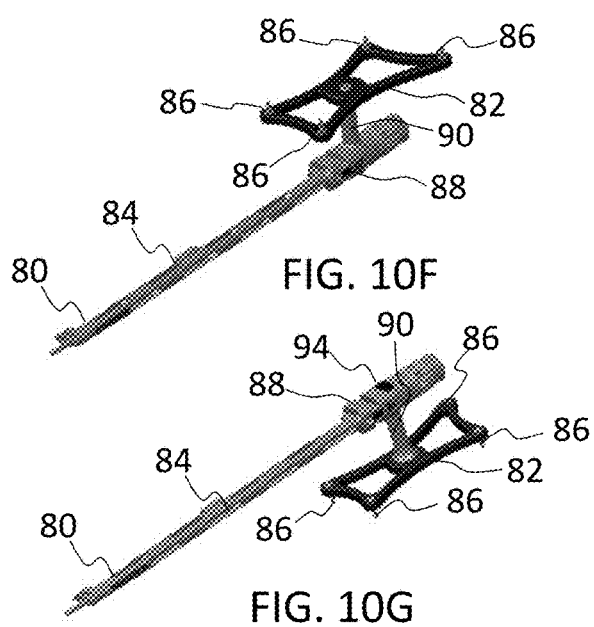
FIG. 10D    FIG. 10F
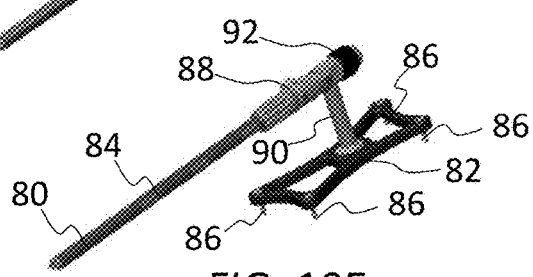
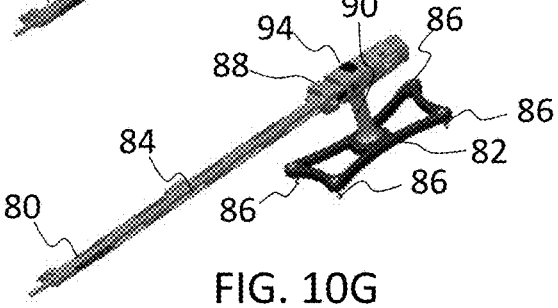
FIG. 10E    FIG. 10G

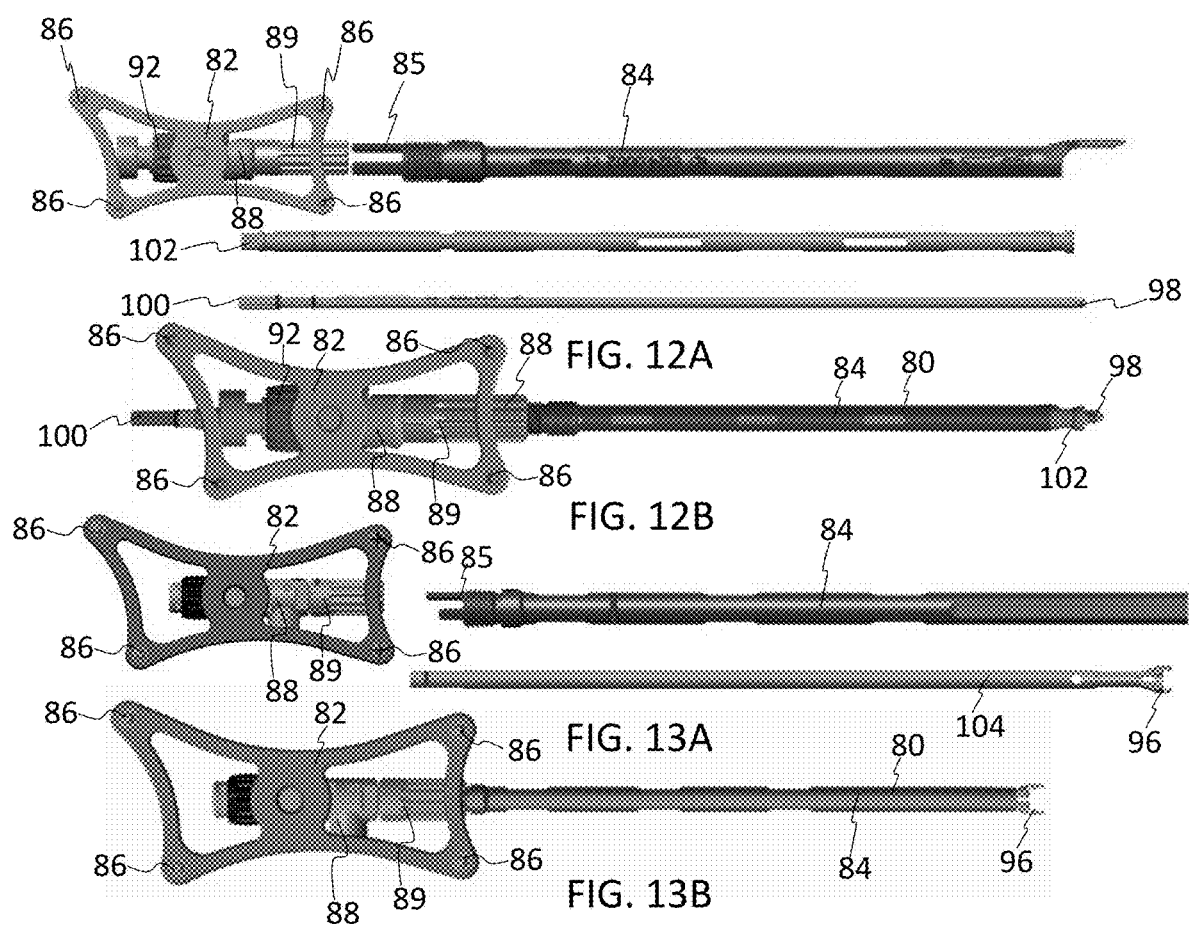

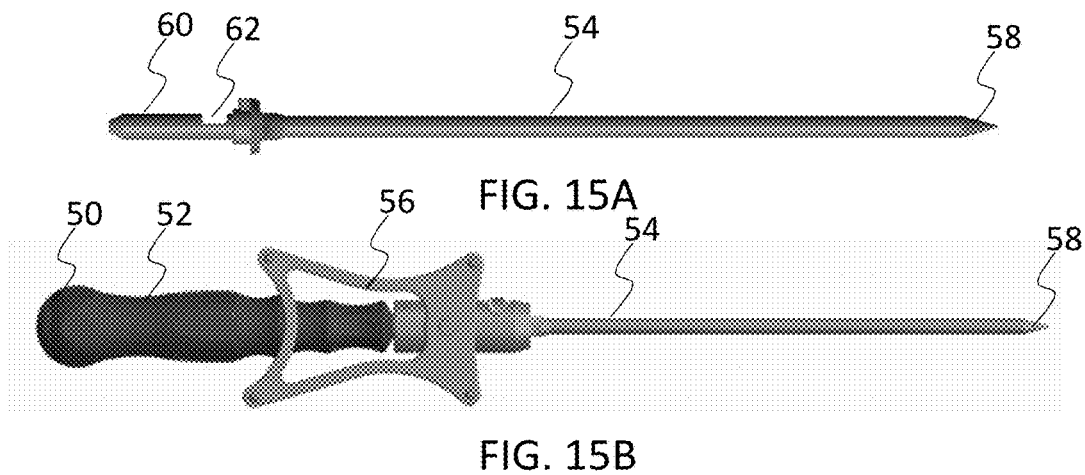
FIG. 15A
FIG. 15B
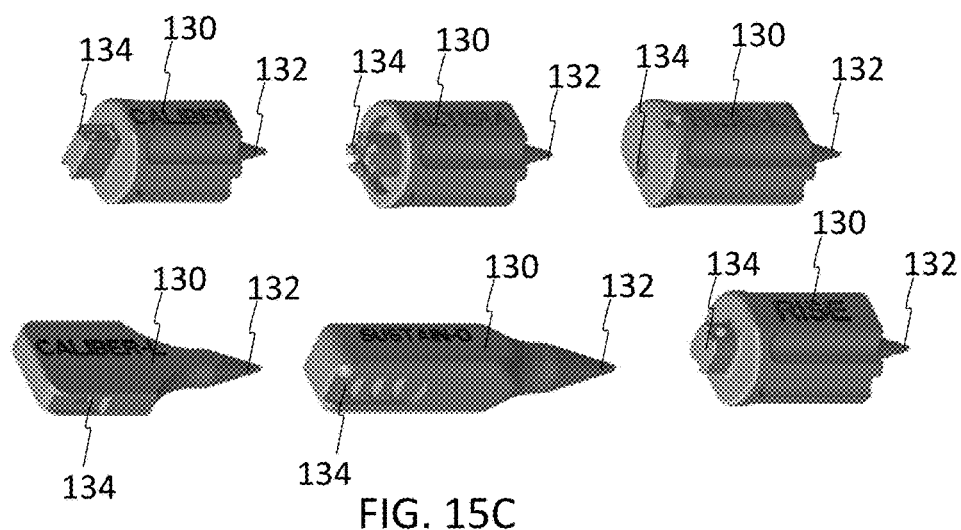
FIG. 15C
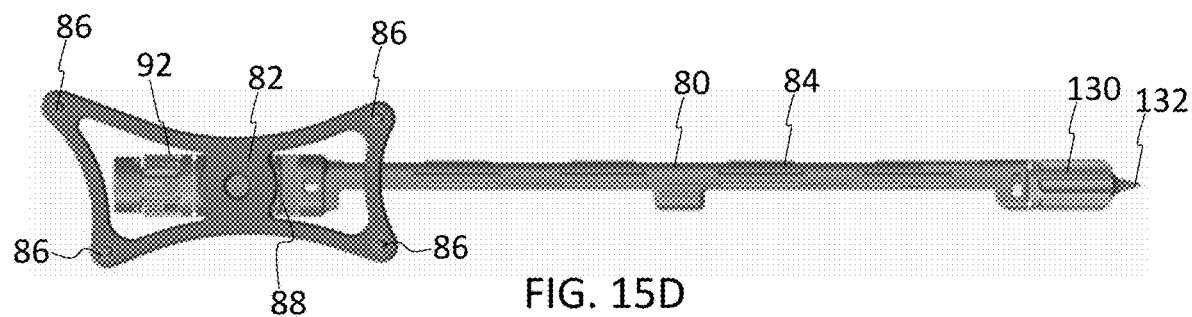
FIG. 15D

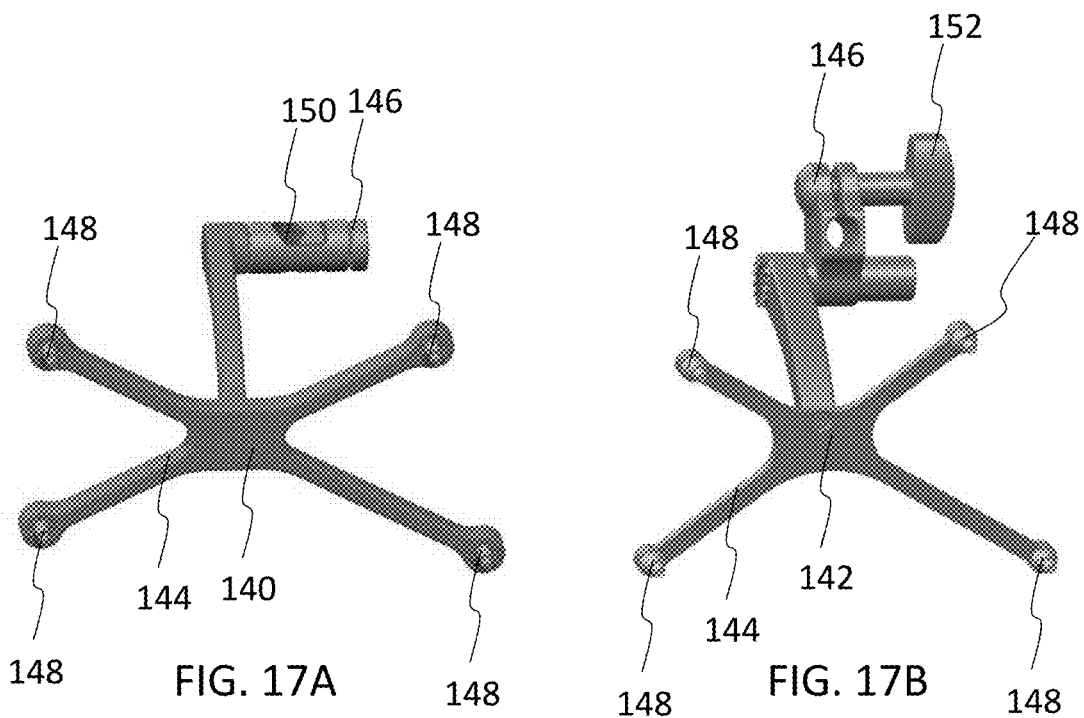

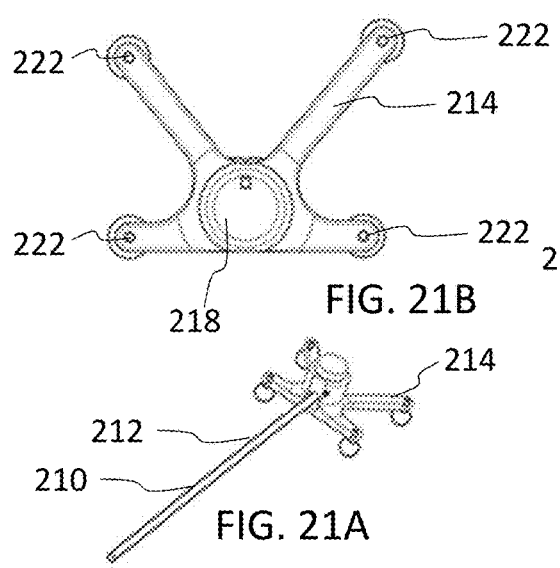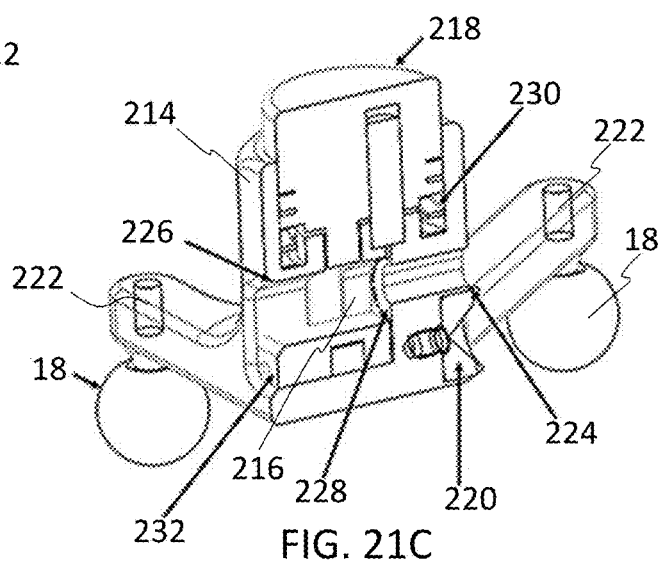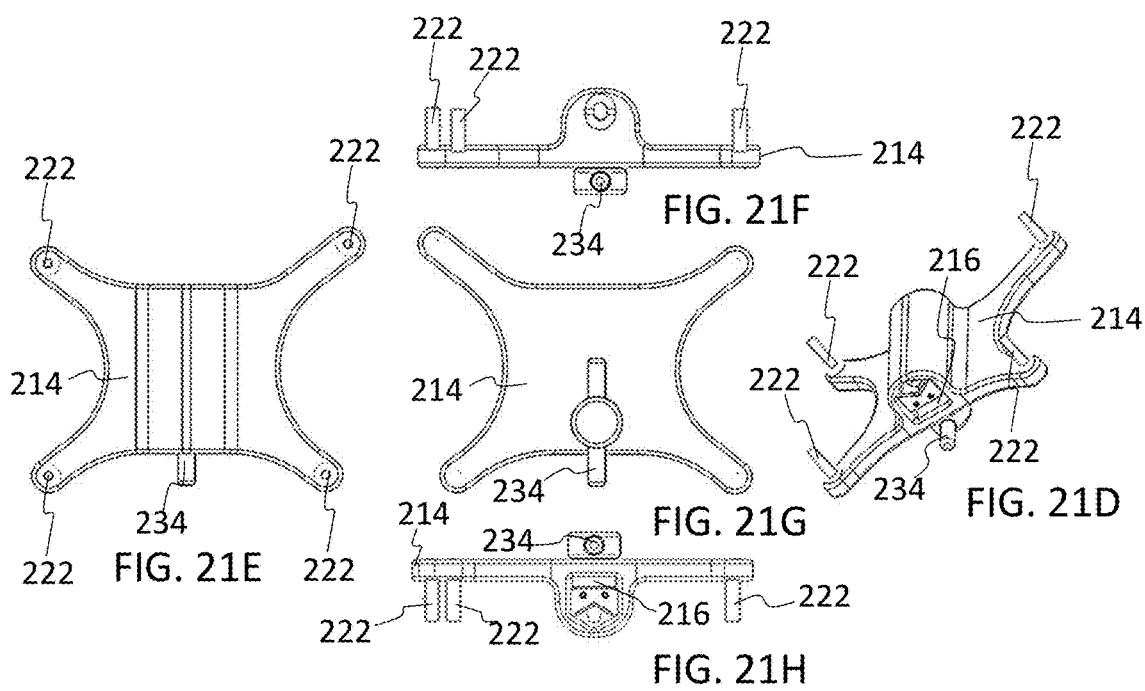

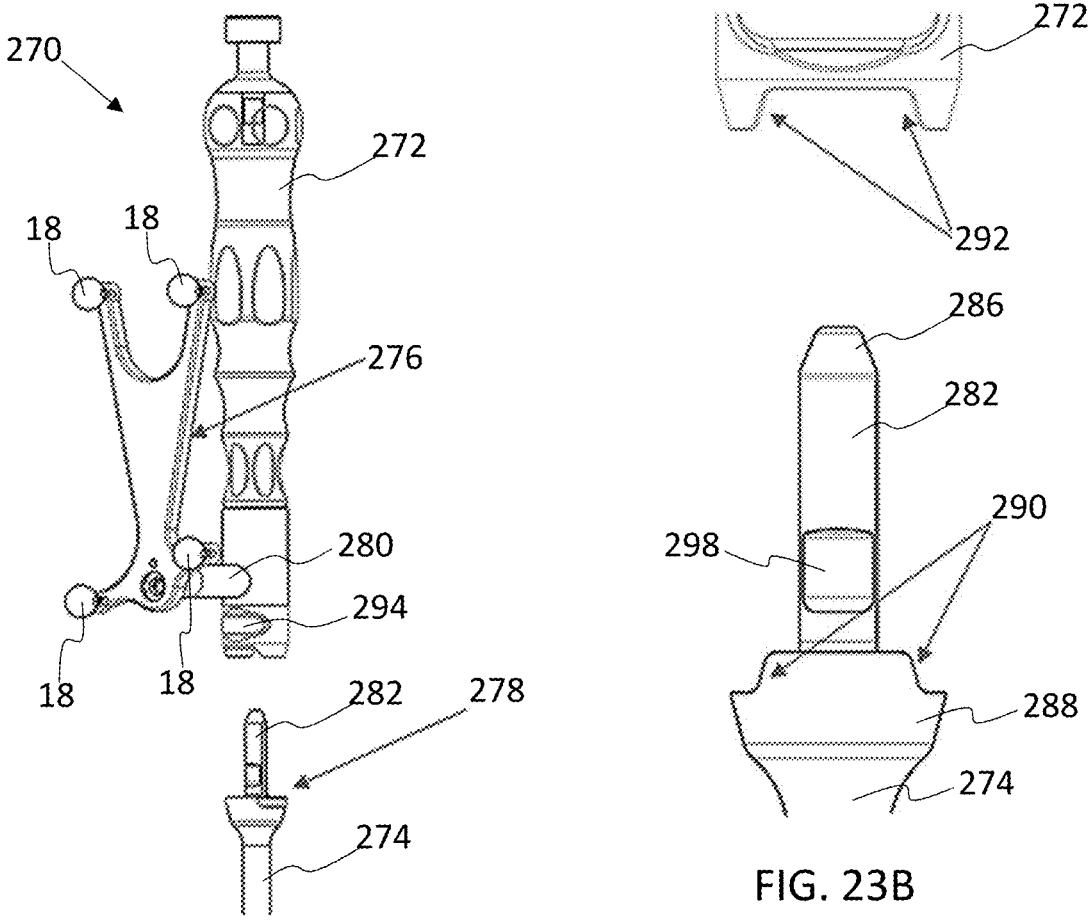
FIG. 23A
FIG. 23B
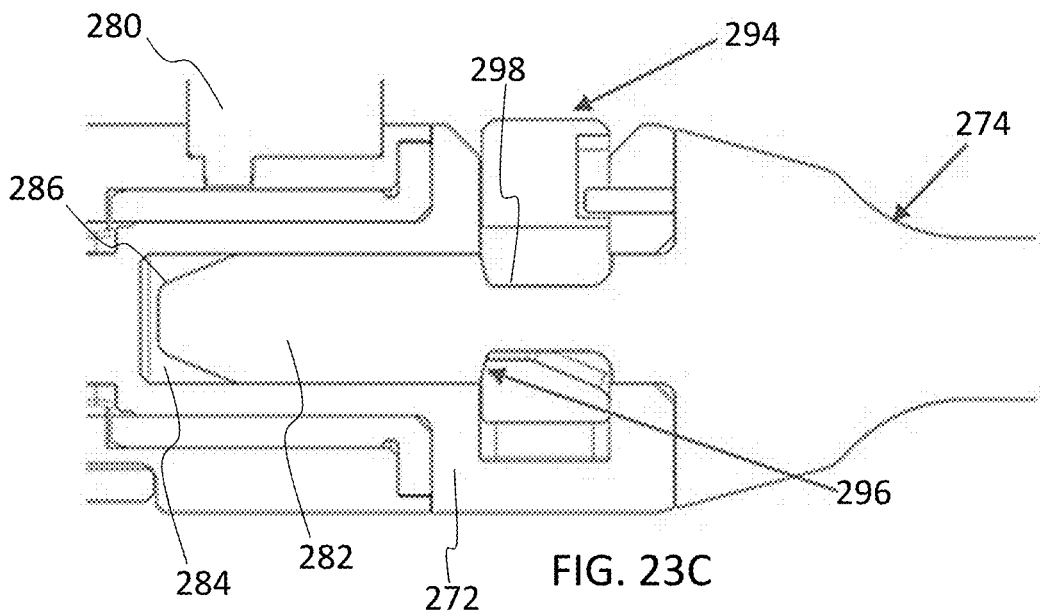
FIG. 23C

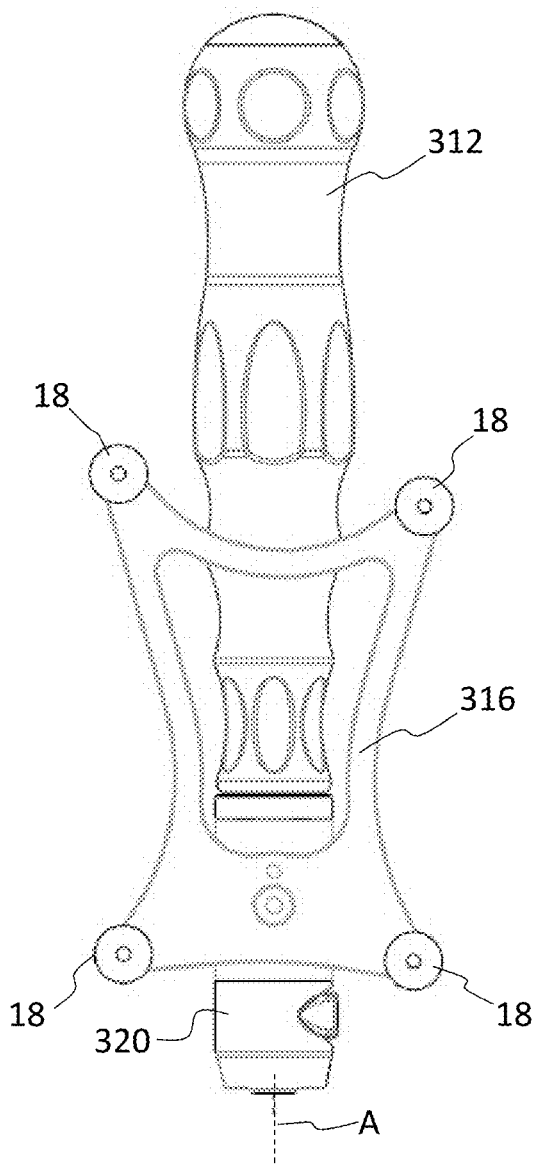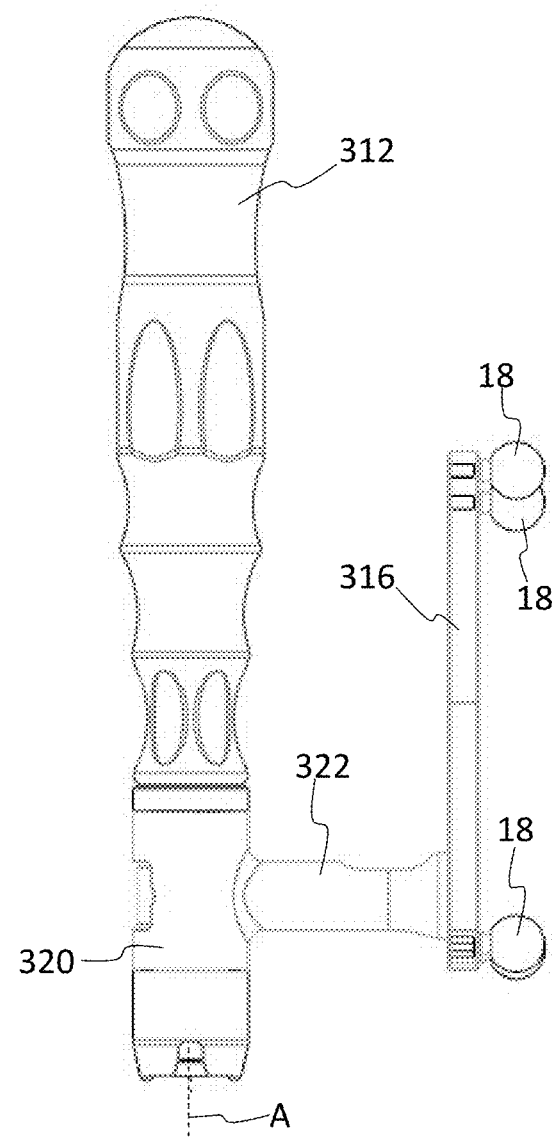
FIG. 25B
FIG. 25C ns and methods for improved robot-assisted surgery, and, in particular, navigated surgical instruments for access, preparation, and/or placement of interbody fusion devices.

BACKGROUND

Position recognition systems are used to determine the position of and track a particular object in 3-dimensions (3D). In robot-assisted surgeries, for example, certain objects, such as surgical instruments, need to be tracked with a high degree of precision as the instrument is being positioned and moved by a robot or by a physician, for example.

Infrared signal-based position recognition systems may use passive and/or active sensors or markers for tracking the objects. In passive sensors or markers, objects to be tracked may include passive sensors, such as reflective spherical balls, which are positioned at strategic locations on the object to be tracked. Infrared transmitters transmit a signal, and the reflective spherical balls reflect the signal to aid in determining the position of the object in 3D. In active sensors or markers, the objects to be tracked include active infrared transmitters, such as light emitting diodes (LEDs), and thus generate their own infrared signals for 3D detection.

With either active or passive tracking sensors, the system then geometrically resolves the 3-dimensional position of the active and/or passive sensors based on information from or with respect to one or more of the infrared cameras, digital signals, known locations of the active or passive sensors, distance, the time it took to receive the responsive signals, other known variables, or a combination thereof.

There is a need to provide improved systems and methods for robot-assisted surgeries, improved navigation of surgical instruments, and/or improved hardware and software for access, preparation, and/or placement of interbody fusion devices, for example. There is a specific need to overcome the loss of tracking or increase tracking accuracy by utilizing different types of optical markers.

SUMMARY

To meet this and other needs, devices, systems, and methods for accessing, preparing, and placing interbody fusion devices are provided. A surgical robotic system is provided which assists a user with one or more surgical procedures. Navigable instrumentation, which includes instruments capable of being navigated, and navigation software allow for the navigated placement of interbody fusion devices or other surgical devices. The interbody implant navigation may involve navigation of access instruments (e.g., dilators, retractors, ports), disc preparation instruments, trials, inserter instruments, and the like. The system allows for locating anatomical structures in open or minimally invasive (MIS) procedures and navigation of surgical instruments and interbody fusion devices.

According to one embodiment, a surgical robot system includes a robot having a base, including a computer, a display electronically coupled to the computer, a robot arm electronically coupled to the computer and movable based on commands processed by the computer, an end-effector electronically coupled to the robot arm, the end-effector including a quick-connector, an articulating arm having a first end coupled to the end-effector by the quick-connector and a second end, an access instrument coupled to the second end of the articulating arm, and a camera configured to detect one or more tracking markers. The access instrument may be a retractor or access port, for example.

The surgical robot system may include one or more of the following features. The end-effector may be a motion lock end-effector configured to prevent motion of the robot arm when attached to the robot arm. The quick-connector may include a male portion receivable within a female portion within the first end of the articulating arm. The articulating arm may include a release button configured to allow for quick attachment and detachment of the articulating arm to the end-effector. The end-effector may connect to the robot arm by clamping over a sterile arm drape. The second end of the articulating arm may include a threaded attachment mount for attachment to the access instrument. The articulating arm may include a plurality of joints that are configured to be locked and unlocked by a locking knob.

According to one embodiment, a robotic navigation system includes a robot and at least one navigable instrument. The robot may include a base, including a computer, a display electronically coupled to the computer, a robot arm electronically coupled to the computer and movable based on commands processed by the computer, an end-effector electronically coupled to the robot arm, the end-effector including a quick-connector, an articulating arm having a first end coupled to the end-effector with the quick-connector and a second end, an access instrument coupled to the second end of the articulating arm, and a camera configured to detect one or more tracking markers. The navigable instrument may include an array of tracking markers trackable by the camera. The navigable instrument may be configured to access, prepare, and/or place an interbody implant. For example, the navigable instrument may be a trial, cup curette, ring curette, cobb, elevator, osteotome, rasp, rake, sizer, shaver, paddle distractor, scraper, dilator, or inserter.

According to one embodiment, a method of robotic navigation may include one or more of the following steps: navigating a dilator including an initial dilator and a tracking array having a plurality of tracking markers to a position based on output from a robot comprising a computer, a display electronically coupled to the computer, and a camera configured to detect the tracking markers; removing the tracking array from the initial dilator; inserting subsequent dilators to prepare an access space; re-attaching the tracking array to the one of the dilators to track the position while placing an access instrument at the access space; and connecting the access instrument to an articulating arm coupled to an end-effector mounted on an arm of the robot. In this method, the initial dilator may be directly navigated and the access instrument may be indirectly navigated to the surgical site.

According to another embodiment, a robotic navigation system includes a robot and a navigable inserter. The navigable inserter may include a sleeve having a longitudinal axis, a rotatable body coupled to the sleeve, and an array of tracking markers connected to the rotatable body. The rotatable body may be configured to rotate about the longitudinal axis such that the array is viewable by the camera. The inserter may be a threaded or forked inserter, for example. The threaded inserter may include a threaded rod and a driver shaft positionable through the body and the sleeve. The threaded rod may terminate with a distal threaded tip configured to engage an implant. The forked inserter may include a forked rod positionable through the body and the sleeve. The forked rod may terminate with a distal forked tip configured to engage an implant.

The inserter may include one or more of the following features. The rotatable body may include a cavity that houses a translating member including a tapered key. The tapered key may be configured to mate with one or more keyseats in the sleeve of the inserter. A spring may be positioned along the translating member, and the spring may provide force for holding the key in the keyseat. The rotatable body may include a button. When the button is depressed, the spring is compressed and the tapered key translates away from the keyseat, thereby allow the rotatable body and array to rotate. When the button is released, the key engages with the keyseat, thereby locking the rotatable body and the array. The array may have a first index position and a second index position 180 degrees opposite to the first index position. The rotatable body may include a locknut and a spring positioned in an axial direction concentric with the longitudinal axis. The rotatable body may include two tapered surfaces and the sleeve may include two corresponding tapered surfaces such that when the tapered surfaces mate together, the rotatable body and array are locked in position. When the locknut is in a downward position, the tapered surfaces mate and the rotatable body and array are locked, and when the locknut is in an upward position, the tapered surfaces separate and the rotatable body and array are free to rotate.

According to another embodiment, a method of robotic navigation may include navigating an inserter comprising a sleeve having a longitudinal axis, a rotatable body coupled to the sleeve, and an array of tracking markers connected to the rotatable body to a position based on output from a robot comprising a computer, a display electronically coupled to the computer, and a camera configured to detect the tracking markers; and rotating the rotatable body and array such that the tracking markers are in a line of sight of the camera. The array may be moved into one of two index position 180 degrees opposite to one another or into one of four index positions 90 degrees apart from one another, for example.

According to another embodiment, a robotic navigation system includes a robot and a navigable instrument. The navigable instrument may include a handle having a longitudinal axis, a body coupled to the handle, an array of tracking markers connected to the body with an array post, and a detachable shaft and/or a detachable tip configured to perform a surgical function. For example, the tip may be a trial, cup curette, ring curette, cobb, elevator, osteotome, rasp, rake, sizer, shaver, paddle distractor, or scraper.

The navigable instrument may include one or more of the following features. The shaft may include an extension configured to be received in a bore within the handle, and the shaft may include a radial shoulder and a transition between the radial shoulder and the extension. The transition may include a cross-pin configured to be received in one or more slots in the handle. The shoulder may include one or more tapered surfaces and the handle may include one or more corresponding tapered surfaces. When the shaft is connected to the handle, the tapered surfaces engage thereby constraining movement of the shaft relative to the handle. The extension may include a recess and the handle may include a latch configured to be positioned within the recess, thereby locking the handle to the shaft.

According to yet another embodiment, a navigable trial includes a trial shaft and a detachable trial head. The trial shaft includes a hook at its distal end with a pin and a moveable plunger extending through the shaft. The trial head includes a first opening configured to receive the moveable plunger and a second opening configured receive the pin of the hook. When the plunger is positioned within the first opening in trial head, the trial head is locked in place. The trial head is fixed rotationally by the hook and plunger, which allows the trial to be manipulated inside the disc space.

According to yet another embodiment, a navigable trial includes a trial shaft and an expandable trial head. The navigable trial includes an array with a plurality of fixed markers and a moveable marker configured to slide within a pre-determined path to provide feedback on a height of the expandable trial head, wherein translation of the moveable marker may correspond to the height of the trial head.

Also provided are kits including navigable dilators, navigable access and trialing instruments, navigable inserters, retractors and access ports, implants and fusion devices of varying types and sizes, k-wires, and other components for performing the procedures.

DESCRIPTION OF THE DRAWINGS

FIGS. 8A-8E show alternative embodiments of the array handle assemblies;

FIGS. 10A-10G show embodiments of interbody inserters with different index positions;

FIGS. 12A-12B show an embodiment of a navigable inserter assembly with a threaded-style connector;

FIGS. 13A-13B show an embodiment of a navigable inserter assembly with a forked-style connector;

FIGS. 15A-15D provide embodiments of inserter verification adapters suitable for verifying the navigable instruments prior to use;

FIGS. 17A-17B show embodiments of dynamic reference bases (DRB);

FIGS. 21A-21H provide another embodiment of a navigated dilator holder;

FIGS. 23A-23E depict embodiments of quick connect and release mechanisms for the navigated instruments;

FIGS. 25A-25C provide another embodiment of a navigated instrument handle with a rotatable array mechanism;

DETAILED DESCRIPTION

Figure 1:
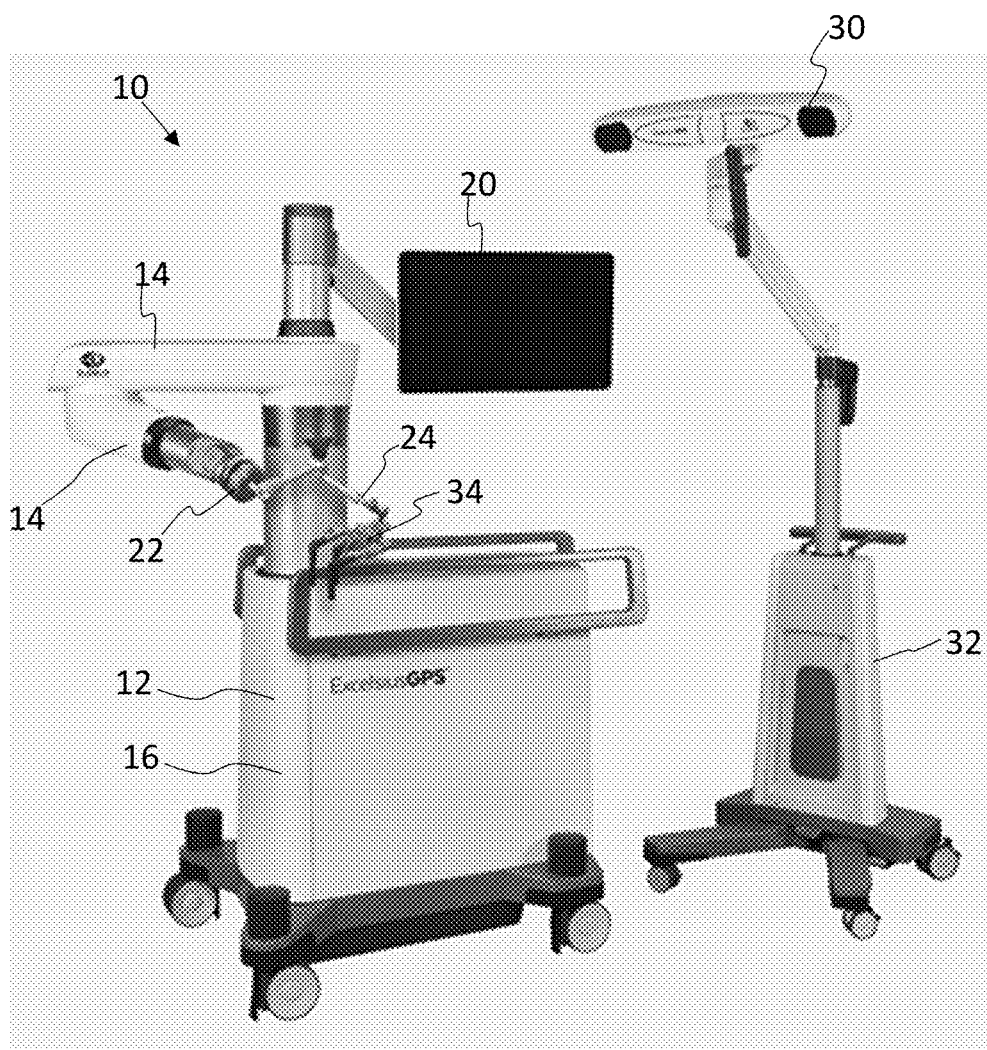
FIG. 1 illustrates a surgical robotic system in accordance with an exemplary embodiment.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
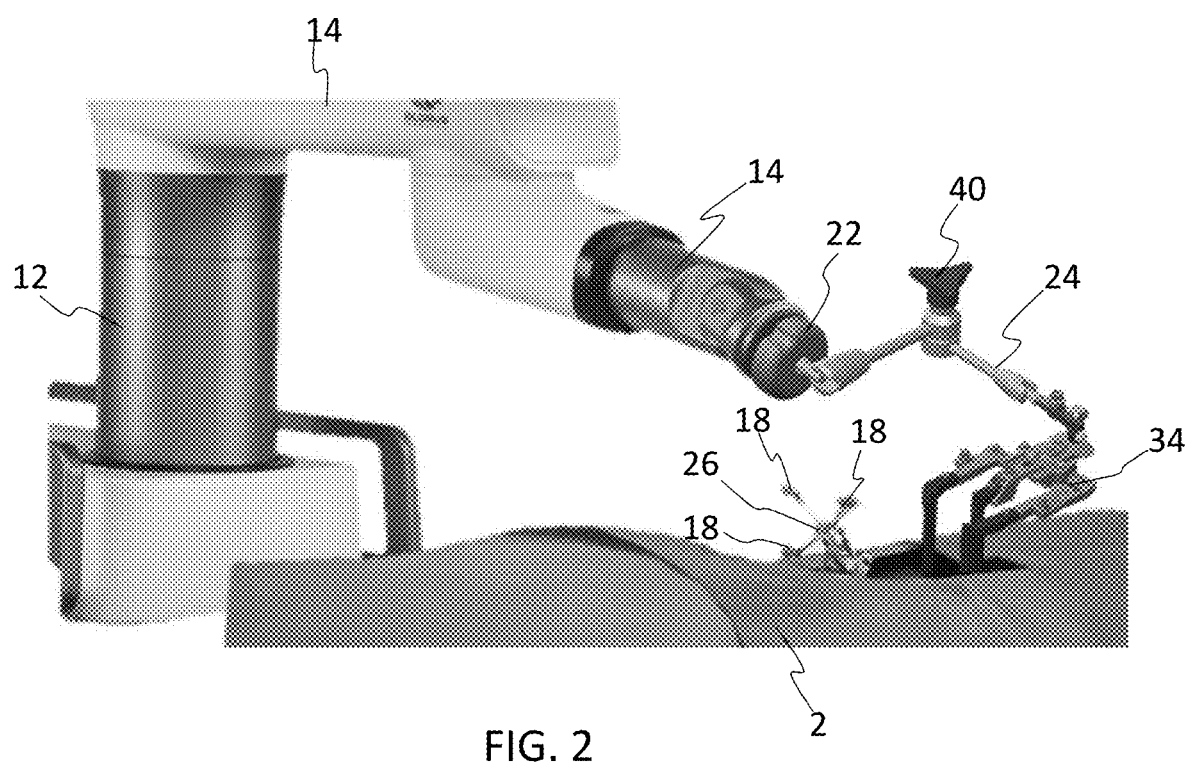
FIG. 2 provides a close-up view of the surgical robotic system of FIG. 1 configured for performing an operation on a patient.

Turning now to the drawing, FIGS. 1 and 2 illustrate a surgical robot system 10 in accordance with an exemplary embodiment. Surgical robot system 10 may include, for example, a surgical robot 12, one or more robot arms 14, a base 16, a display or monitor 20 (and optional wireless tablet), an end-effector 22, for example, for securing an articulating arm 24, and one or more tracking markers 18. The surgical robot system 10 may include a patient tracking device 26 including one or more tracking markers 18, which is adapted to be secured directly to the patient 2 (e.g., to the bone of the patient 2).

The surgical robot system 10 may also utilize a camera 30, for example, positioned on a camera stand 32. The camera stand 32 can have any suitable configuration to move, orient, and support the camera 30 in a desired position. The camera 30 may include any suitable camera or cameras, such as one or more infrared cameras (e.g., bifocal or stereophotogrammetric cameras), able to identify, for example, active and passive tracking markers 18 in a given measurement volume viewable from the perspective of the camera 30. The camera 30 may scan the given measurement volume and detect the light that comes from the markers 18 in order to identify and determine the position of the markers 18 in three-dimensions. For example, active markers 18 may include infrared-emitting markers that are activated by an electrical signal (e.g., infrared light emitting diodes (LEDs)), and passive markers 18 may include retro-reflective markers that reflect infrared light (e.g., they reflect incoming IR radiation into the direction of the incoming light), for example, emitted by illuminators on the camera 30 or other suitable device.

The surgical robot 12 is able to control the translation and orientation of the end-effector 22. The robot 10 may be able to move end-effector 22 along x-, y-, and z-axes, for example. The end-effector 22 can be configured for selective rotation about one or more of the x-, y-, and z-axis, and a Z Frame axis (such that one or more of the Euler Angles (e.g., roll, pitch, and/or yaw) associated with end-effector 22 can be selectively controlled). In some exemplary embodiments, selective control of the translation and orientation of end-effector 22 can permit performance of medical procedures with significantly improved accuracy.

The robotic positioning system 12 includes one or more computer controlled robotic arms 14 to assist surgeons in planning the position of stereotaxic instruments relative to intraoperative patient images. The system 10 includes 2D & 3D imaging software that allows for preoperative planning, navigation, and guidance through a dynamic reference base, navigated instruments and positioning camera 30 for the placement of spine, orthopedic, or other devices. Further details of surgical robotic and navigation systems can be found, for example, in U.S. patent publication No. 2019/0021795 and U.S. patent publication No. 2017/0239007, which are incorporated herein by reference in their entireties for all purposes.

With further emphasis on FIG. 2, the robot 12 and/or surgeon may position the end effector 22 and the articulating arm 24 into a desired position for mounting an access instrument 34, such as a retractor or port system, through which the surgeon can use navigated instruments to perform surgery. Power to the robotic arms 14 may be shut off once the motion lock end effector 22 is attached to the arm 14. In one embodiment, this gives the surgeon full control of the instruments, and the system 10 does not perform or physically guide the surgery. The navigation camera 30 tracks the position of instruments in real time and provides an image on the monitor 20, along with the patient's images, for example, to provide guidance to the surgeon.

Figure 3:
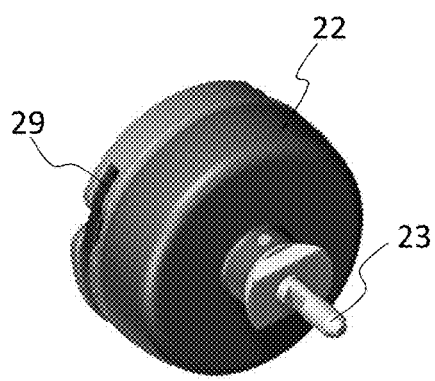
FIG. 3 is an end-effector for connecting an articulating arm to the surgical robotic system.
Figure 4A:
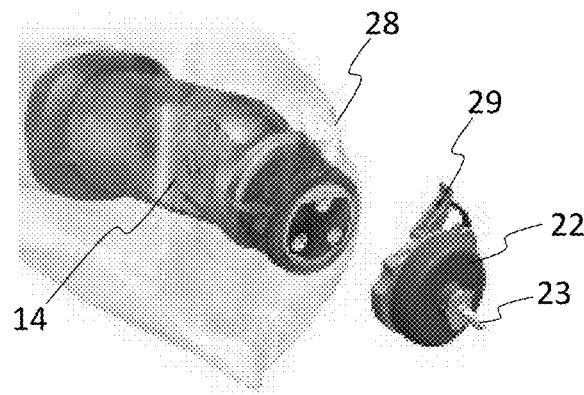
FIGS. 4A-4C are steps depicting coupling the end-effector of FIG. 3 to the robotic arm of the surgical robot.
Figure 4B:
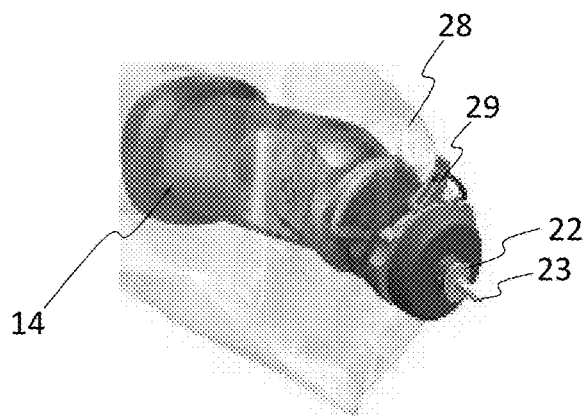
Figure 4C:
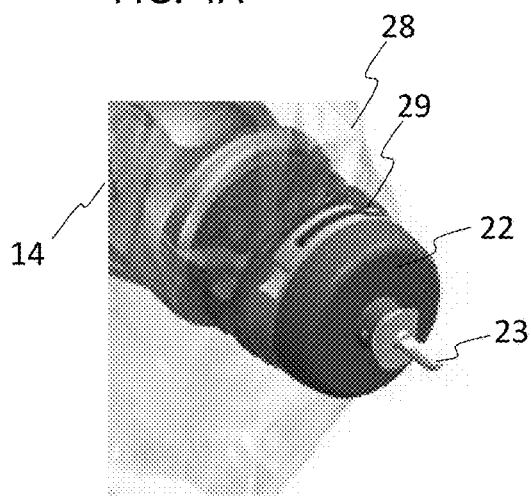
Figure 5:
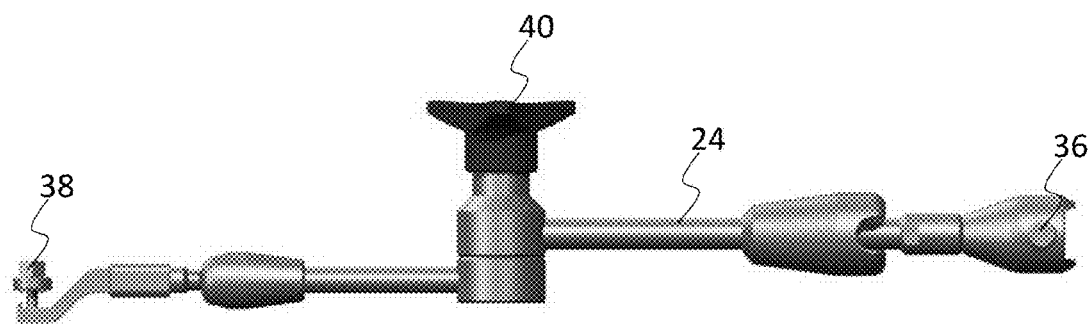
FIG. 5 illustrates an embodiment of an articulating arm which serves as a link between the robotic arm of the surgical robot and an access instrument, such as a retractor or access port.

Turning to FIGS. 3-5, the motion lock end-effector 22 and articulating arm 24 are shown in greater detail. The motion lock end-effector 22 and articulating arm 24 provide a rigid attachment connection for an access instrument 34, such as a surgical retractor (shown in FIG. 19B) or access port (shown in FIG. 19C). Alternatively, a standard table mounted articulating arm, retractor, or port may be used if desired. The motion lock end-effector 22 prevents robotic arm motion when attached to the robot arm 14. The end-effector 22 provides a rigid quick-connect connection to the articulating arm 24, which is used to rigidly attach and position the access instrument 34 (e.g., retractor or arm-mounted port).

As shown in FIGS. 4A-4C, the end-effector 22 connects to the robotic arm 14 by clamping over the sterile arm drape 28. The end-effector 22 includes a male portion 23 which is receivable within a female portion within one end of the articulating arm 24. The articulating arm 24 attaches to the male portion 23 of the end-effector 22 with a release button 36. The release button 36 allows for quick attachment and detachment of the articulating arm 24 to the end-effector 22. The attachment mount 38 on the opposite end of the articulating arm 24 attaches to the access instrument 34 (e.g., retractor or arm-mounted port). The distal end of the articulating arm 24 may have a threaded attachment mount 38 for connection to retractor systems or ports 34. Once the articulating arm 24 is positioned and an access instrument 34 is attached thereto, the locking knob 40 may be tightened to secure the assembly. The articulating arm 24 serves as a link between the robotic arm 14 and the surgical retractor or access port 34. The articulating arm 24 may have several joints which are locked and unlocked by tightening or loosening the locking knob 40, allowing for quick adjustments to retractor position, similar to standard table mounted retractor arms.

In this manner, the robotic arm 14 may be used as a rigid fixation point for a retractor or port 34 to provide access to the spine. Once the sterile drape 28 is fitted over the robot 12, the robotic arm 14 can be moved into position. The end-effector 22 may be attached to the robotic arm 14 through the interface plate, over the sterile drape 28. A magnetic assist may help to position and self-align the end-effector 22. The drape-friendly clamp 29 allows the end effector 22 to be removed and reattached up to three times in a procedure without damaging the drape 28. The end-effector 22 is powered wirelessly from the robotic arm 14. When attached to the robotic arm 14, the motion lock end-effector 22 sends a signal to the system 10 to restrict all motion (e.g., stabilizers and robotic arm 14) and prevent unintended movement as a safety feature while the access instrument 34 (e.g., retractor blades or access port) is used in the patient 2 and the operation is performed.

Figure 6A:
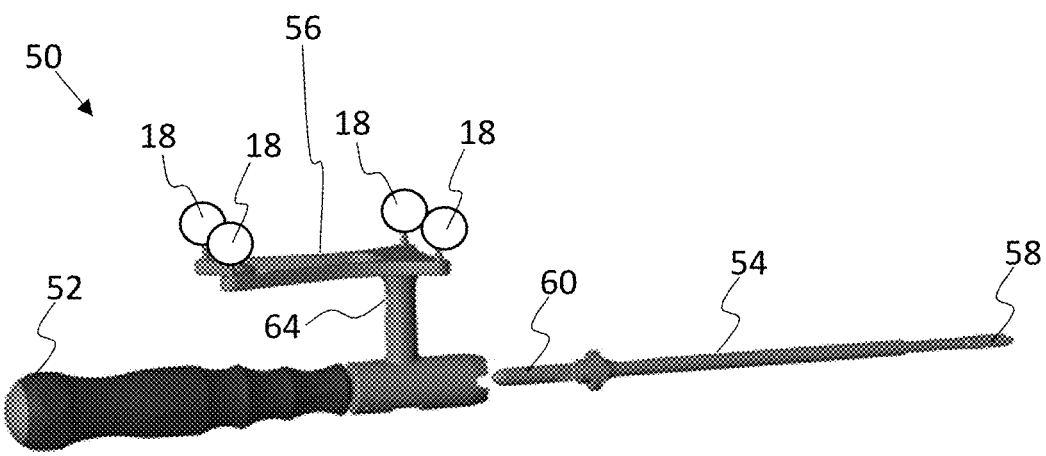
FIGS. 6A-6B show an embodiment of a navigable instrument and array handle assembly having a quick connect feature configured for use with the robotic system.
Figure 6B:
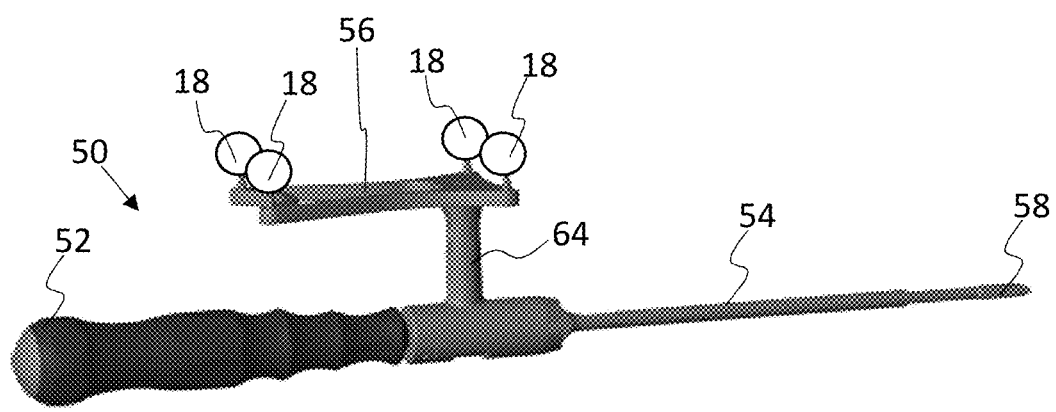
Figure 7A:
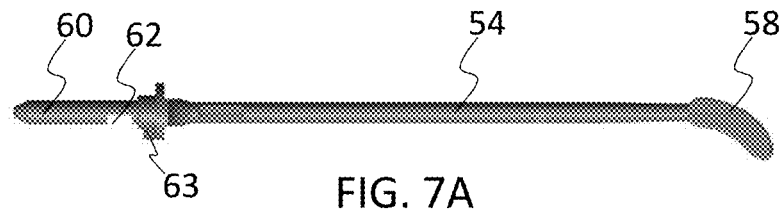
FIGS. 7A-7L show a plurality of different instruments or a kit including disc preparation and trial instruments.
Figure 7B:
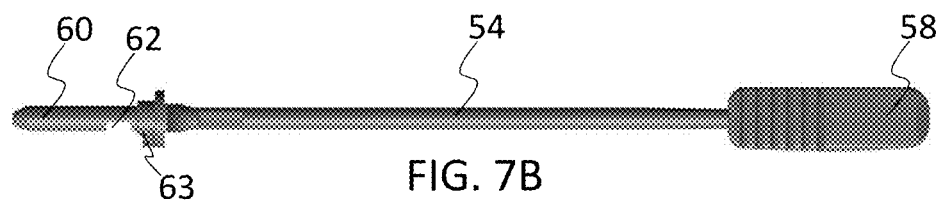
Figure 7C:
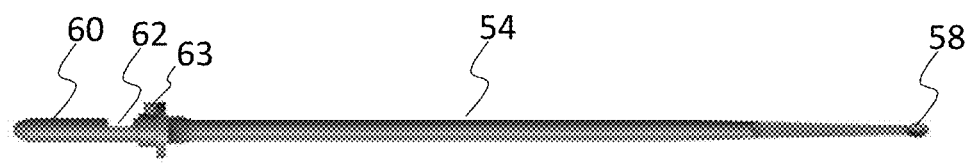
Figure 7D:
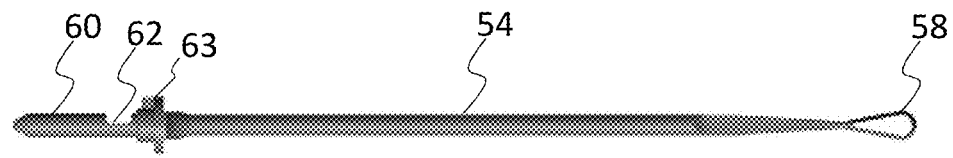
Figure 7E:
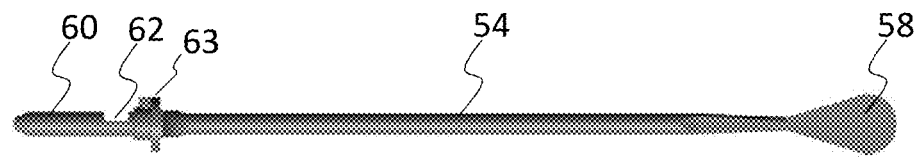
Figure 7F:
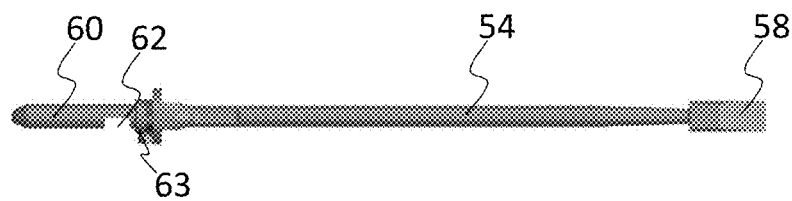
Figure 7G:
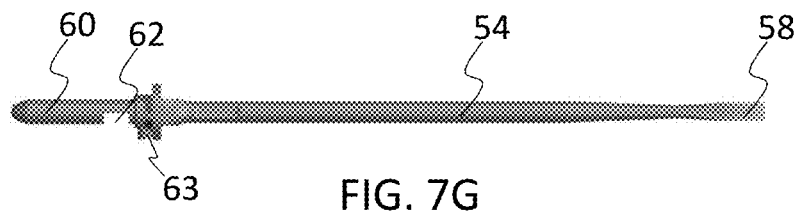
Figure 7H:
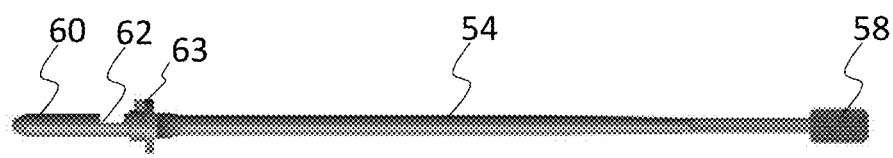
Figure 7I:
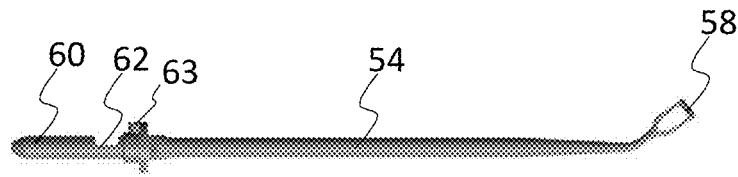
Figure 7J:
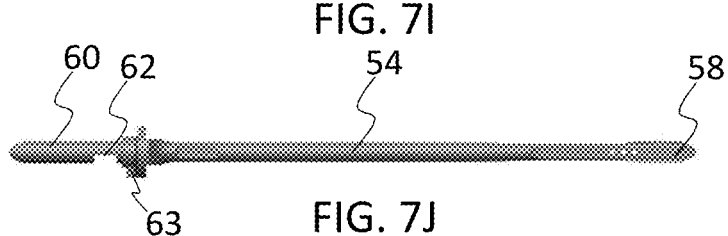
Figure 7K:
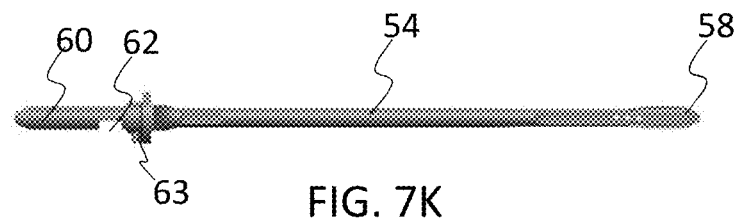
Figure 7L:
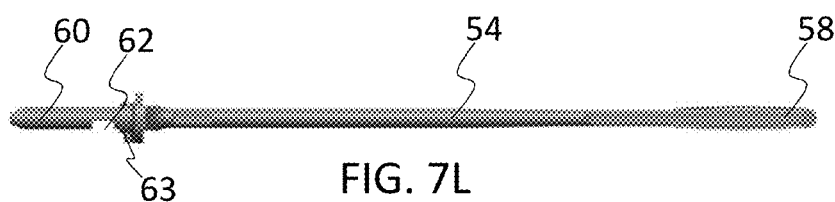
Figure 9A:
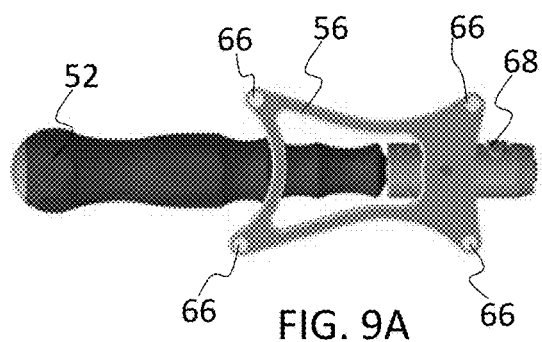
FIGS. 9A-9F show a plurality of different array handles or a kit including straight handles and T-handles.
Figure 9B:
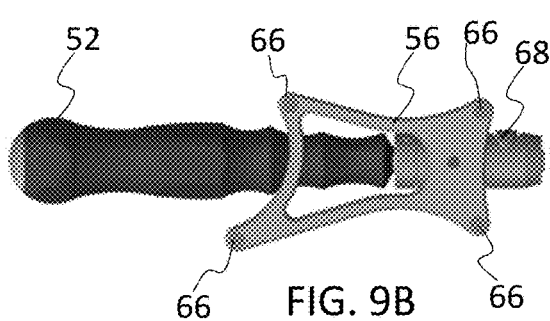
Figure 9C:
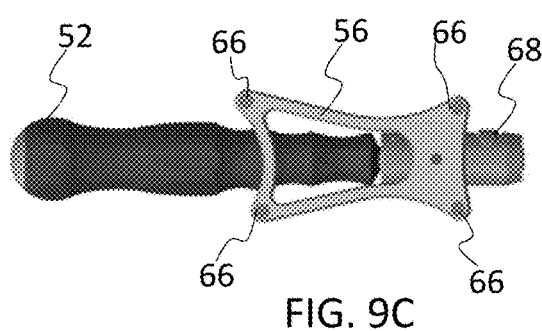
Figure 9D:
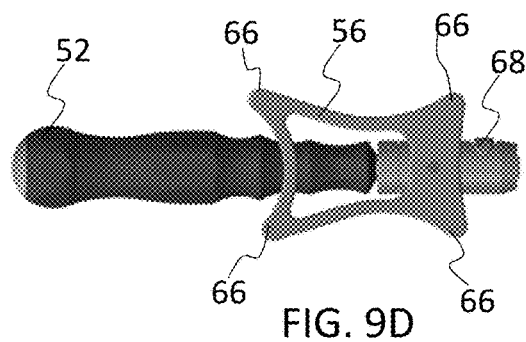
Figure 9E:
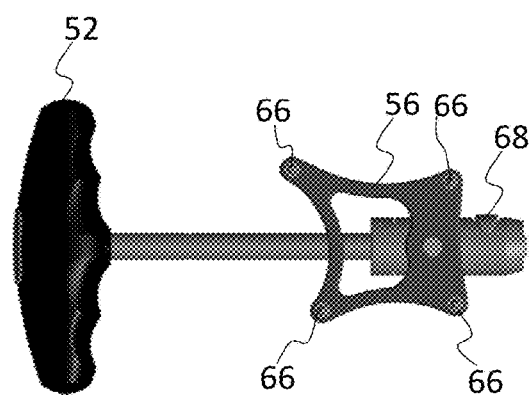
Figure 9F:
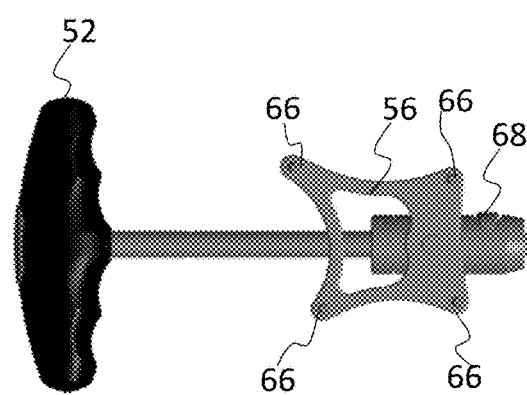

Turning now to FIGS. 6A-6B, a navigable instrument 50 is shown. Navigated instruments 50 may include dilators, disc preparation instruments (e.g., curettes, Cobb elevators, rasps, scrapers, etc.), trials, and inserters, for example. The navigable instrument 50 may include a handle portion 52, a shaft portion 54, and an array 56 including one or more tracking markers 18 for tracking the instrument 50. The array 56 may be affixed to the handle body 52 with an array post 64. The array 56 may be configured to rotate about the central axis of the handle 52. The handle portion 52 may include straight and T-handle styles. The shaft portion 54 may have a tip 58 at its distal end configured to perform one or more functions and a quick-connector 60 at its proximal end configured to quickly connect and disconnect from the handle portion 52, thereby providing for rigid attachment to the array handle assembly. A slot 62 in the shaft 54 retains the instrument and a pin 63 controls orientation. Instruments 50 are assembled with the selected array handle 52 by inserting the instrument shaft 54 into the handle 52 with the alignment pin 63 and groove 62 aligned until fully seated. When fully inserted, an audible click is heard and the instrument 50 is locked.

As shown in FIGS. 7A-7L, the disc preparation and trial instruments 50 may include trials (shown in FIGS. 7A and 7B), cup curettes (shown in FIG. 7C), ring curettes (shown in FIG. 7D), cobbs (shown in FIG. 7E), elevators (shown in FIG. 7F), osteotomes (shown in FIG. 7G), rasps (shown in FIG. 7H), rakes (shown in FIG. 7I), sizers/shavers (shown in FIG. 7J), paddle distractors (shown in FIG. 7K), scrapers (shown in FIG. 7L), and other suitable instruments. Instruments 50 for lateral use may be longer in length, and those for posterior use may be shorter in length. A kit may be provided with a variety of different instruments 50 in various sizes.

Disc preparation and trial instruments 50 may be used interchangeably with various array handles 52. The user may assign an instrument to an array handle 52 in the software prior to use. Representative models of disc preparation and trial instruments 50 are loaded in the software and may be selected from a list of instruments in the user interface.

Turning to FIGS. 8A-8E, the instruments 50 may be used with detachable array handles 52 that may have integrated arrays 56 for navigation. The instruments 50 may also be used freehand without navigation, if desired. Each instrument shaft 54 and corresponding array handle 52 are assembled prior to use. The array handles 52 may come in straight and T-styles, for example, to suit user preference. Each array 56 has a unique marker pattern that is recognized by the system 10. Arrays 56 may have one or more posts 66 (e.g., four posts 66) for attaching reflective markers 18 thereto. Each array 56 has a unique pattern which allows the system 10 to identify the array 56, and thereby identify the type of instrument 50. The array handles 52 are attached to the shafts 54 of the disc preparation instruments and trials for navigation. The handles 52 may include a release button 68 for removing the shafts 54 of the disc preparation instruments or trials. As shown in FIG. 8D, the array handle 52 may be verified through the use of an instrument and verification divot 70. A verification divot 70 located on the array post 64 may be used to verify other navigated instruments, for example, by placing the instrument tip 58 into the divot 70.

According to one embodiment shown in FIGS. 9A-9F, there are six different arrays 56 which may be distinguished to the user by a color and/or an etched number. The handles 52 may include a straight handle 52 with a red array 56 (shown in FIG. 9A), a straight handle 52 with a gold array 56 (shown in FIG. 9B), a straight handle 52 with a green array 56 (shown in FIG. 9C), a straight handle 52 with a blue array 56 (shown in FIG. 9D), a T-handle 52 with a purple array 56 (shown in FIG. 9E), and a T-handle 52 with a grey array 56 (shown in FIG. 9F), for example. Each array pattern may include four posts 66 for mounting reflecting markers 18 that are tracked by the optical cameras 30. The arrangement of these posts 66 is unique for each array handle 52. The array plates 56 may each have a unique color and laser marked number (e.g., Red "1"). These indicators allow the user to quickly assign a disc preparation instrument shaft 54 to the corresponding array handle 52 in the software (e.g., Red 1—Cobb 10 mm). Once the array handle 52 is verified, the instruments 50 may be exchanged during the procedure. A new instrument 50 must be reassigned and the array position adjusted, in order for the instrument 50 to be correctly displayed for navigation. Various instruments 50 may be navigated during a procedure.

With emphasis on FIGS. 10A-10B, the array handles 52 allow the array 56 to rotate about the central axis of the handle 52 to ensure that the array 56 is in view of the camera 30 or to change the orientation of the instrument 50 relative to the patient anatomy and the array 56. The user may press the rotation index button 72 to rotate the array 56 until it clicks into a new index position 74, as desired. The index positions 74 may be etched on the handle 52 with an indicator 76, for example. A first index position 74 is identified by the letter A (shown as indicator 76 in FIG. 8A) that aligns with a rectangular marking next to the divot 70. As shown in FIG. 10A, the T-handles 52 may index the instrument 50 to four index positions 74 (A, B, C, D) that are located 90° apart. As shown in FIG. 10B, the straight handles 52 may index the instrument 50 to two index positions 74 (A, C) that are 180° apart. Each index position 74 may be denoted on the array handle 52 by an indicator letter 76 (A, B, C, D, or A, C, respectively) corresponding with the respective index positions 74. When the instrument shaft 54 and array handle 52 are assembled, the index position 74 starts at "A", as shown on the position identifier 76 on the handle 52. All instruments 50 may be verified and initially displayed on the software in the "A" index position 74. The user then inputs the index orientation into the software when the array 56 is rotated to a new index position 74, to ensure the displayed instrument model is oriented in the same position as the actual instrument 50.

The array 56 can be rotated relative to the shaft 54 to ensure that the array 56 is in view of the camera 30. The user presses the index button 72 and rotates the array 56 around the handle 52 until it clicks into one of the index positions 74. The index position 74 starts at "A". When the index position 74 is changed to "B", "C", "D" (or later back to "A"), the user enters the position on the touchscreen monitor 20 of the robot 12. This allows the monitor 20 to display the correct orientation of the corresponding instrument model. Although two or four index positions 74 are shown in the embodiments, it will be appreciated that any suitable number and location of index positions 74 may be used.

All of the array handles 52 may have the same quick connect and release attachment mechanism. This allows any disc preparation or trial instrument shaft 54 to be assembled to any array handle 52. The user assigns an instrument 50 to each handle array 56 in the software. A release button 68 on the array handle 52 allows the instrument shaft 54 to be inserted or removed when pressed. A slot 62 may be incorporated into the connection mechanism which mates with a pin on all mating disc preparation and trial instruments to control rotational orientation.

Turning to FIG. 10C, a navigable interbody inserter instrument or interbody inserter 80 is further described. Navigable interbody inserters 80 may be configured to install lumbar interbody implants used in transforaminal (TLIF), posterior (PLIF), and lateral (LLIF) interbody fusion procedures, for example. It is also contemplated that the inserters 80 may be configured to install other interbody devices or implants. Depending on the implant design, the interbody inserters 80 may have a forked tip 96 or threaded tip 98 to hold the interbody implant or may be otherwise configured to retain the implant.

The interbody inserters 80 may have an array plate 82, a shaft or sleeve 84, a rotatable body 88, and an array post 90 connecting the array plate 82 to the body 88. For the threaded inserters 80, the inserter 80 may include a threaded rod 100 and driver shaft 102 positionable through the inserter body 88 and through the sleeve 84. The threaded rod 100 may terminate with a distal threaded tip 98 configured to engage the implant. For the forked inserters 80, the inserter 80 may include a forked rod 104 positionable through the inserter body and the sleeve 84, and may terminate with a distal forked tip 96 configured to engage the implant.

In one embodiment, the array post 90 may be permanently integrated to the body 88 of the inserter 80 with the body 88 free to rotate about the shaft or sleeve 84 of the inserter 80. The array plate 82 may have one or more posts 86 (e.g., four posts 86) for mounting reflecting markers 18 that are tracked by the optical camera 30. The array pattern may be unique to inserters 80. For example, all inserters 80 may have the same array pattern, regardless of which implant is being placed. The inserter array pattern may be different than the pattern on other array instruments (e.g., arrays 46, dilator array 114).

With emphasis on FIGS. 10D-10G, the rotatable body 88 (and attached array 82) may be permitted to rotate about the central axis sleeve 84 to ensure that the array 82 is in view of the camera 30 or to change the orientation of the inserter 80 relative to the patient anatomy. The user may press a rotation index button 94 and/or manipulate a knob 92 to rotate the array 82 until it is oriented into a new index position 74, as desired. The arrays 82 on the inserters 80 may be indexed to two index positions 74 (A, C, respectively) as shown in FIG. 10B. The index positions 74 may be identified on the instrument 80 with laser marking that are 180° apart in the same manner described for instrument 50. This allows the arrays 82 to be rotated, for example, to ensure that the array 82 is in view of the camera 30. To switch between index positions 74, the user may loosen the threaded knob 92 to rotate the array 82, for example, 180° to the opposite location. Then, the knob 92 may be tightened to secure the position. In another embodiment, the user presses an index button 94 to rotate the array 82. In FIGS. 10E and 10G, the inserters 80 are shown at the index position 74 identified as position "A". In FIGS. 10D and 10F, the index position 74 of the inserters 80 are changed to position "C". When the index position 74 is changed to "C" (or later back to "A"), the user enters the position on the monitor 20. This allows the monitor 20 to display the correct orientation of the corresponding instrument model.

Figure 11A:
FIGS. 11A-11E provides a plurality of different interbody inserter instruments or a kit including interbody inserters with different instrument connection features.
Figure 11B:
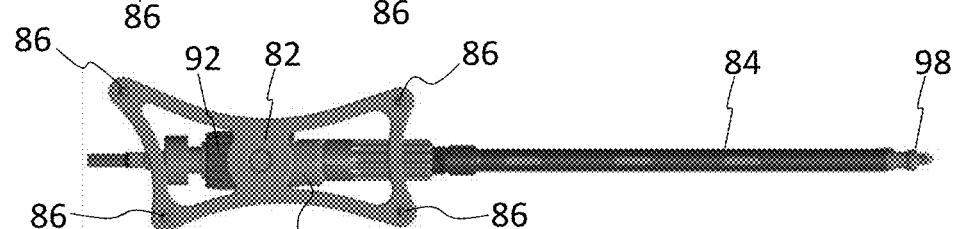
Figure 11C:
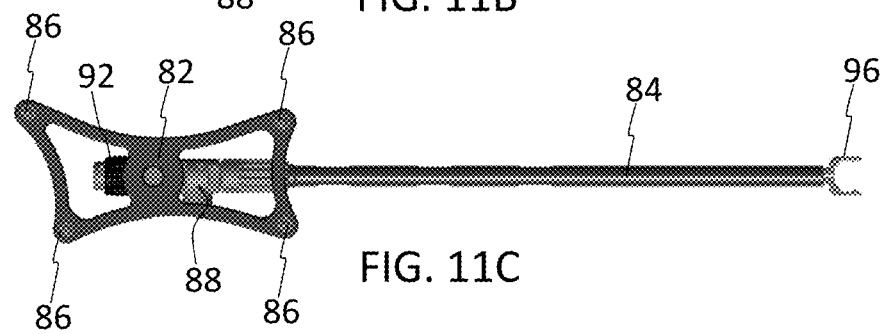
Figure 11D:
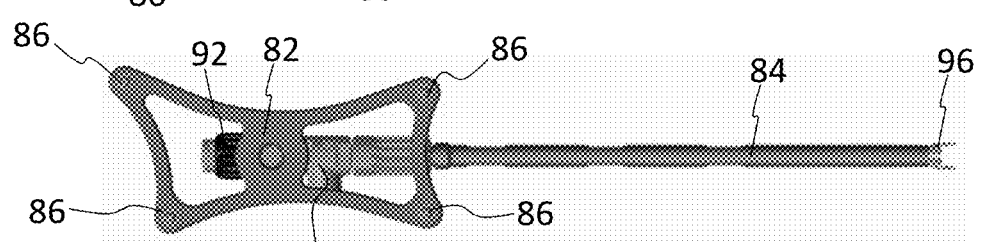
Figure 11E:
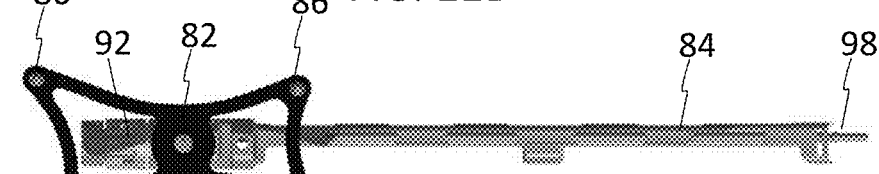

Turning to FIGS. 11A-11E, several embodiments of inserters 80 are shown. In FIG. 11A, the inserter 80 may include a forked distal tip 96 configured to retain a static posterior interbody spacer. In FIG. 11B, the inserter 80 may include a threaded distal tip 98 configured to retain an articulating expandable TLIF spacer. In FIG. 11C, the inserter 80 may include a forked tip 96 configured to retain an expandable lateral lumbar fusion device. In FIG. 11D, the inserter 80 may include a forked tip 96 configured to retain an expandable lumbar fusion implant. In FIG. 11E, the inserter 80 may include a threaded tip 98 configured to retain expandable interbody fusion spacer with integrated fixation. Although the forked 96 and threaded 98 embodiments are shown, it will be appreciated that the distal end of the inserter 80 may be configured in any way to hold an implant during the procedure. Based on the selected implant system, the implant inserter 80 corresponding to the implant system is identified in the software. Implant inserters 80 may include the integrated arrays 82 for navigation by the system 10.

Turning to FIGS. 12A-13B, the inserters 80 may be assembled as follows. With emphasis on FIGS. 12A-12B, to assemble the threaded inserter 80, the sleeve 84 may be inserted into the array assembly and the threaded rod 100 and driver shaft 102 may be inserted into the inserter body 88 and through the sleeve 84. One or more prongs 85 of the sleeve 84 may be aligned with the inserter body 88 to insert the sleeve 84 therein. The knob 89 may be rotated clockwise and threaded to the sleeve 84 to secure the assembly. With emphasis on FIGS. 13A-13B, to assemble the pronged inserter 80, the sleeve 84 may be inserted into the array assembly and the forked shaft 104 may be inserted into the inserter body 88 and through the sleeve 84. One or more prongs 85 of the sleeve 84 may be aligned with the inserter body 88 to insert the sleeve 84 therein. The knob 89 may be rotated clockwise and threaded to the sleeve 84 to secure the assembly.

Non-navigated instruments, such as tightening wrenches and torque-limiting drivers (for expandable device inserters) may be provided to work specifically with the interbody inserters 80. These ancillary instruments serve the same function as the instruments that work with the corresponding non-navigated interbody inserters. These non-navigated instruments are not rendered on patient imagery and are may be used to support mechanical functionality of the inserters 80, for example.

Turning now to FIGS. 14A-14G, a navigable dilator instrument or dilator 110 is shown. The navigable dilator 110 may include an initial dilator 112 and a dilator array 114 configured to be tracked by the robotic navigation system 10. The dilator array 114 may include a unique array pattern, a cavity or attachment window 116, a release button 118, and a verification divot 120. Similar to arrays 56 and 82, array 114 may have one or more posts 122 (e.g., four posts 122) for attaching tracking markers 18 thereto. The array 114 has a unique pattern which allows the system 10 to identify the array 114 and thereby identify the dilator 110 for navigation. The verification divot 120 may be used to verify with other navigated instruments 50, by placing the instrument tip 58 into the divot 120. The verification divot 120 may be located on the top of the array 114, for example.

Figure 14A:
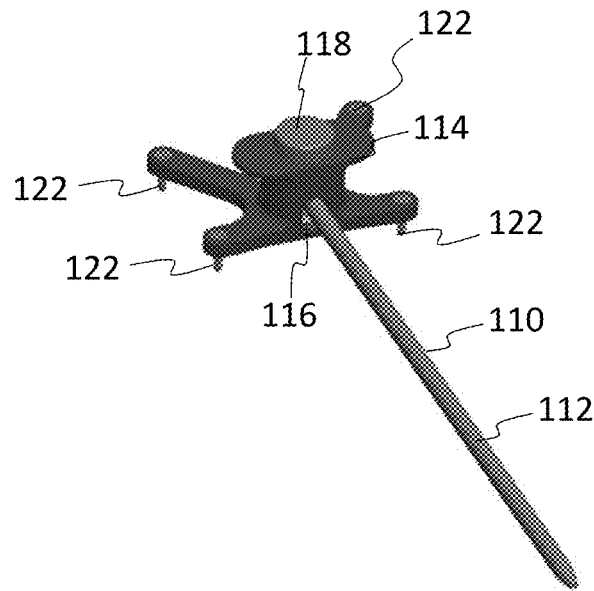
FIGS. 14A-14G provide an embodiment of a navigable dilator array with an initial dilator.
Figure 14B:
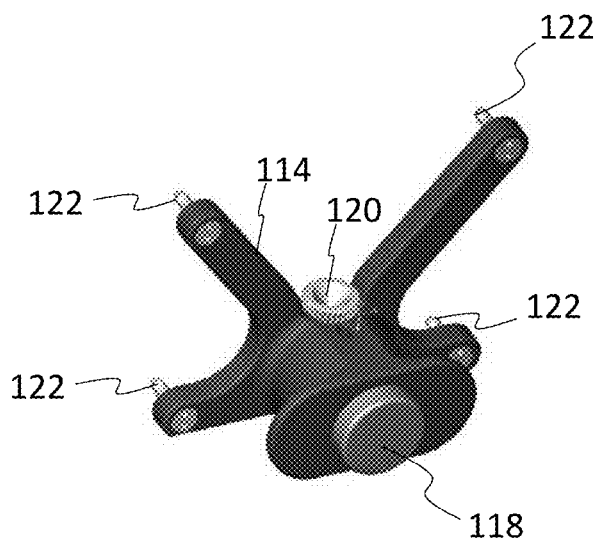
Figure 14C:
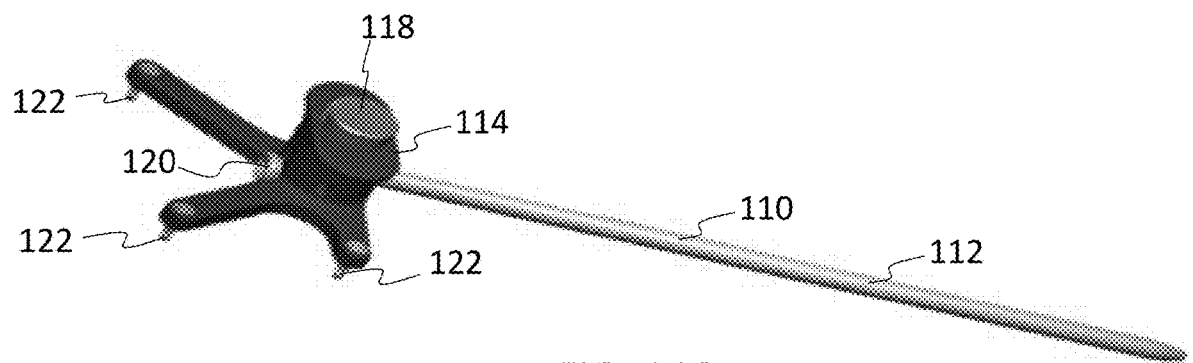
Figure 14D:
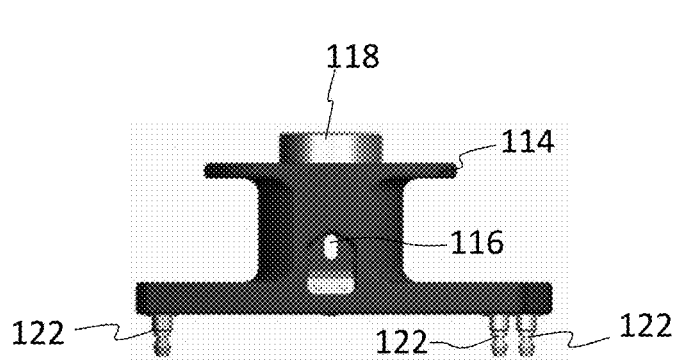
Figure 14E:
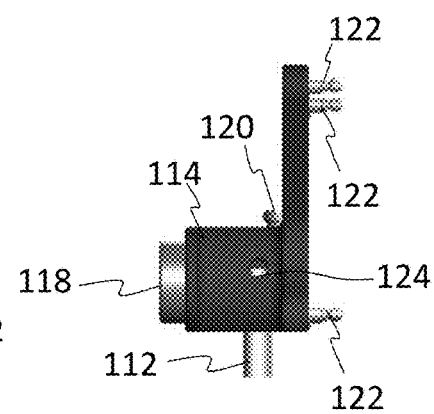

The dilator array 114 may attach to an initial dilator 112. The initial dilator 112 may include cannulas, such as 2 mm cannulas, insulated cannulas A, stainless steel cannulas A, or other suitable cannulas or dilators. As shown in FIG. 14D, to assemble the initial dilator 112 and dilator array 114, the release button 118 may be pressed to open the attachment window 116. The dilator 112 may be inserted into and through the window 116. As shown in FIG. 14E, a side viewing window 124 may be checked to ensure the dilator 112 is fully inserted in the array 114.

Figure 14F:
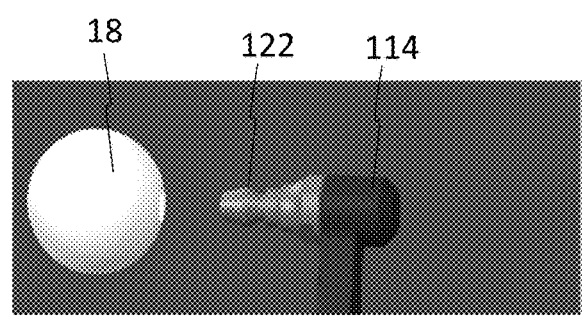
Figure 14G:
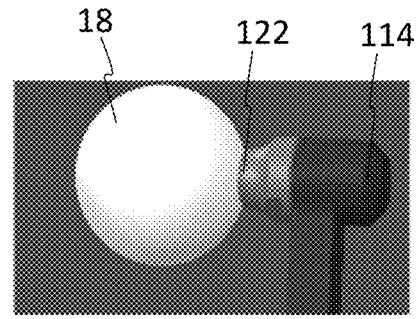

As shown in FIGS. 14F-14G, the markers 18 (e.g., disposable reflective markers) may be attached to each of the marker posts 122 of the array 114. As shown in FIG. 14G, to assemble, the markers 18 are fully seated on the posts 122. It will be appreciated that the markers 18 may be similarly affixed to the posts 66, 86 of similar arrays 56, 82 described herein.

The dilator array 114 may be attached to an initial dilator 112 for navigation by the system 10. The user may select the specific initial dilator 112 to be used with the array 114 on the software interface. When the dilator 112 and array 114 are assembled and verified, a representative image of the selected dilator 110 is overlaid on the patient's anatomical images during soft tissue dilation. Once the dilator 110 is placed, sequential dilation may be performed with non-navigated cannulas, if desired.

Turning now to FIGS. 15A-15D, embodiments of verification adapters 130 are described for verification, for example, as an alternative to an instrument 50 (e.g., disc preparation instrument or trial) or the inserter 80 with implant for verification. As best seen in FIG. 15C, each of the adapters 130 has a pointed tip 132 (e.g., a conical tip) that fits into the verification divot 70, 120 located on other array instruments 50, 110. Each type of inserter 80 mates with a specific verification adapter 130 as identified on the adapter 130. The proximal end of each adapter 130 has one or more mating features 134 (e.g., protrusions, recesses, slots) which match the corresponding implant features such that the given inserter 80 is configured to hold the matching adapter 130.

In one embodiment, the verification adapter 130 may be used to replace the instrument shaft 54 attached to an array handle 52. In this case, the adapter 130 is placed onto the array handle 52 for verification. After verification, the adapter 130 may be removed and the instrument shaft 54 is placed onto the handle 52 for its intended function. The verification adapter 130 may have a conical tip 132 that fits easily inside the verification divots 70 of the array handles 52 or any instrument with a verification divot 70, 120. The adapter 130 may be provided as an option to verify instruments 50 that do not have a convenient tip 58 for verification, such as a curved curette or osteotome.

In another embodiment, shown in FIG. 15D, the verification adapter 130 may also be used with the inserters 80. Inserter verification adapters 130 may be used for verification of the interbody inserter instruments 80 prior to use as an alternative to an implant affixed to the inserter 80. Each adapter 130 corresponds to a specific inserter 80 and implant type. The adapter 130 is placed onto the distal end of the inserter 80 to provide a pointed tip 132 for verification. After verification, the adapter 130 is removed and the desired implant is placed onto the inserter 80 for navigation.

Figure 16A:
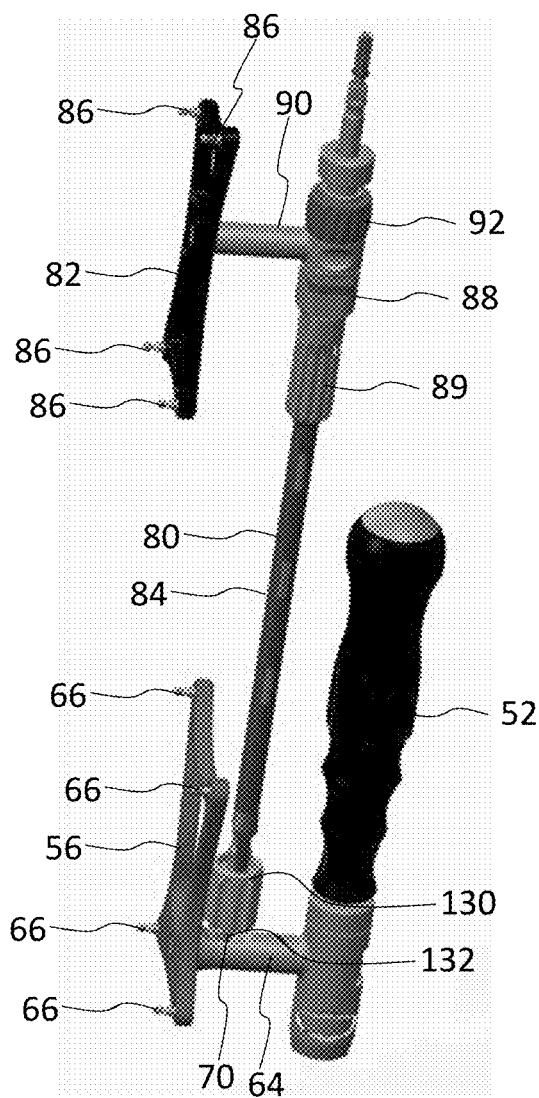
FIGS. 16A-16C show embodiments of verification of the interbody inserter.
Figure 16B:
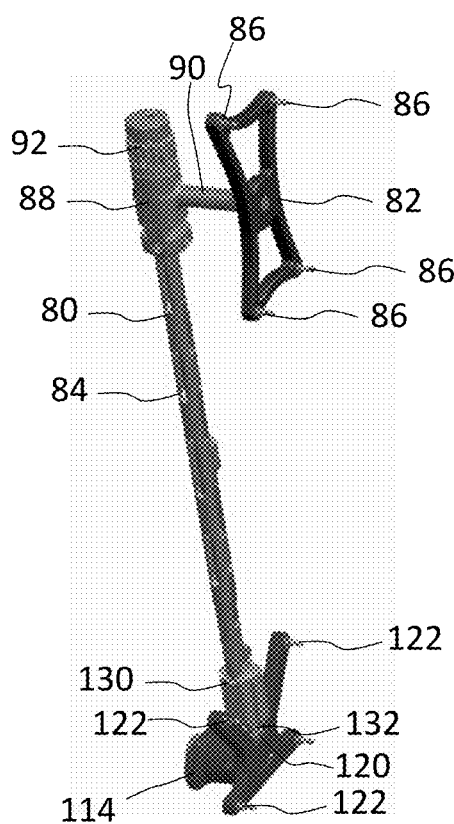
Figure 16C:
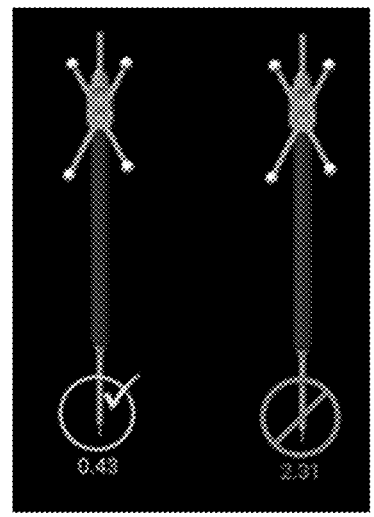

Turning to FIGS. 16A-16C, a verification procedure is described. Any instrument 50 (e.g., disc preparation instrument or trial) or inserter 80 may be placed in the verification divot 70, 120 of another array handle 52, dilator array 114, or other suitable divot for software verification. With emphasis on FIG. 16A, inserter 80 may be verified by placing the tip 132 of the verification adapter 130 into the verification divot 70 located on another array handle 52. In FIG. 16B, inserter 80 may be verified in the software by placing the tip 132 of the verification adapter 130 into the verification divot 120 located on the dilator array 114. The software verification ensures that both instruments 50, 80, 110 are visible, facing the camera 30, and held steady in a vertical position.

The central axis of each array 56, 82, 114 should be parallel to one another to complete verification.

As shown in FIG. 16C, a pop-up screen may appear on the monitor 20 (or other screen) to indicate verification progress. The navigated instruments 50, 80, 110 are pre-calibrated with dimensional information stored in the software, including optical marker location, tip location, and verification divot location. Up to six instrument shafts 54 attached to array handles 52 may be verified and navigated at one time. During verification, the predefined dimensional information is used to define instrument position. The user selects an implant family before proceeding to a verification screen. Once the implant family is selected, the location of the tip 58 of the surgical instrument 50 is known to the software. Arrays and/or integrated instrument arrays 56, 82, 114 are verified by the navigation system 10 prior to use. Verification adapters 130 may be attached to the instrument handles 52 or inserters 80 as needed. During accuracy verification (registration), the user holds the tip 58, 132 of one navigated instrument 50 or inserter 80 to the verification divot 70, 120 of another array handle 52, dilator array 114, or other suitable instrument. Both arrays 56, 82, 114 must be visible to the camera 30 and held steady in a vertical position, such that the central axis of each instrument shaft are parallel to each other. Upon completion, the verification result is displayed as success icon (e.g., green circle shown on left side of FIG. 16C) or a failure icon (e.g., red crossed circle shown on right side of FIG. 16C).

When attaching the instrument shafts 54 to the array 56, the same instrument name should be assigned to the corresponding array on the monitor 30. After verification, the instruments 50 are activated and displayed on the monitor 30. Array handles 52 and inserters 80 may only require one verification per surgery. After verification, the verification adapter 130 can be removed and the desired instrument shaft 54 or interbody spacer may be attached to an array handle 52 or interbody inserter 80, respectively. A digital representation of navigated instruments is rendered on registered patient imagery as a simplified 3D drawing depicting instrument-specific details, rather than as a generic instrument. Planned implants (which may not be navigated) are also rendered on patient imagery as simplified 3D drawings, depicting implant-specific details. Non-navigated instruments may not be rendered on patient imagery. Although specific features of verification are described herein, it will be appreciated that additional instruments or configurations may be used to verify components for the surgical procedure.

Turning now to FIGS. 17A-17B, embodiments of dynamic reference bases 140, 142 (DRBs) are shown. The dynamic reference base 140, 142 is a patient tracking device 26 including one or more tracking markers 18, which is adapted to be secured directly to the patient 2 (e.g., to the bone of the patient 2). The dynamic reference bases 140, 142 may be used to establish a fixed reference point in the optical space from which all navigation tracking is referenced. An embodiment of dynamic reference base 140 shown in FIG. 17A allows for two dynamic reference bases 140, 142 to be used at one time for a longer working distance. The dynamic reference base 140 shown in FIG. 17A may also be used as the only dynamic reference base 140, as an alternative to the dynamic reference base 142 shown in FIG. 17B.

The dynamic reference bases 140, 142 each include an array body 144 and a clamp mechanism 146. The dynamic reference bases 140, 142 attach to a rigid patient fixation device 138, such as a quattro spike, low profile quattro spike, bone clamp, rod attachment, or the like. The dynamic reference bases 140, 142 can be adjusted for positioning in the surgical space.

They dynamic reference bases 140, 142 have arrays 144 with one or more posts 148 (e.g., four posts 148) for attaching reflective markers 18 thereto. Each array 144 has a unique pattern which allows the system 10 to identify the array 144 and thereby identify the dynamic reference base 140, 142. The dynamic reference base 140 has a different array pattern than the dynamic reference base 142 so that it is uniquely identified by the system 10.

In the embodiment shown in FIG. 17A, the dynamic reference base 140 includes clamp mechanism 146, which is configured to be attached to the patient fixation post 138. The dynamic reference base 140 has a sliding mechanism 150 to clamp onto the post 138 and may be tightened by a driver (e.g., a hexalobular driver). In the embodiment shown in FIG. 17B, the dynamic reference base 142 has a clamp 146 with a thumb screw 152 that compresses a clasp around the fixation rod. The dynamic reference bases 140, 142 may be provided non-sterile and sterilized prior to use in surgery. The dynamic reference base 140 may be used alone or in conjunction with the dynamic reference base 142 for long constructs.

Figure 18A:
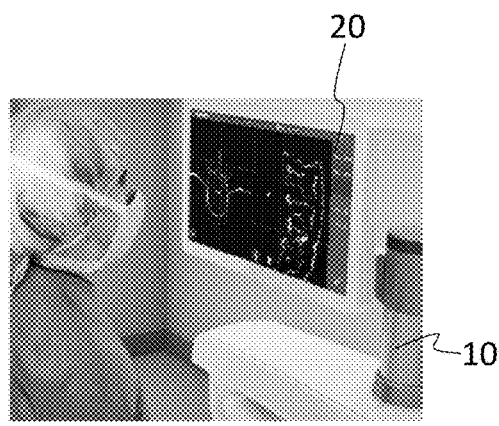
FIGS. 18A-18D show one or more steps that may be used in planning for and conducting the robot-assisted surgery.

Turning now to FIGS. 18A-18D, steps for setting up a navigated surgical procedure are shown. Prior to starting the procedure, a sterile drape 28 is placed over the robotic arm 14, monitor 20, and front portion of the base station 16. Passive markers 18 are added to the arrays 56, 82, 114, 144 of all navigated instruments and devices 50, 80, 110, 140, 142. As shown in FIG. 18A, the surgeon can use planning software to determine the location of interbody implants and instruments on patient images 20. Planning may be performed before image registration for preoperative imaging workflow or after image registration for intraoperative imaging workflow or 2D imaging workflow. Instrument planning allows the surgeon to plan interbody devices (or screws) with navigated instruments 50, 80, 110 by pressing on the foot pedal or confirming on the touch-screen monitor 20 after image registration. The surgeon can plan on the touch-screen monitor 20 as well as on the tablet with preoperative imaging. The implant is selected in the software and moved to the desired location on the patient images.

Figure 18B:
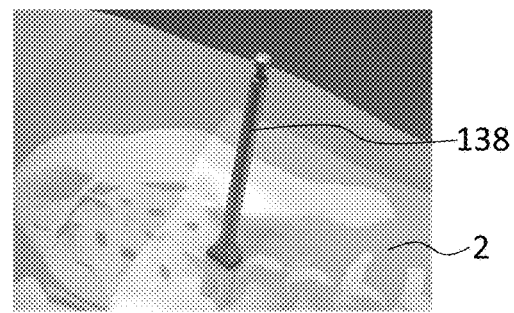
Figure 18C:
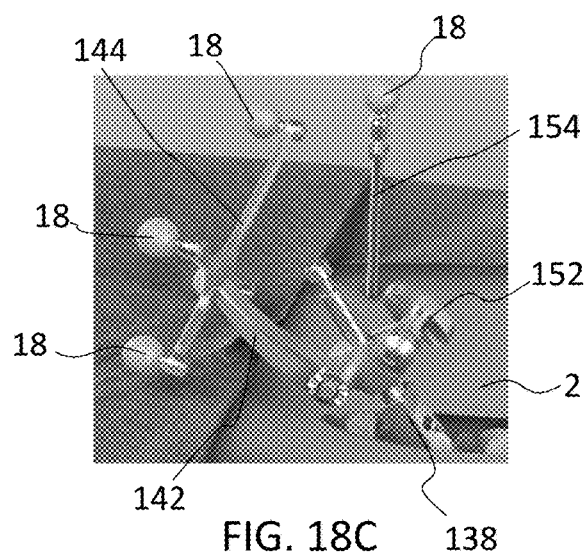

As shown in FIG. 18B, once the patient 2 has been prepped and the surgeon is ready to begin, a patient fixation post 138 is secured to the patient's bony anatomy in proximity to the surgical site. As shown in FIG. 18C, a dynamic reference base 140, 142 may be attached to the patient fixation post 138. In addition, a separate surveillance marker 154 may also be secured to the patient's bony anatomy in proximity to the surgical site. The surveillance marker 154 may include a single tracking marker 18 and may be used to provide additional verification that the dynamic reference base 140, 142 does not move during the procedure.

Figure 18D:
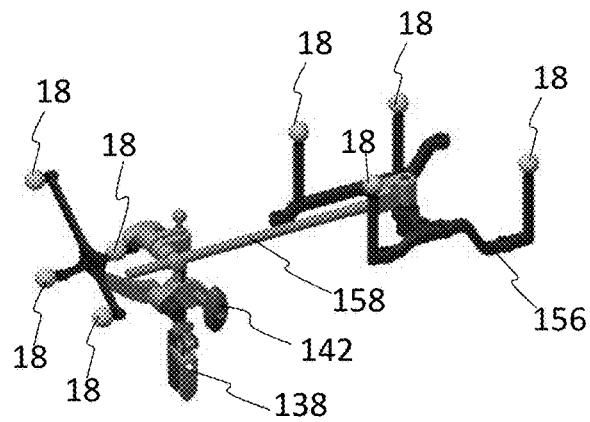

A specific anatomical position is first registered on the patient 2 in reference to a known coordinate frame in order to track its location. As shown in FIG. 18D, this may be accomplished by rigidly affixing the dynamic reference base 140, 142 and intra-op registration fixture 156, which contains both CT fiducials and passive markers 18, to the patient attachment instrument 138 (e.g., applicable for the intraoperative CT imaging modality). The dynamic reference base 140, 142 is rigidly fixed to the patient attachment instrument 138. The dynamic reference base 140, 142 is placed in a location that can be easily seen by the camera 30. The intra-op registration fixture 156 is clamped to the post of the patient attachment instrument 138 with a pivoting arm 158.

The pivoting arm 158 may have six degrees of freedom so that the fixture can be positioned directly over the surgical site.

Figure 19A:
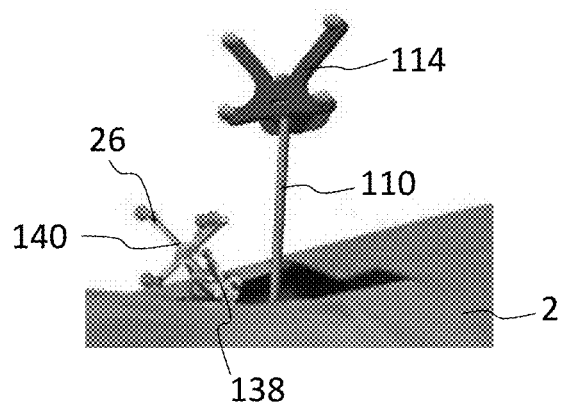
FIGS. 19A-19C show one or more steps that may be used in performing the robot-assisted surgery.
Figure 19B:
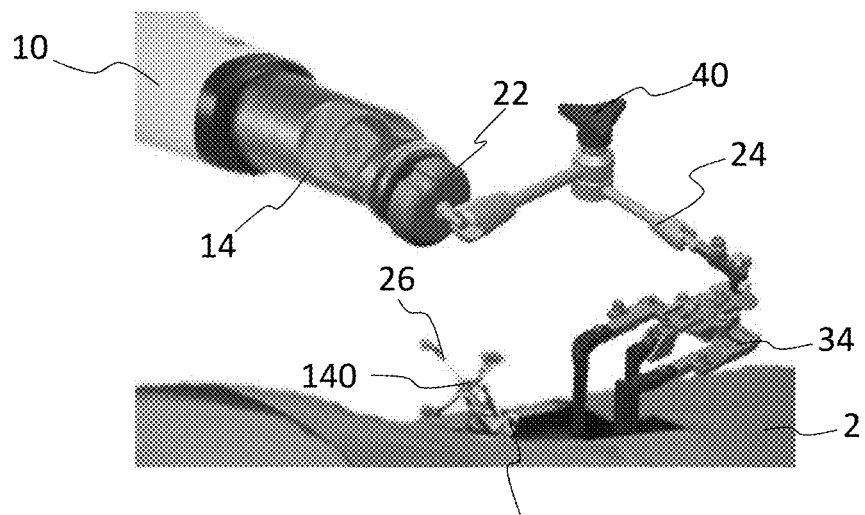
Figure 19C:
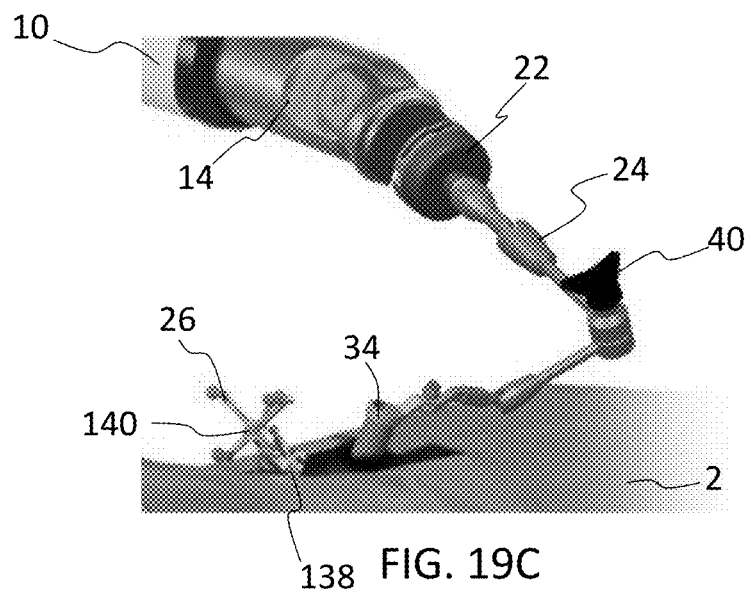

Turning now to FIGS. 19A-19C, one or more steps for performing the navigated surgical procedure are shown. As shown in FIG. 19A, if desired, the starting position and trajectory of the access instrument 34 (e.g., retractor shown in FIG. 19B or port system shown in FIG. 19C) may be established by navigating the dilator 110. The dilatory array 114 may be verified by the system 10. The initial dilator 112 may be navigated to locate the access trajectory. The dilator array 114 may be removed for tissue dilatation. For example, sequential dilation using dilators (cannulas) of increasing size may be performed by the surgeon. The access instrument 34 may be positioned over the dilators. The articulating arm 24 may be attached to the access instrument 34 and the end-effector 22, which is coupled to the robot arm 14. The locking knob 40 may be tightened to secure the articulating arm 24. Once the access instrument 34 is positioned, any of the navigable instruments 50 and inserters 80 may be utilized as described herein to install the interbody implant.

Turning now to FIGS. 20A-20G, examples of software user interfaces that may be utilized for instrument planning, setup and access, and/or throughout navigation of the surgical procedure are provided. Instruments 50, 80, 110 may be navigated freehand during the surgical procedure for preparation and placement of interbody fusion devices. Screws may be placed before or after interbody spacers using various workflows. The position of the instruments 50, 80, 110 are tracked by the camera 30. The surgeon has the same tactile feel of the disc space anatomy and the surgical instruments 50, 80, 110 as in a standard surgery. Instruments 50 including trials, cup curettes, ring curettes, cobb elevators, elevators, osteotomes, rasps, rakes, scrapers, sizers/shavers, paddle distractors, and trials, may be used according to standard surgical techniques to place interbody spacers. The position of the navigable instruments 50, 80, 110 is monitored in real time. The surgeon manually operates the instruments 50, 80, 110 and determines the correct placement and positioning. Surgical instruments 50, 80, 110 may be used through the attached access instrument 34 (e.g., retractor or port), if desired.

The robotic software user interfaces are configured to aid the surgeon and staff through a typical procedure. Tabs on the screen 20 may represent each step of the process, as follows: (1) workflow step 162 allows the user to select the implant set and general location of implant placement; (2) verify step 164 allows the user to verify the navigation instruments, for example, to ensure instruments were not damaged since the last use; (3) image step 166 allows the user to import and select the patient images; (4) plan step 168 allows the user to plan implant placement on the patient's medical images; and (5) navigate step 170 shows instrument and implant location on the patient's medical images.

Figure 20A:
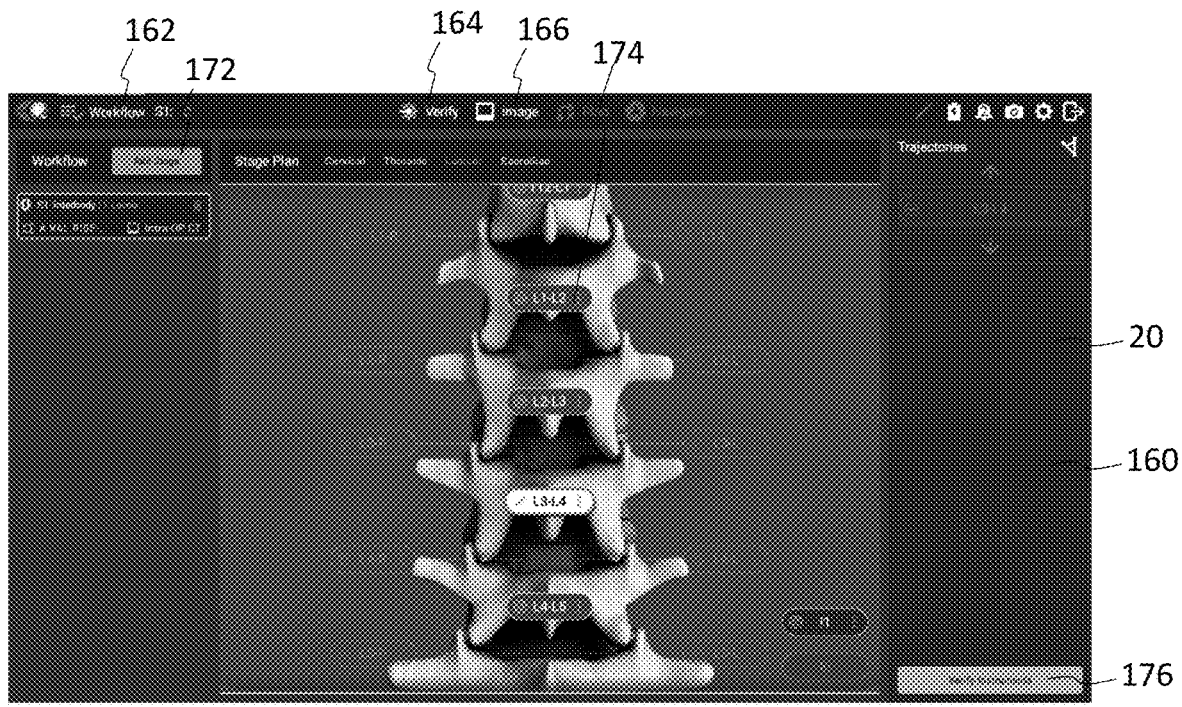
FIGS. 20A-20G depict examples of software user interfaces that may be utilized for instrument planning, setup and access, and/or throughout navigation of the surgical procedure.

Referring to FIG. 20A, instrument planning in the workflow step 162 may begin with a screen view 160 with a simulated anatomical view of the spine. In the workflow tab 162, the desired stage of the procedure (e.g., interbody or screw placement) may be selected in the desired order of operation (e.g., interbody placed first). For each stage, the imaging modality, interbody implant system, and desired interbody level on the anatomical model may be selected. Stages may be added to the workflow by clicking the "Add Stage" button 172 to add a stage to the case. The spinal levels may be selected, for example, by double-clicking on the spinal level indicator circles or bubbles 174 to select or de-select the spinal level for planning. The "Verify Instruments" button 176 may be selected to proceed to advance to the next tab.

Any navigable instrument 50, 80, 110 can be used for instrument planning. Instrument planning refers to creating an implant plan by aligning the trajectory of a navigated instrument 50, 80, 110 to the desired implant trajectory and confirming this trajectory through a user input. The instrument planning functionality allows the user to select whether the implant plan is created at the tip 58 of the instrument 50, or at some distance from its tip 58 along its trajectory. The user can select the type and dimensions of the planned implant to best fit the image of patient anatomy. The user navigates instruments 50, 80, 110 to the desired location and drops to the implant onto patient images in the software.

Figure 20B:
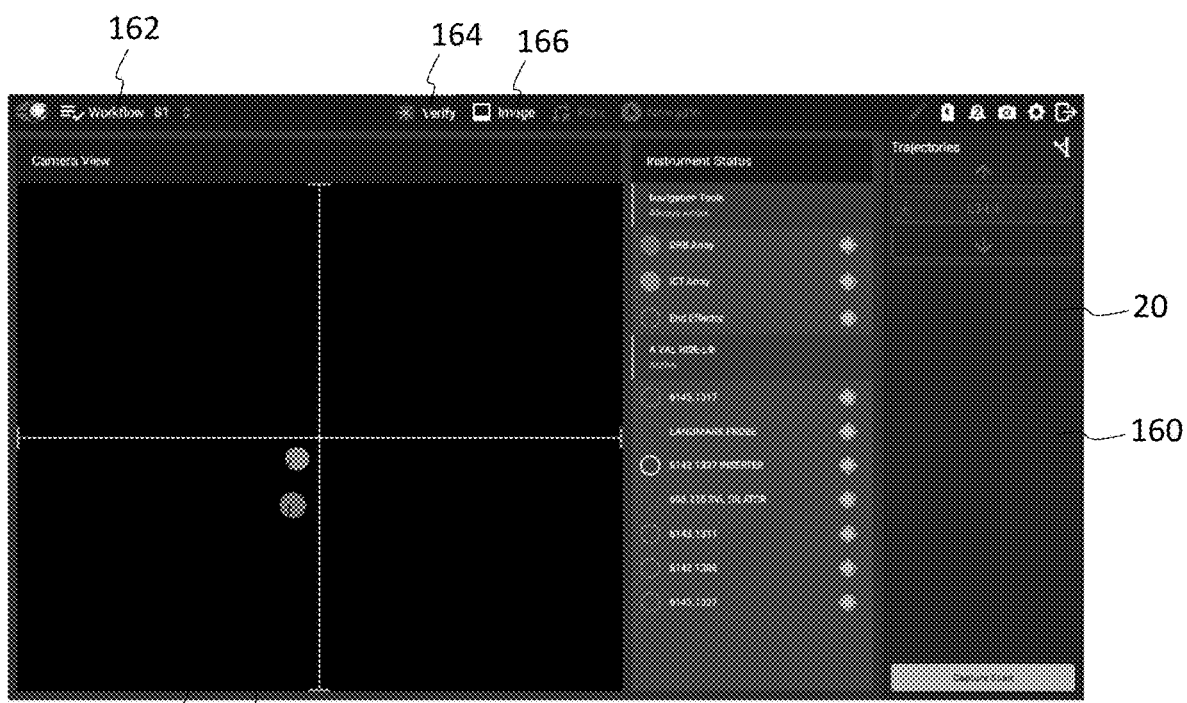

Referring to FIG. 20B, the verify tab 164 displays navigation details including visibility, location and verification status of the instruments 50, 80, 110 selected on the workflow tab 162. Verification may be used, for example, to ensure all instruments 50, 80, 110 have not been damaged during handling. All instruments 50, 80, 110 with arrays 56, 82, 114 may be verified prior to use, either with a verification adapter 130, instrument 50, implant, or dilator 110, as appropriate. The verify tab 164 may show a camera view and instrument status. The camera view is a real-time view from the perspective of the camera 30 with one or more color circles 178 indicating instrument location. A solid colored circle 178 may indicate that the instrument 50, 80, 110 is visible by the camera 30, while a hollow circle may indicate that it is not visible. The colored circle 178 may grow larger as the instrument 50, 80, 110 is moved closer to the physical camera 30 and smaller as it moves away from the camera 30, for example. The ideal distance from the camera 30 is approximately 2 meters or 6 feet, but it will be appreciated that the distances may vary. The instrument status may list each instrument 50, 80, 110 and its verification status, with corresponding color circles to identify each instrument 50, 80, 110. The verification status symbols may include a green marker indicating successful verification and a red marker indicating failed verification. The icons for the verify tab 164 may include a back arrow indicating a return to workflow tab 162 and a load scan button for clicking to proceed to the next image tab 166.

Figure 20C:
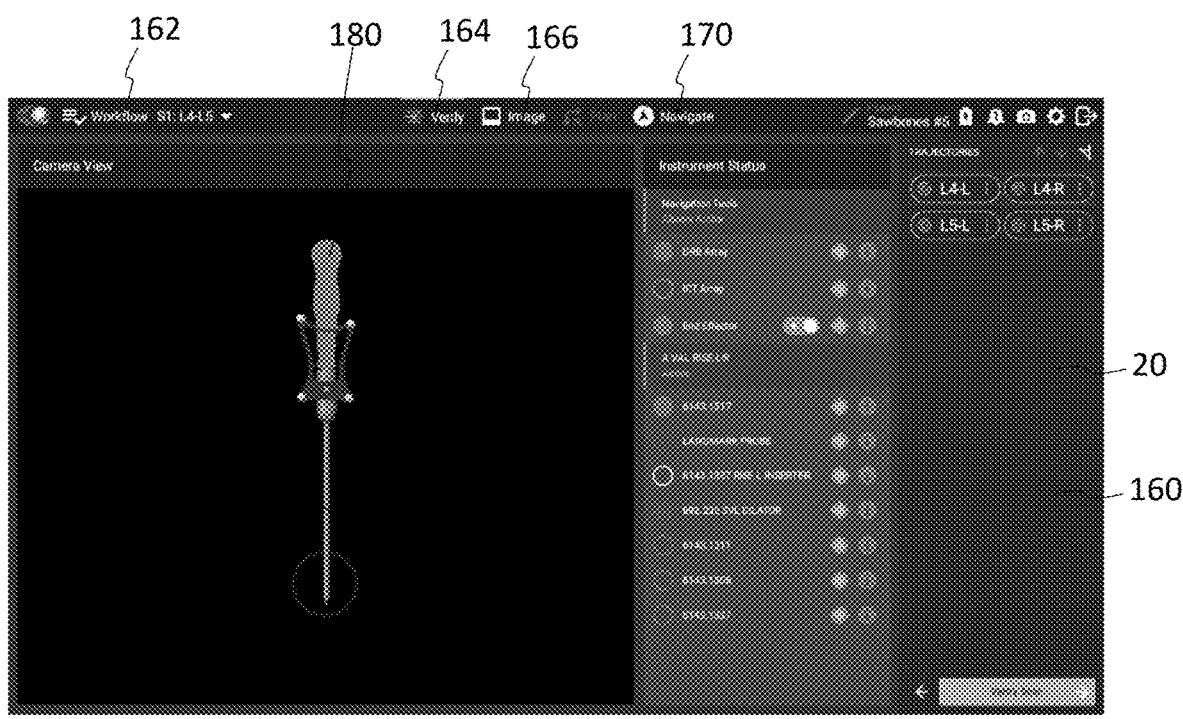

Referring to FIG. 20C, arrays 56, 82, 114 are verified by the navigation system 10 to ensure they have not been damaged during handling, cleaning, or sterilization. The camera 30 detects the unique pattern of reflective markers 18 affixed to the arrays 56, 82, 114. Each array 56, 82, 114 must be verified prior to use, by attaching the instrument shaft 54, verification adapter 130, implant (for inserter 80), or dilator 112 (for dilator array 114), to the array handle 52 or inserter 80 and placing the tip of the assembly into the verification divot 70, 120 of another array handle 52 or the dilator array 114. After verification, the verification adapter 130 is removed (if used) and the desired instrument shaft 54 or interbody spacer is attached to the array handle 52 or inserter 80, respectively. When attaching an instrument shaft 54 to an array handle 52, the same instrument name should be assigned to the corresponding array in the software. At this point, the virtual instrument or instruments 180 are activated and displayed on the monitor 20. Once verification is complete, verification status is indicated on the screen 20. If there is an error, the tip error may be displayed in mm. As shown in FIG. 16C, the screen view 160 may indicate if verification has failed (e.g., a red crossed circle may be displayed), and verification may be repeated until it is successful (e.g., a green circle may be displayed). When all instruments are successfully verified, the "Load Scan" button may be selected to advance to the next tab.

Figure 20D:
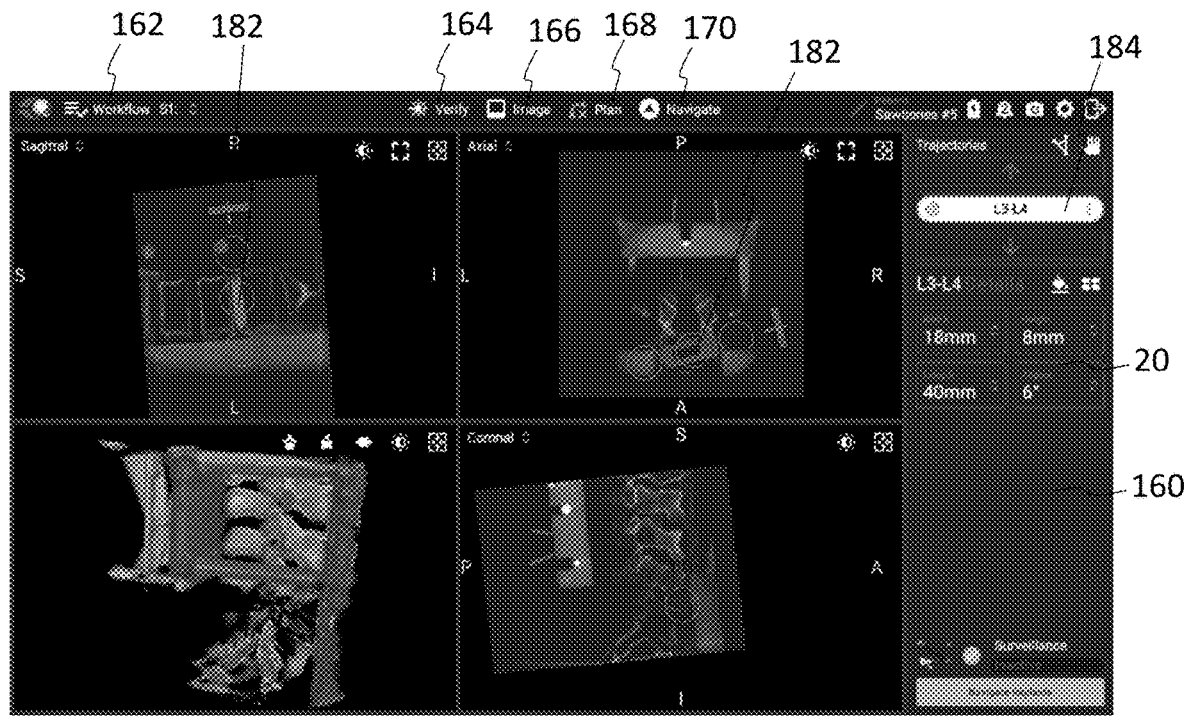
Figure 20E:
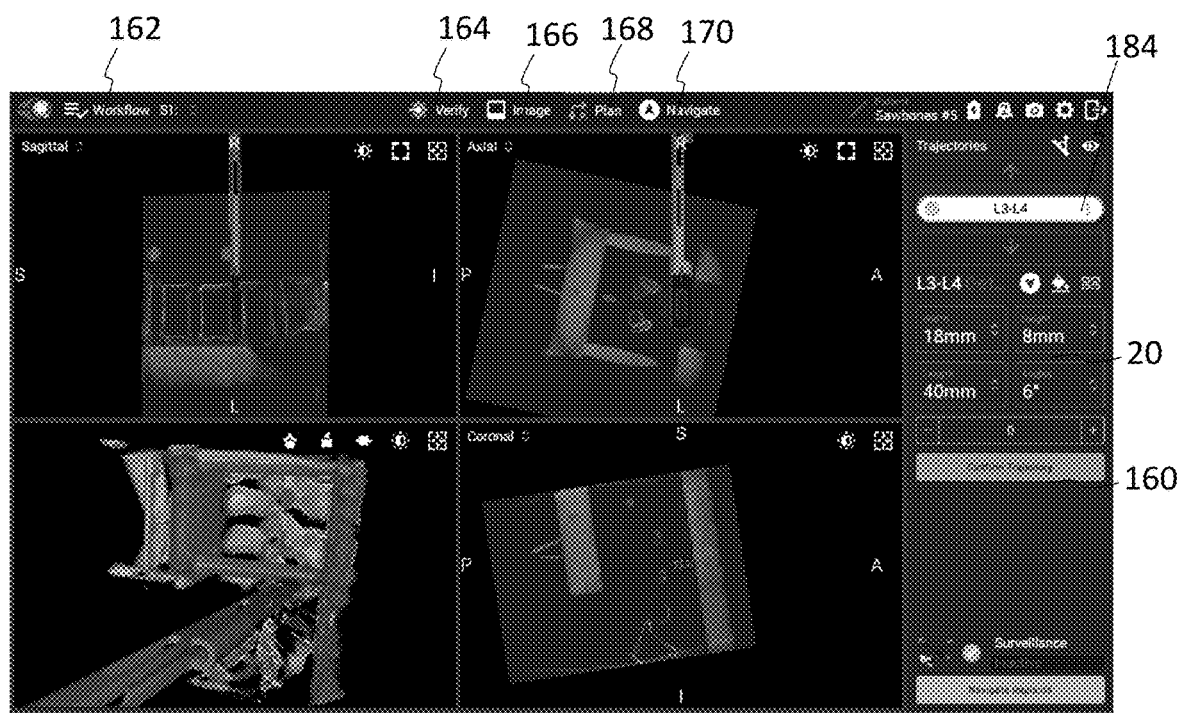

Turning to FIGS. 20D and 20E, the plan step 168 allows for optional planning for interbody implant placement. The plan tab 168 allows the user to plan placement of all virtual interbody implants 182 overlaid on the screen view 160 of the patient images. Implants may be preloaded on the right panel of the screen 160, based on selections made in the workflow tab 162. An implant plan may be created by dragging and dropping the desired implant 182 on the patient image, or by navigating an instrument 50, 80, 110 to the desired location and dropping an implant 182 in that location on the patient image. The implant position and size may be adjusted on the planning tab 168.

In FIG. 20D, the desired implant label may be selected on the right panel of the screen 20 and dragged onto the image. Once aligned, the planned implant 182 may be released to drop it onto the image 160. The active implant 182 may be highlighted on the right panel during planning. When selected, the icon may switch to the hand icon. In FIG. 20E, the instrument planning icon on the right panel of the screen 20 may be selected to activate instrument planning. When selected, the icon may switch to the visible icon. The desired implant label may be selected on the right panel of the screen 20. Using a verified instrument, the desired trajectory may be navigated on the patient images. The foot pedal may be pressed or the confirm trajectory button may be selected to save the desired implant location. Once the planned implant 182 is dropped on the image 160, the implant planning features may be used to adjust implant location by dragging the implant image 182 on the touch screen 20. The specific implant size may be selected (e.g., width, length, height, lordosis) on the right panel of the screen 20. A blue icon may confirm the trajectory with a click to drop the implant 182 on the patient images 160. A hand symbol may indicate the instrument planning icon with a click to transition to instrument planning mode. An eye symbol may indicate a visible icon to indicate that the user is in the instrument planning mode. The level bubble indicator 184 may indicate the active implant being planned and the spinal level.

Figure 20F:
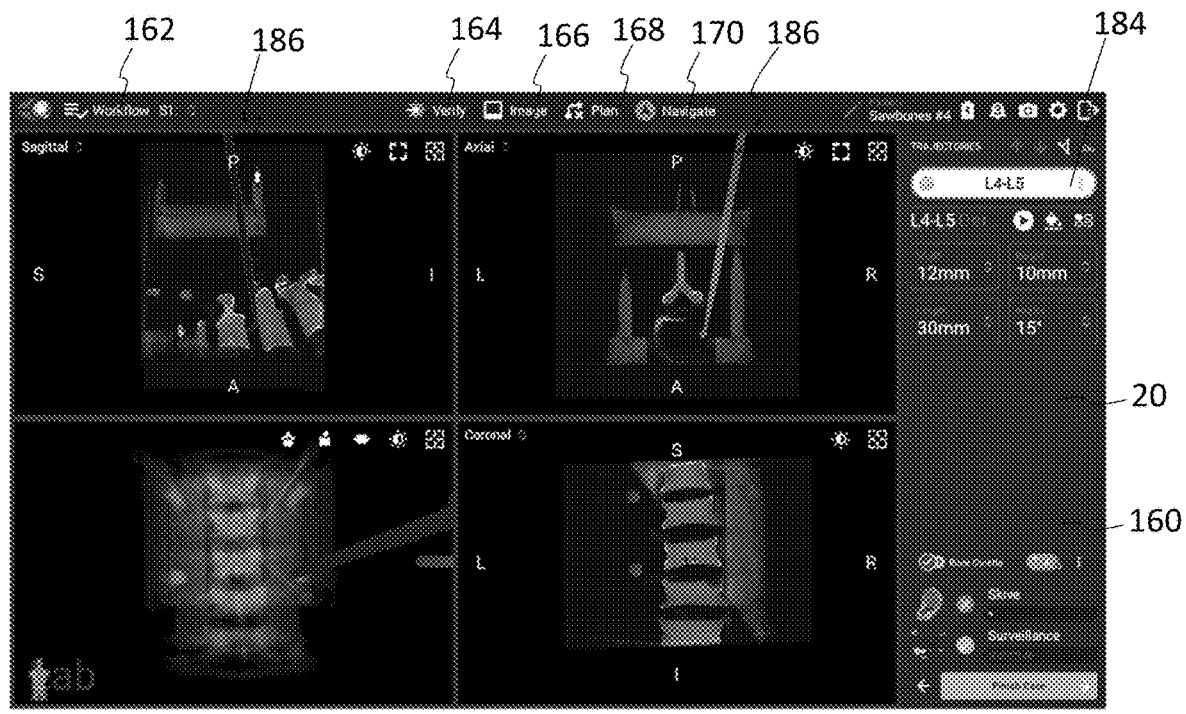
Figure 20G:
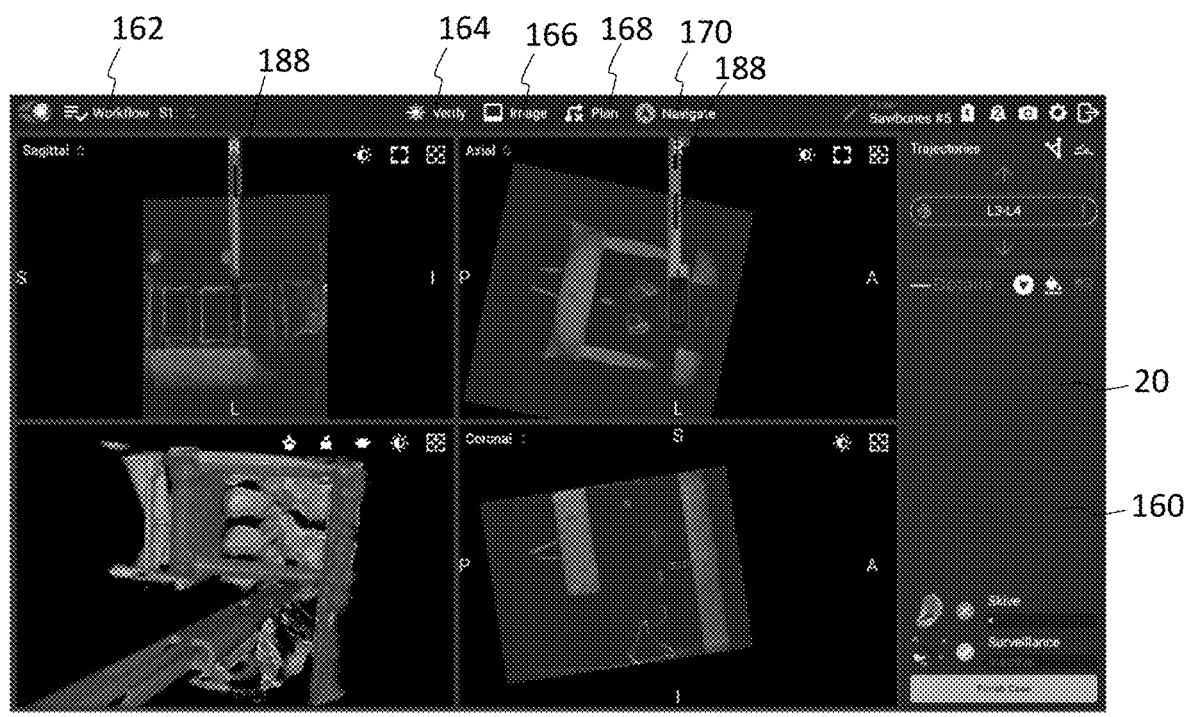

Turning to FIGS. 20F and 20G, the navigation tab 170 may allow for disc preparation, trialing, and interbody placement. Prior to navigation, the motion lock end effector 22 can be used to attach the access instrument 34 (e.g., retractor or access port) for surgery if desired. Following draping, the user can move the robotic arm 14, for example, under wrist mode by pressing the bracelet or the foot pedal. The user moves the arm 14 manually to a desired position within reach of the surgical area, close to the surgical site. The sterile motion lock end effector 22 is then attached to the robotic arm 14 over the drape 28. This locks motion of the robotic arm 14. The retractor or port 34 may be attached to the articulating arm 24 to rigidly fix its position and orientation for the duration of the procedure, providing an access corridor to the spine. The articulating arm 24 and retractor or ports 34 may not be displayed on the monitor 20. The articulating arm 24 may be secured to the motion lock end effector 22 by pressing the release button 36 and attaching it. The retractor or port 34 may be attached to the attachment mount 38 of the articulating arm 24. If desired, the dilator array 114 may be attached to the initial dilator 112 to navigate to the starting position and trajectory of the retractor or port 34. Once the desired position is established, the articulating arm 24 on the desired retractor or port 34 may be connected to the attachment mount 38. The locking knob 40 is secured to lock the articulating arm 24. Once the articulating arm 24 and retractor or port 34 are in the desired position, the surgical procedure may be performed.

In FIG. 20F, after assembling the desired instruments 50 (e.g., disc preparation instruments and trials) to an array handle 52 and instrument verification is performed, the instrument 50 may be assigned to the given array 56 by clicking the "Array Identifier" button. The correct index position 74 may be identified by clicking the "Array Index Identifier" button. Once the array 56 has been verified, disc preparation and trial instruments 50 may be switched out during the procedure but the new instrument 50 must be re-assigned and the array index position 74 adjusted accordingly in order for the instrument 50 to be correctly displayed for navigation. An anatomical landmark check may be performed to ensure that the instrument 50 is not damaged and the instrument settings are correctly set. Disc preparation and trialing may be performed using the navigated instrument assembly 186 displayed on the screen 20.

In FIG. 20G, the interbody implant may be placed. The trial may be assigned to the array handle 52 by clicking the "Array Identifier" button. The correct index position 74 may be assigned by clicking the "Array Index Identifier" button. The trial may be navigated to the desired location. The trial may be inserted into the disc space. This may be repeated for various trials until the desired implant size is determined. The inserter 80 may be selected corresponding to the interbody device being used. Instrument verification may be performed using the verification adapter 130 or the implant. The desired interbody implant is attached to the inserter 80. The implant size may be selected (e.g., width, length, lordosis) on the right panel of the screen 20. The interbody implant is navigated to the desired location and the virtual inserter and implant 188 are displayed on the patient images 160. The implant is inserted into the disc space based on the navigational information displayed, for example, on monitor 20. For expandable spacers, the corresponding torque-limiting driver may be used to expand the device. The interbody software module may provide for navigation of access, preparation and/or placement of the interbody fusion devices.

Turning now to FIGS. 21A-21H, another embodiment of a navigable dilator instrument or dilator 210 is described in further detail. Navigable dilator 210 may be similar to dilator 110 shown in FIGS. 14A-14G. The navigable dilator 210 may include an initial dilator 212 and a dilator holder or dilator array 214 configured to be tracked by the robotic navigation system 10. The dilator array 214 may include a unique array pattern, a cavity or attachment window 216, a release button 218, and a verification reference feature 220. Similar to array 114, array 214 may have one or more posts 222 (e.g., four posts 222) for attaching tracking markers 18 thereto.

In a minimally invasive spine surgery, sequential dilation may be used to gain access from an incision to a surgical target, typically the intervertebral disc space. Fluoroscopy (x-ray) may be used to target the incision, disc space, and retractor location. Fluoroscopy is also used to ensure that the dilator is inserted along the desired trajectory to access the disc space. The initial dilator is inserted into the incision and traversed through soft tissue while the trajectory is confirmed with multiple x-ray images. The surgical site may be sequentially dilated by placing larger cannulas over the initial dilator. The retractor may be inserted once the site is sufficiently dilated. The retractor provides a working corridor to insert osteotomy, discectomy, and interbody instruments into the disc space. However, the patient, surgeon, and surgical staff may be exposed to potentially harmful radiation due to the amount of fluoroscopy required for this method of dilation. In addition, complications may arise from an inaccurately placed instrument. Finally, this method may be time consuming which reduces surgical efficiency and patient safety.

With the robotic navigation system 10, the initial dilator 212 may be navigated by the system 10 while greatly reducing or eliminating the need for intraoperative fluoroscopy, increasing accuracy, and/or increasing intraoperative efficiency. The system allows for tracking full rigid body motion of the surgically navigated dilator 210 through surgical robotic navigation technology. With the surgical robotic navigation, the instruments 50, 80, 110, 210 may be tracked through optical or electromagnetic position sensors 18, the associated computer-aided design (CAD) model may be displayed relative to anatomical landmarks, and/or the instruments 50, 80, 110, 210 may be guided to planned positions using the robotic system 10.

Surgical navigation or robotic navigation systems may track the full rigid body motion of an instrument 50, 80, 110, 210 by measuring the position of an array 56, 82, 114, 214 of optical or electromagnetic markers 18 relative to one another. A model may be mapped to these measured marker locations, oriented in 3D space, and displayed relative to anatomical images for the surgeon. One way to ensure the orientation of the tracking array 56, 82, 114, 214 is to rigidly mount the array to the tool. For the dilators 110, 210, however, it may not be possible to rigidly and permanently mount the array 114, 214 to the tool.

Sequential dilation includes using dilators of increasing diameter to be subsequently inserted into the soft tissue. To maintain the target trajectory and prevent tissue damage, sequential dilation may be accomplished by placing each larger dilator concentrically around a previously inserted dilator. The initial dilator 112, 212 may be placed with the assistance of robotic navigation. The removable tracking array 114, 214 may be removed. Then, subsequent dilators may be inserted. The array 114, 214 may be re-attached to track the position of the dilators while placing the retractor or other access instrument 34. In this way, the removable array 114, 214 acts as a navigated dilator holder. Through this method, the initial dilator 112, 212 may be directly navigated and the retractor or other access instrument 34 may be indirectly navigated. Once the desired trajectory and depth are determined through navigation, the retractor or other access instrument 34 can be rigidly fixed in place and the dilators and tracking array 114, 214 may be removed.

In addition to the dilator and retractor placement, there may be other benefits to a navigated dilator holder or array 114, 214. Dilator sizes and styles may be unique to a particular retractor system. A universal navigated dilator holder 114, 214 which accommodates various sizes and styles of initial dilators 112, 212 may help to reduce set complexity, improve intraoperative efficiency, and/or improve flexibility for accommodating various surgeon preferences. When coupled to the initial dilator 112, 212, the device 114, 214 may also serve as a navigated probing tool for identifying landmarks, measuring depths, and/or verifying trajectories in the anatomy. The adaptability of the navigated dilator holder 114, 214 may allow it to be attached to instruments or instrument adapters and used as a reference array for verifying the tracking accuracy of other instruments and instrument arrays.

With reference to FIGS. 21A-21C, one embodiment includes the navigable dilator holder or removable array 214 rigidly attached to the initial dilator 212 with a mechanism capable of quickly attaching to and detaching from the initial dilator 212. The navigated dilator holder 214 is able to attach to and detach from initial dilator 212, with or without subsequent larger diameter dilators present. In addition, the array 214 may repeatedly attach to and detach from initial dilators 212 or other verification instruments to ensure positional accuracy of the distal tip of the instrument. The verification reference point 220 may be used to verify other navigated instruments. The initial dilators 212 may be placed with a k-wire attached, if desired. The navigated dilator holder 214 may contain a hole or slot 224 for the k-wire to avoid interference with the inserted k-wire.

As best seen in FIG. 21C, the rigid body of the array 214 may include a v-block 226 and a depth stop 228 to accurately locate an axisymmetric instrument, such as initial dilator 212. In this embodiment, the dilator 212 may be rigidly located with respect to the array 214 via a spring-loaded mechanism 230. The initial dilator 212 may be inserted into the cavity 216 in the rigid body containing the v-block 226, depth stop 228, and spring-loaded mechanism 230. The array 214 is rigidly attached to the dilator 212 with the spring-loaded quick release button 218 for attaching the array 214 and accurately locating the initial dilator 212. If the spring-loaded mechanism 230 is compressed, such as through the push of the button 218, the size of the cavity 216 is increased allowing easy insertion and removal of the instrument 212. When the spring-loaded mechanism 230 is decompressed, such as through releasing force on the push button 218, the size of the cavity 216 decreases and the inserted dilator 212 is centered in the v-block 226 through a transverse force provided by a force applicator 232 coupled to the spring-loaded mechanism 230.

In another embodiment shown in FIGS. 21D-21H, the transverse force is provided by a screw-based mechanism 234. The v-block 226 is screw-driven by a screw 234 or other suitable mechanism for attaching the array 214 and accurately locating the initial dilator 212. In each embodiment, the variability of cavity size and self-centering nature of the v-block 226 allows for insertion of a variety of dilator sizes and styles. In addition, each embodiment may include the slot 224 for insertion of k-wires with or without the dilators attached. The depth stop 228 also provides repeated insertion depth of the dilator 212 in the attachment mechanism, which enables accurate tracking and prevents interference with larger diameter subsequent dilators. The initial dilator 212 may be tracked through robotic navigation methods, which reduces or eliminates the need for fluoroscopy while dilating the surgical site and placing the retractor or access instrument 34. The tracked array 214 may be quickly and repeatedly attached to the dilator 212 enabling subsequent dilation without interference with subsequent dilators or anatomy. The tracked array 214 accommodates various initial dilator sizes and styles which may reduce set complexity, improve intraoperative efficiency, and/or improve flexibility for accommodating various surgeon preferences. The tracked array 214 may be used as a reference array for verifying the accuracy of other instruments or instrument arrays.

Figure 22A:
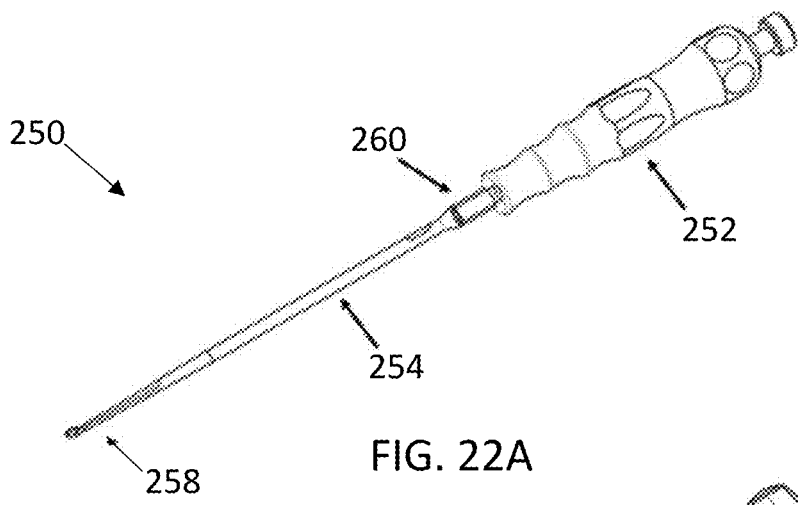
FIGS. 22A-22C depict embodiments of navigable instruments with detachable replacement tools and/or instrument tips.
Figure 22B:
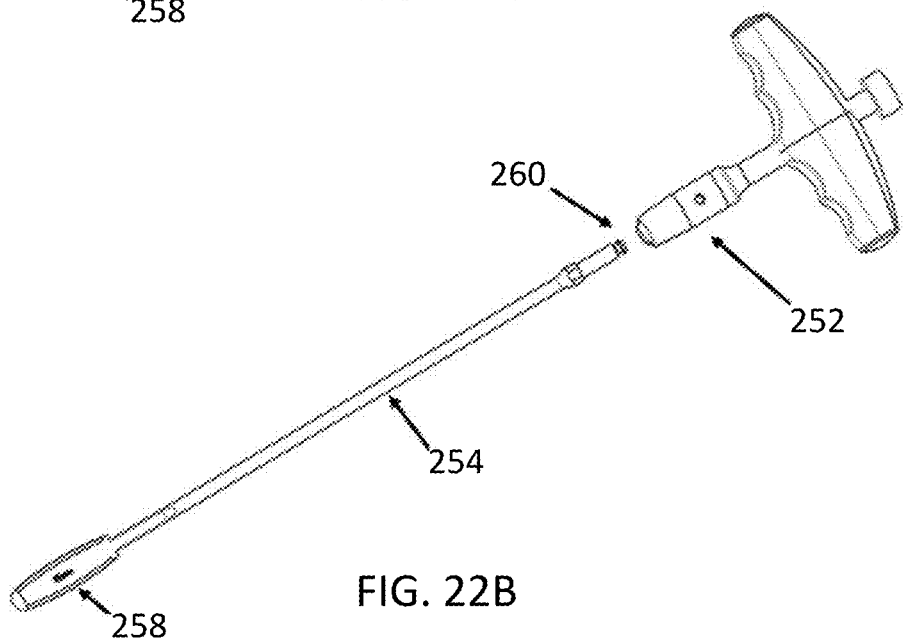
Figure 22C:
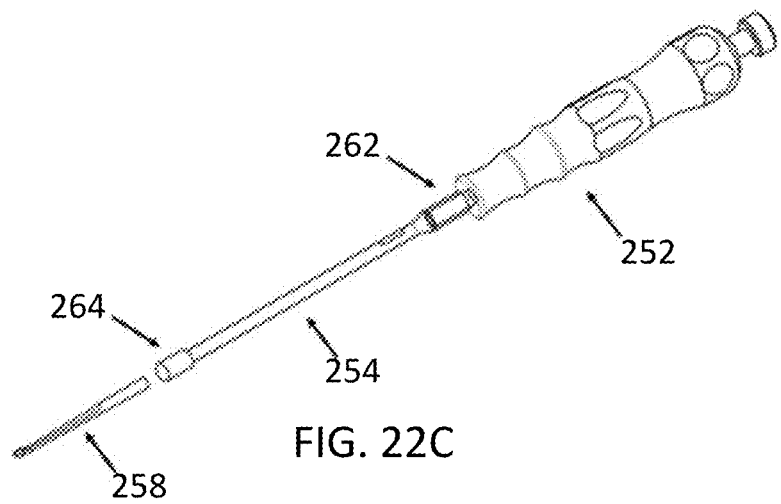

Turning now to FIGS. 22A-22C, embodiments of instruments 250 with a removable shaft 254 and/or removable tip 258 for are shown. Instrument 250 may be similar to the instruments 50 shown in FIGS. 6A-9F. Although markers 18 are not shown, it will be appreciated that suitable arrays 56 and markers 18 may be included on these instruments 250, if desired. Often during medical procedures, instruments may undergo stresses that lead to wear and occasionally to damage. Once worn or damaged, tools require replacement, and due to the one-piece or uni-body construction of the tools, replacement carries a high cost and a large amount of space used in the operating room to store cases containing replacement instruments. Accordingly, in some embodiments, the instruments 250 may include removable shafts 254 and/or removable tips 258. Replaceable tips 258 may be advantageous as less full-size equipment is needed in the operating room with each tool only needing one shaft 254 and/or a supply of separate tips 258.

The removable shafts 254 and/or removable tips 258 may offer a reduction of size and number of instruments and graphics cases required in the operating room. In addition, operating room efficiency may be improved by the decreasing the number and size of instruments on the back table and Mayo stand. In addition, the removable shafts 254 and/or removable tips 258 enables replacement of the worn component (e.g., tool tip) rather than the entire instrument which decreases cost of maintenance and repair. As less handle and shaft components are required, the cost of manufacturing each instrument set is also decreased. Also, the modularity may enable low-cost, surgeon-specific instrumentation as simplified custom tool tips may be created to fit a common shaft-handle assembly.

In one embodiment shown in FIG. 22B, the instrument 250 includes a modular two-piece instrument design. The handle 252 may include a quick-release mechanism 260 that mates to an instrument shaft 254 with an integrated tip 258. The multi-piece instruments 250 may be found in sizing applications where many incremental sizes are needed in the instrument set (e.g., sizers, shavers, paddle distractors, trials, etc.). The modular set may decrease the cost and size of the instrument set.

Over the course of time, tools may be damaged in surgery or worn out from repetitious uses over multiple cases. When the instrument requires service due to wear or damage, the entire one-piece instrument must be replaced. Even in the case of two-piece instruments, the shaft-tip construct may need to be replaced. In one embodiment shown in FIG. 22C, the tool tip 258 may be replaced. For example, the instrument 250 may include a handle 252, a shaft 254 coupled to the handle at connection 262, and a replaceable tool tip 258 coupled to the shaft 254 at connection 264. The connection 262 may be a rigid, permanent connection between the shaft 254 and handle 252 or may also be modular.

As shown in FIG. 22C, the connection 264 may provide for repeatable and durable attachment of the tool tips 258 to the shaft 254 of the instrument 250. The connection 264 may allow for temporary retention, rotational constraint, and/or axial "pull-out" constraint of the tip 258. Temporary retention of the tool tip 258 in the instrument shaft 254 prevents the tip 258 from accidently falling out under gravitational forces when the tip 258 is replaced. Rotational constraint preserves the position of the tool tip 258 with respect to the handle 252 under typical torsional loading conditions in a surgical environment. Similarly, axial constraint preserves the axial position of the tool tip 258 and prevents unintentional release of the tool tip 258 under typical axial loading conditions in a surgical environment.

Temporary retention of the tool tip 258 may be accomplished through one or more mechanisms including but not limited to magnetism, friction, and/or clamping force. In one embodiment with a magnetic-ferromagnetic connection 264, the proximal end of the tool tip 258 contains a magnet that mates to a ferromagnetic feature of a release mechanism on the distal end or interior cavity of the instrument shaft 254. In another embodiment with a ferromagnetic-magnetic connection 264, the proximal end of the tool tip 258 may contain a ferromagnetic feature that mates to a magnetic feature of the release mechanism on the distal end or interior cavity of the instrument shaft 254. In yet another embodiment with a magnetic-magnetic connection 264, the proximal end of the tool tip 258 may contain a magnet that mates to a magnetic feature of the release mechanism on the distal end or interior cavity of the instrument shaft 254.

According to another embodiment, the proximal end of the tool tip 258 may contain a tapered male feature that mates to a tapered female feature of a release mechanism on the distal end or interior cavity of the instrument shaft 254. In yet another embodiment, the proximal end of the tool tip 258 may contain a tapered female feature that mates to a tapered male feature of the release mechanism on the distal end or interior cavity of the instrument shaft 254. The tapered features may include, but are not limited to, tapered three-dimensional geometries such as conical surfaces, tapered cylinders, and tapered prisms. The function of these male-female pairs of tapered surfaces is to create an interference fit between assembled components such that the components are temporarily fastened via friction but can be disassembled with sufficient axial force.

According to another embodiment, the release mechanism on the distal end or interior cavity of the instrument shaft 254 may contain an O-ring or other compressible flexure that depresses and applies a clamping force when the proximal end of the mating tool tip 258 is assembled. In another embodiment, this compressible flexure may be a linear spring. In other embodiments, the clamping force may be provided by a latch-hook mechanism or ball plunger and detent mechanism.

According to another embodiment, rotational constraint of the tool tip 258 may be accomplished through a variety of mechanisms, including but not limited to, three-dimensional screw drive features or threads. Screw drive features may be used to provide rotational constraint in fasteners, such as screws or bolts, which function in male-female pairs. In one embodiment, the male feature may be located on the proximal end of the tool tip 258 and the female feature may be located in the release mechanism 264 on the distal end or interior cavity of the instrument shaft 254. In another embodiment, the female feature may be located on the proximal end of the tool tip 258 and the male feature 254 may be located in the release mechanism 264 on the distal end or interior cavity of the instrument shaft 254. Male-female pairs of screw drive features may include geometries such as square, hexagonal, pentagonal, slotted, hexalobular, spanner, clutch, cross slot, or combinations of these geometries. In yet another embodiment, the rotational constraint may be provided through threaded male-female pairs.

According to another embodiment, axial constraint of the tool tip 258 may be accomplished through one or more mechanisms including but not limited to threaded mechanisms, quarter-turn locking mechanism, half-turn locking mechanism, and hook-latch mechanisms. In each embodiment, the axial constraint may be accomplished by male-female pairs of features where the male feature is located on the proximal end of the tool tip 258 and the female feature is located in the release mechanism 264 on the distal end or interior cavity of the instrument shaft 254 or vice versa. Threaded mechanisms, quarter-turn locking mechanisms, and/or half-turn locking mechanisms may be actuated through torsional force applied in a twisting motion. In contrast, the hook-latch mechanisms may be actuated through transverse loading of a release button on the instrument shaft 254.

In a traditional operative setting, several cases of large instruments are manufactured, transported, stored, sterilized, and unpacked prior to surgery. In contrast, the instruments 250 may allow a set of smaller tool tips 258 and/or fewer common handle-shaft constructs to be used in place of several, large cases of instruments. One benefit may be the availability of a variety of tool tips 258 in a smaller, cheaper, and more efficient package. The functionality of the traditional tool tips may be preserved while enabling pre-operative or intra-operative replacement. The tool tip 258 geometries may include, but are not limited to, drills, taps, awls, screwdrivers, cannulas, cup curettes, ring curettes, osteotomes, cobbs, elevators, rasps, rakes, paddle distractors, sizers, shavers, scrapers, trials, and implant inserters.

Surgeons sometimes prefer custom instrumentation to meet specific functional, ergonomic, or aesthetic requirements beyond the standard, traditional instrument offering. Medical device companies sometimes cater to these needs by custom manufacturing surgeon-specific instruments, which may be extremely costly and time consuming. By isolating customization to the critical component of the instrument (e.g., the tool tip 258) rather than the entire instrument, time and/or money may be saved. The custom tool tips 258 may be attached to a common handle-shaft construct. Such tool tips 258 may be co-designed with surgeons to meet preferred specifications and produced with traditional or advanced manufacturing methods. By using advanced manufacturing methods such as 3D printing or CNC machining, custom tool tips 258 may be produced in an automated environment with greater complexity and at a lower cost.

Turning now to FIGS. 23A-23E, embodiments of navigable instruments 270 with quick-connectors 278 are shown. Instruments 270 may be similar to the instruments 50 shown in FIGS. 6A-9F, for example. The navigable instruments 270 may include a handle 272 and array 276 with tracking markers 18, and an instrument shaft 274 capable of quick release or connection to the handle 272. The array 276 may be affixed to the handle body 272 with an array post 280. The array 276 may be fixed in position relative to the handle 272 or may be configured to rotate as described in other embodiments. Although a straight handle 252 is shown, it will be appreciated that a T-style handle or other suitable handle may be used.

In surgical navigation, some tracked tools (e.g., a drill, tap or screwdriver) may be axially symmetrical. For example, a representation of a drill looks the same no matter how the drill bit is rotated. The tracking array 276 for such tools can be mobile in its rotational coordinate about the tool since the rotational position of the tool does not need to be monitored. Therefore, marker arrays 276 for tracking these symmetrical tools may be designed with the array 276 on a sleeve that is free to rotate about the tool. The user can reposition the array 276 about the tool shaft as necessary to keep it facing toward the tracking cameras 30 while using the tool. However, it is sometimes necessary to track a tool that is not symmetrical (e.g., aa curved curette or a delivery device for an interbody spacer). In such cases, the system 10 may track the full rigid body position of the tool so that it can properly update the image of the tool overlaid on anatomy, showing, for example, which direction the curve or cutting surface of the curette faces. In these tools, different features may be used to ensure the tracking array's orientation is fixed relative to the tool in all directions including rotation. In addition, it may be desirable to attach and detach different tools to the tracking array intra-operatively without re-calibration of the tool-array assembly. This may need a rigid connection, which is accurate and repeatable.

According to one embodiment shown in FIGS. 23A-23C, the instrument shaft 274 may be attached to the handle 272 and tracking array 276 assembly with a quick-connector 278. The quick-connector 278 may include an extension 282 protruding from the proximal end of the tool shaft 274. The extension 282 is configured to be received in a bore 284 within the distal end of the handle 272. The tip 286 of the extension 282 may be tapered or otherwise configured to enhance receipt into the bore 284 of the handle 272. As best seen in FIG. 23B, the top of the tool shaft 274 may include a radial shoulder 288 with one or more tapered surfaces 290, and the base of the handle 272 may include one or more corresponding tapered surfaces 292. In this manner, the shaft 274 may be connected to the handle 272 and attached array 276 by incorporating two opposing tapered surfaces 290, 292 onto both the tool shaft 274 and the handle 272, such that the tapered surfaces 290, 292 make contact with one another, simultaneously constraining three rotational and two translational degrees of freedom of the tool. The last degree of freedom is constrained by the extension 282 of the tool shaft 274 into the bore 284 of the handle 272.

A button or latch 294 within the handle 272 may allow for quick release and attachment of the shaft 274. The bottom of the latch 294 may be received in a slot, groove, or recess 298 defined within the extension 282. The latch 294 positioned within the recess 298 in the extension 282 retains the instrument and controls orientation. When fully inserted, the base of the latch 294 is received within the recess 298 and the instrument 270 is locked. The handle 272 may house a tapered latch 296 for preload of the extension 282. By incorporating the latch 294 into the handle 272 and tracking array 276 assembly, which may preload the two components together, backlash or "slop" between the tool shaft 274 and handle 272 may be reduced or eliminated. The quick-connector 278 is able to quickly connect and disconnect from the handle 272, thereby providing for rigid attachment.

Figure 23D:
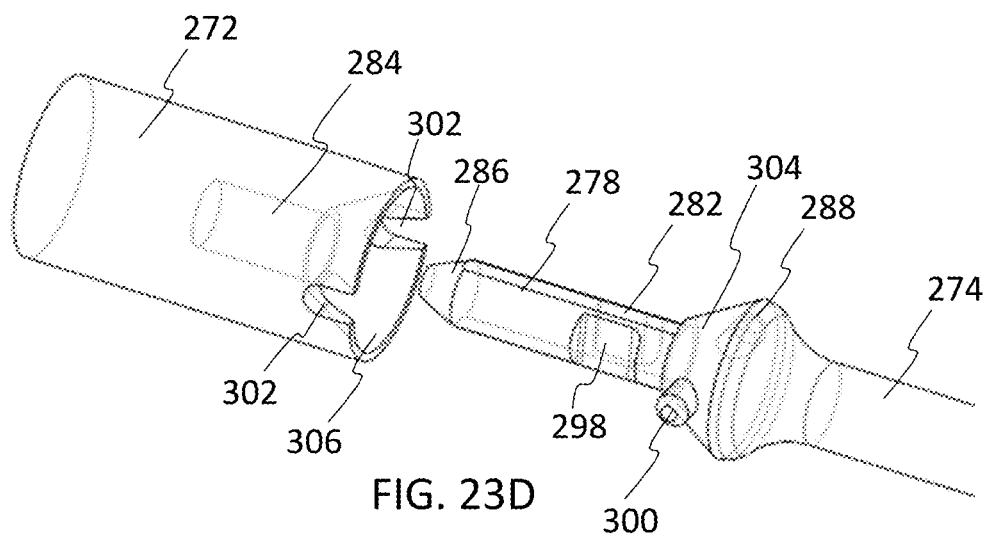

As shown in FIG. 23D, another embodiment of the quick-connector 278 is shown. The quick-connector 278 may include one or more cross-pins 300 configured to be received in one or more slots 302 in the handle 272. A transition 304 between the radial shoulder 288 and the extension 282 may include a tapered surface, a curved surface, a stepped surface, or any suitable transition. In one embodiment, the transition 304 is a male conical tapered surface 304, and the base of the handle 272 may include a corresponding female conical tapered surface 308 in communication with the central bore 284. The pin 300 may extend from the transition area 304 and may be transverse (e.g., generally perpendicular) to the central longitudinal axis of the shaft 274 and extension 282. The quick-connect interface may include the mating conical tapers 302, 304 combined with the cross-pin 300 to prevent rotation and provide a rigid connection between the shaft 274 and handle 272. The same or similar latching mechanism 294 as described for FIGS. 23A-23C may be used to maintain the connection and/or preload the components together.

Figure 23E:
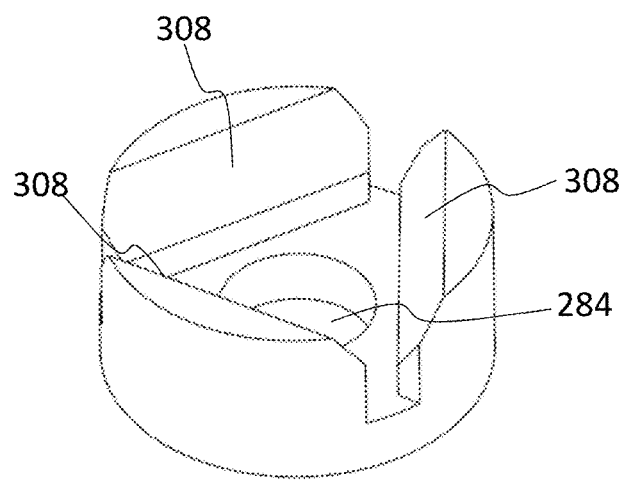

As shown in FIG. 23E, another embodiment of the quick connecting mechanism is shown. In this embodiment, the mating interface may include three flat tapered surfaces 308 configured to mate with three corresponding flat tapered surfaces. For example, the flat tapered surfaces may be oriented radially 120° apart from one another. The geometry may constrain the six degrees of freedom of the tool, center it along the tracking array's axis, and allow attachment in one rotational orientation. It will be appreciated that different or additional mating surfaces or features may be selected to rigidly couple the shaft 274 to the handle 272 and array 276 for navigation of the instrument 270 by the system 10.

Figure 24A:
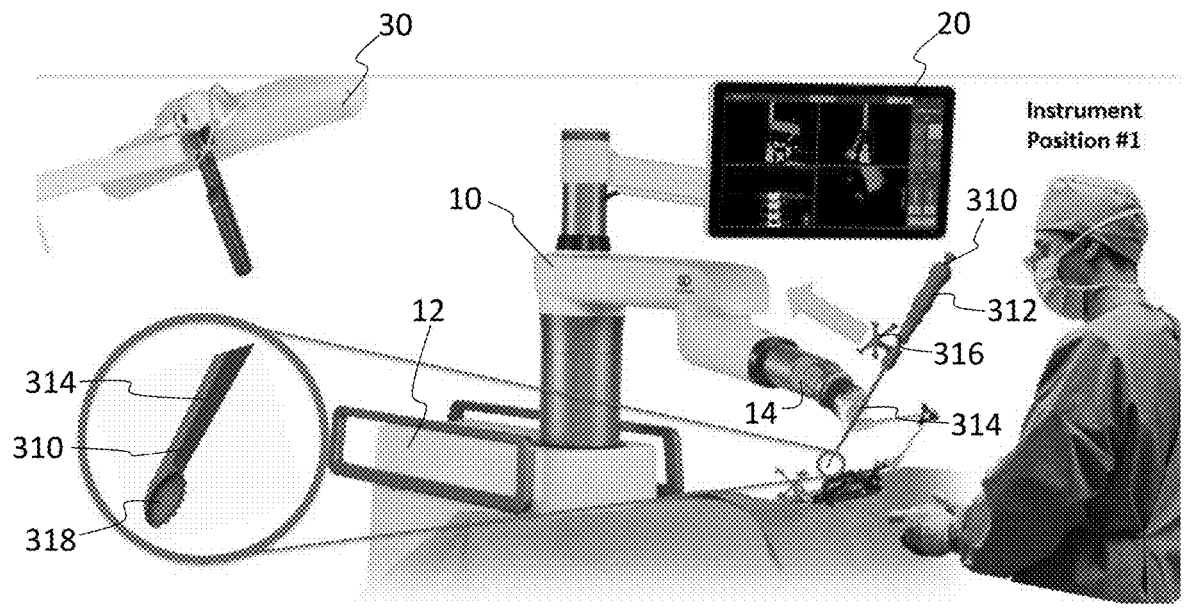
FIGS. 24A-24B show an embodiment of a navigated instrument handle with an array configured to index between rotational positions to align the instrument to desired camera locations.
Figure 24B:
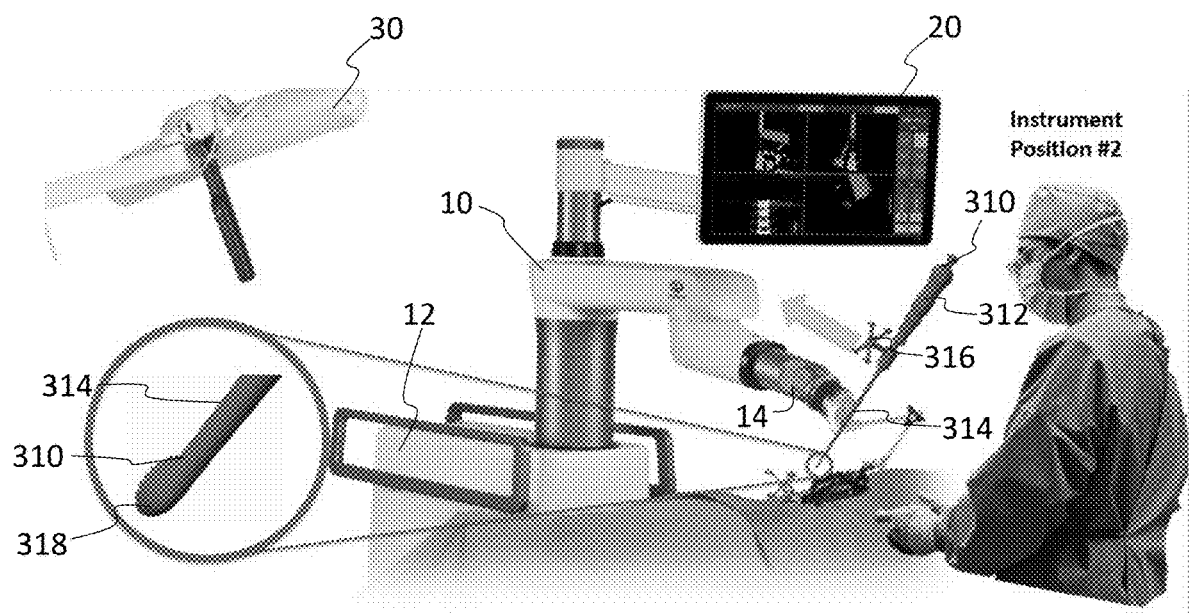

Turning to FIGS. 24A-24B, an instrument 310 including handle 312, shaft 314 with tip 318, and tracking array 316 is shown in two different instrument positions. In FIG. 24A, the instrument 310 is shown in a first position and in FIG. 24B, the instrument 310 is shown in a second position. Although the tip 318 of the instrument 310 is oriented in two different directions, the array 316 is visible to the camera 30 and the system 10 is able to the track the array 316. The instrument 310 may include any of the instruments described herein or other suitable instruments for surgical navigation.

In surgical navigation, instruments 310 may be tracked through optical or electromagnetic position sensors 18 and an associated computer-aided design (CAD) model is displayed relative to anatomical landmarks. In surgical robotic navigation, the instruments 310 may also be tracked and guided to planned positions using the robotic system 10. Surgical navigation or robotic navigation systems may track the full rigid body motion of an instrument 310 by measuring the position of the array 316 of optical or electromagnetic markers 18 relative to one another. With optical tracking systems, this may be achieved via a position sensor (e.g., camera 30) placed within the operating theater such that the tracked tools 310 are within its line-of-sight. A CAD model is mapped to these measured marker locations, oriented in 3D space, and displayed relative to anatomical images for the surgeon. One way to ensure the orientation of the tracking array 316 is known relative to the entire tool 310 is to rigidly mount the array 316 to the tool 310.

When the implant and instrument are axisymmetric, the array of markers and rigidly fixed instrument can be rotated to orient towards the camera 30, and the desired orientation of the instrument and implant relative to the anatomy is not compromised. In the case of non-axisymmetric instruments and implant inserters, however, there may be a case in which rotation of the instrument to maintain line-of-sight with the camera 30 causes an un-desirable orientation of the instrument relative to the anatomy. One embodiment is to enable rotation of the array 316 of optical markers 18 about the instrument's axis, so that the instrument 310 may be placed in the desired orientation relative to the anatomy, and the array 316 may be rotated independently toward the camera 30. In order to allow the CAD model to be mapped accurately to the measured marker locations, the orientation of the instrument relative to the instrument's axis must be known. In one embodiment, an indicator 336 to the user of the rotational position of the array relative to the inserter's axis may be provided, and then corresponding rotation of the displayed CAD model may be shown on screen 20.

Figure 25A:
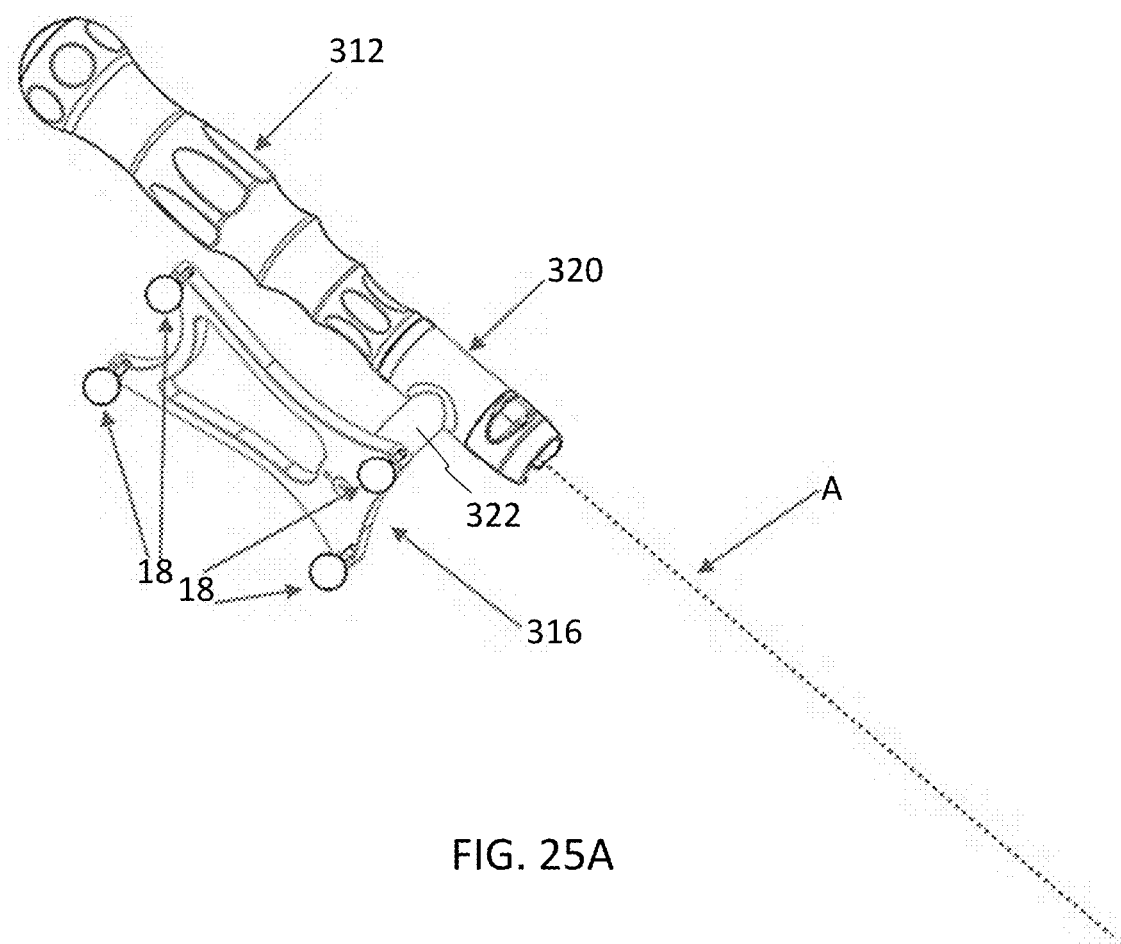

Turning to FIGS. 25A-25C, an embodiment of instrument 310 with a rotatable body 320 is shown. The handle 312 includes rotatable body 320 and array post 322 may couple array 316 to the rotatable body 320, and thereby provide for rotation of the array 316. The array 316 and body 320 may be free to rotate about the longitudinal axis A of the instrument. Axis A may include the central longitudinal axis of the handle 312 and/or the central longitudinal axis of the shaft 314. The array 316 may be rigidly attached to the body 320, which is capable of rotating on a cylindrical portion of the instrument's handle 312 which is concentric with the handle's axis A. The array 316 may contain one or more markers 18 rigidly fixed in known positions measured by the position sensor. In one embodiment, the array 316 may be able to index in two discrete rotational positions in order to align with the expected instrument orientations and camera locations within the operating theater. In another embodiment, the array 316 may be able to rotate to more than two discrete positions, such as four positions at 90° increments. It is envisioned that the array 316 may be permitted to rotate to any suitable position.

Figure 26A:
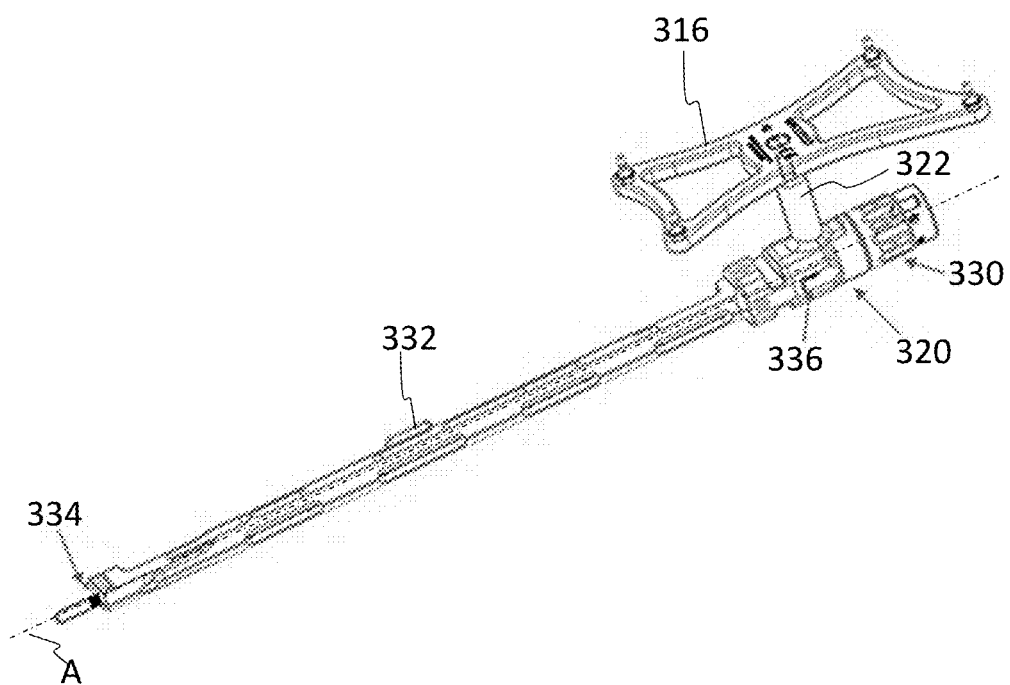
FIGS. 26A-26C shows another embodiment of a navigable implant inserter with a rotatable array mechanism.

In FIG. 26A, an embodiment of an inserter instrument 330 with rotatable body 320 is shown. Inserter 330 may be similar to inserters 80 shown in FIGS. 10C-13B. The inserter 330 may include a shaft or sleeve 332 and a tip 334 (e.g., a forked or threaded tip) for retaining an implant. The rotatable body 320 may be free to rotate about the sleeve 332 to provide for rotation of the array 316. The array 316 and body 320 may be able to rotate about the central longitudinal axis A of the sleeve 332. The body 320 may include a rotational position indicator 336. The indicator 336 may provide the user and/or system 10 with information regarding the rotational position of the array 316 relative to the shaft 332 and/or the inserter's axis A.

Figure 26B:
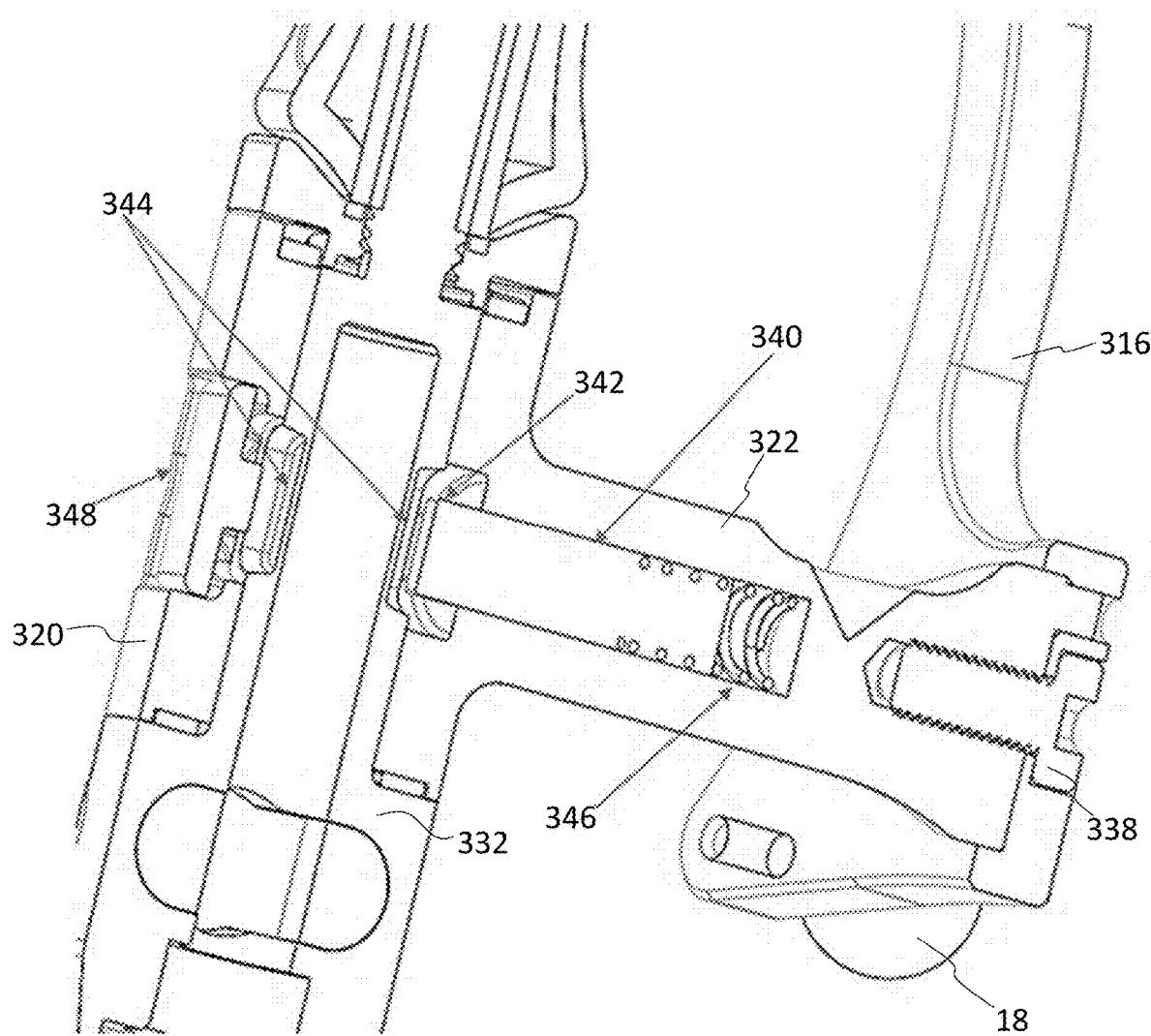
Figure 26C:
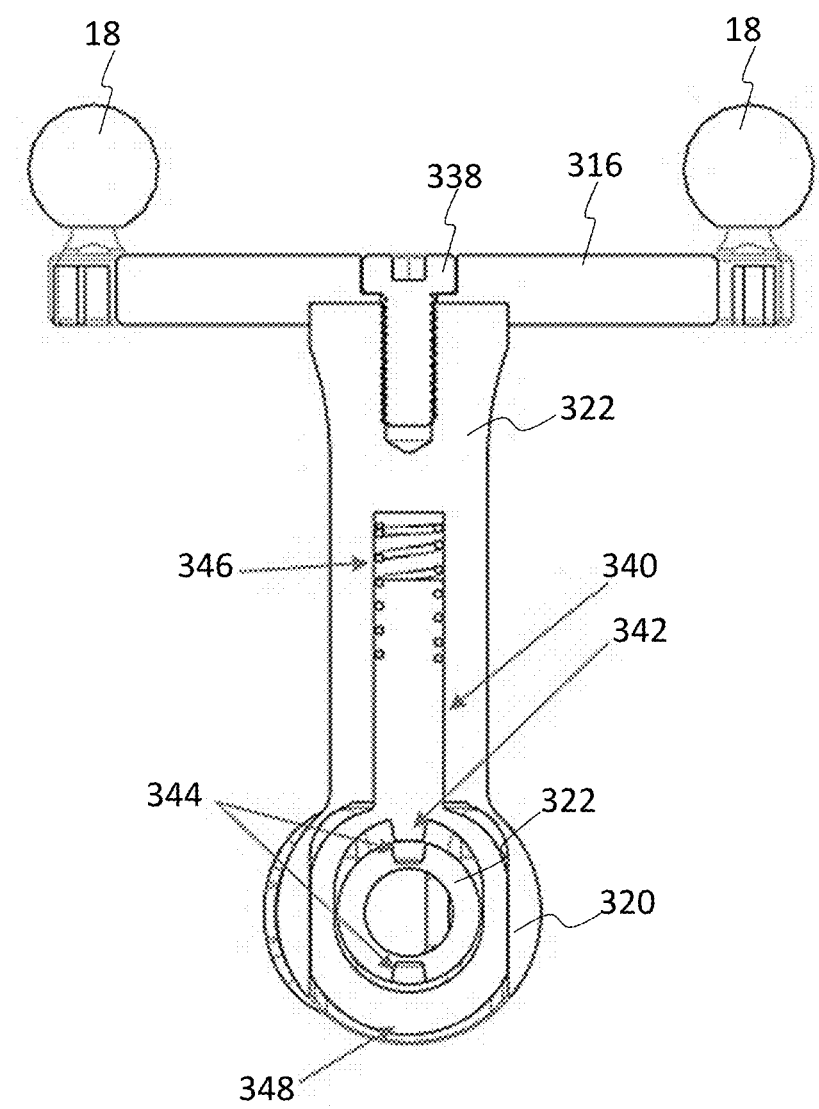

Turning to FIGS. 26B and 26C, one embodiment of rotatable body 320 is shown in greater detail. FIG. 26B shows a cross-section perspective view, and FIG. 26C shows a cross-section top view. The rotatable body 320 may be a rigid body that includes array post 322, and the array 316 may be attached to the free end of the array post 322 with a fastener 338 (e.g., a screw). The rotatable body 320 includes a cavity that houses a translating member 340 including a tapered key 342 at one end of the translating member 340. The tapered key 342 is configured to mate with one or more recesses or keyseats 344 in the shaft 332 of the inserter 330. When the array 316 has two index positions as shown in FIG. 26B, two opposed keyseats 344 may be present. It will be appreciated that any suitable number and orientation of keyseats 344 may be used to achieve the desired indexing of the array 316. The taper may allow the tapered key 342 to translate as far as necessary to fully seat in one of the keyseats 344 and remove any clearance from the assembly, thereby eliminating any movement between components. A spring 346 may be positioned at the end of the translating member 340 opposite the key 342. The spring 346 provides force for holding the key 342 in the keyseat 344, which can be overcome via a user input, such as a push button 348. When the button 348 is depressed and the spring 346 is compressed by the user, the tapered key 342 translates away from the keyseat 344. When the spring 346 is compressed, the array 316 is permitted to rotate about the inserter shaft 332 until the key 342 reaches the next tapered keyseat 344. The button 348 may be released and the key 342 engages with the next keyseat 344. In the case of two keyseats 344, the array 316 may be positioned in one of two index positions that are 180° apart. In the case of four keyseats 344, the array 316 may be positioned in one of four index positions that are 90° apart.

Figure 27A:
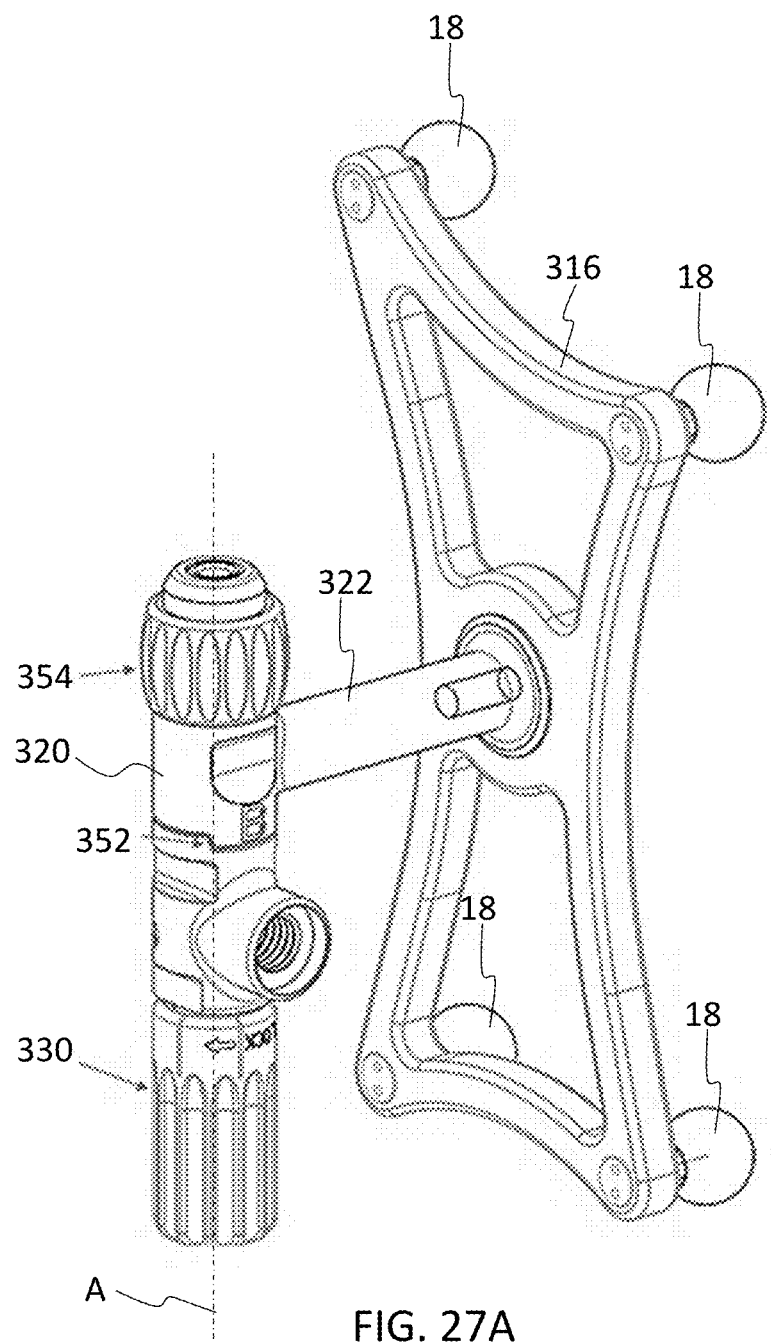
FIGS. 27A-27C provide another embodiment of a rotatable array mechanism.
Figure 27B:
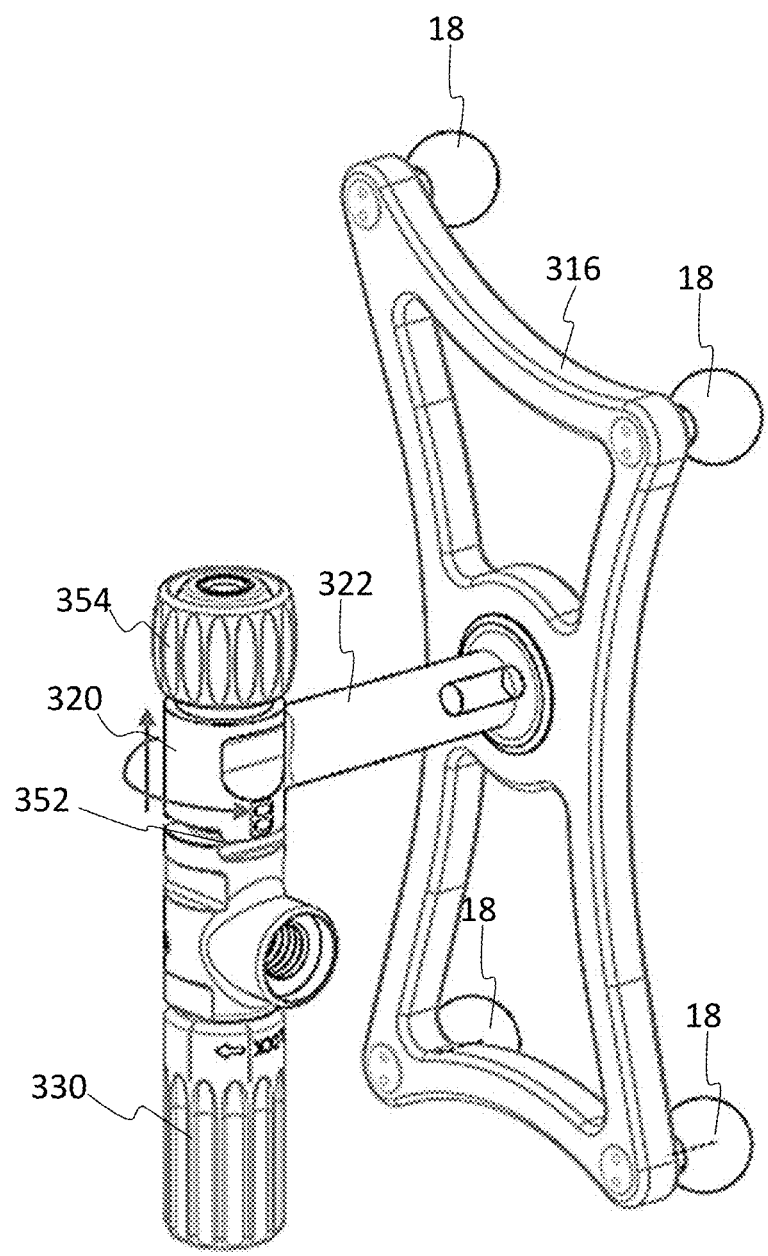
Figure 27C:
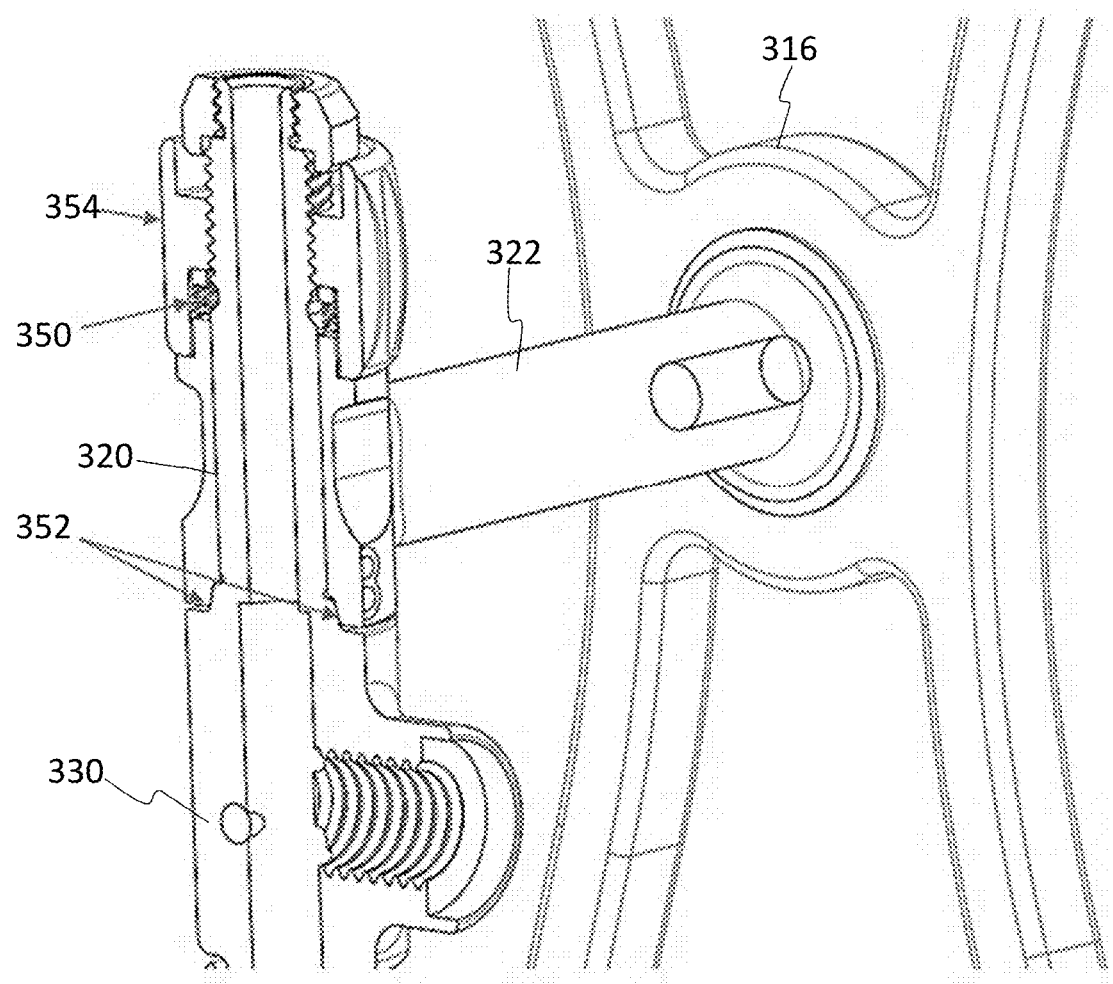

Turning to FIGS. 27A-27C, another embodiment of a rotatable body 320 is shown. In this embodiment, a spring loaded mechanism is used to hold the array component 316 in the desired orientation with respect to the inserter's axis A, but the spring 350 is arranged such that it is concentric with the instrument's axis A and the force provided by the spring 350 is in an axial direction, rather than the transverse direction. One or more mating tapered surfaces 352 may be used to remove any play from the assembly, with their orientation changed to align with the modified direction of the spring force. Two tapered surfaces 352 may be positioned on the bottom end of the rotatable array body 320. The tapered surfaces 352 may be symmetric about the instrument's mid-plane. When seated on mating tapers 352 on the inserter 330, the rotatable array component 320 is fully constrained so that the array orientation is fixed. The array 316 may be set in a position 180° rotated about the inserter's axis A by applying an axial force to compress the spring 350 and separate the tapered surfaces 352 on the rotatable body 320 and the inserter body 330. This frees one rotational degree of freedom to allow the array 316 to be rotated to its second position. A locknut 354 may be employed to prevent inadvertent spring compression (and array movement) when in the desired position, which may potentially result from impaction loads on the inserter 330 during implant insertion. FIG. 27A shows the locknut 354 in a downward position causing the mating surfaces 352 to engage between the rotatable body 320 and the inserter body 330, thereby locking the array 316 in a given position. FIG. 27B shows the locknut 354 retracted in a raised position causing the mating surfaces 352 to separate, thereby allowing the body 320 and attached array 316 to rotate.

Turning to FIGS. 28A-28D, embodiments of identification of instrument orientation using an inline array 360 is shown. The inline array 360 allows for line of sight visibility between the tracking camera 30 and instrument array 360 in both directions normal to the array plate 362. For marker patterns that are not symmetric about the instrument axis A, the camera 30 and software are able to distinguish the orientation of the instrument tip 364 with respect to the array plate 362.

Figures 28A, 28B:
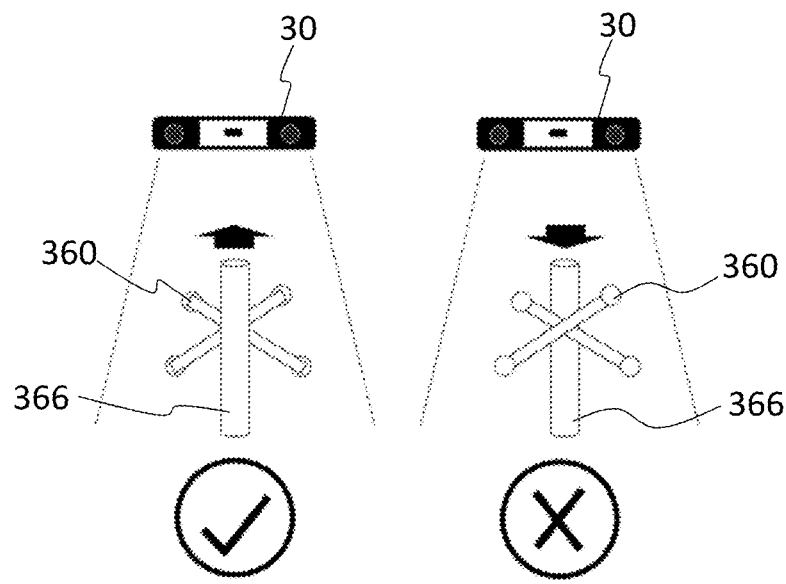
FIGS. 28A-28D provide embodiments of identification of instrument orientation using inline arrays.

In one array configuration shown in FIGS. 28A and 28B, reflective markers 18 are placed on posts positioned about the face of the array plate 362. This arrangement allows line of sight visibility between the tracking camera 30 and instrument array 360 in the direction normal to the array plate face in which the posts and markers 18 are located. If the array plate 362 is rigidly attached to an instrument 366 and the instrument 366 is rotated 180 degrees with respect to the tracking camera 30 visibility may be obstructed by the array plate 362. In FIG. 28A, the array 360 is visible to the tracking camera 30 when the array plate normal direction aligns with the camera field of view. In FIG. 28B, visibility may be obstructed by the array plate 362 when the array is rotated 180 degrees about the instrument axis A. For some screw instruments, this array configuration is adequate because the instruments 366 may be axisymmetric about the instrument axis A.

For instruments 366 with non-axisymmetric tip configurations, such as disc prep instruments, the array configuration may be unable to track the tool tip 364 in all instrument orientations. For example, if a cup curette is used to prepare the anterior and posterior endplates the instrument 366 may need to be flipped 180 degrees during use. With the array configuration in FIGS. 28A and 28B, visibility may be lost when the instrument 366 is rotated 180 degrees due to obstruction by the array plate 362.

Figures 28C, 28D:
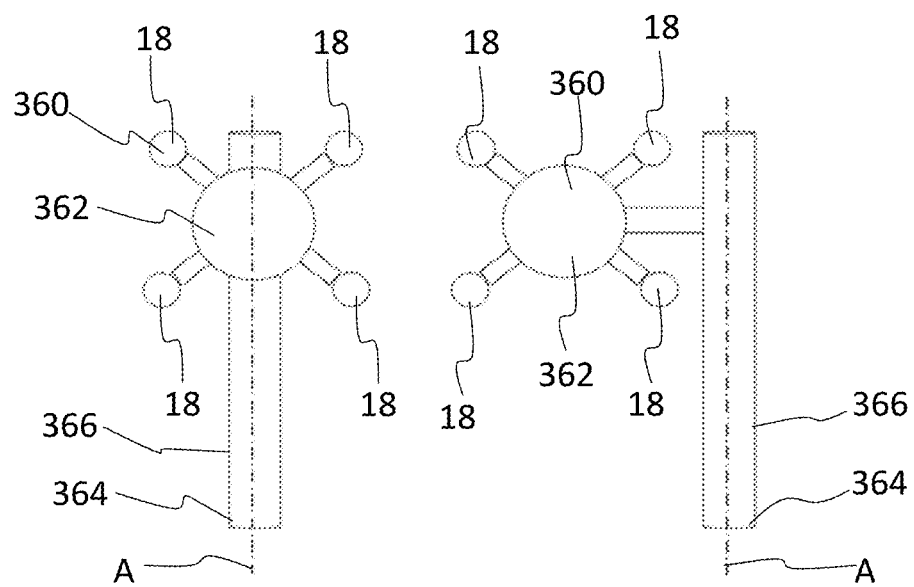

In FIGS. 28C and 28D, the array configuration may include markers 18 located on the edge of the array plate 362. Instead of having markers 18 located on the face of the array plate 362 with posts positioned normal to the array plate face, the posts may be positioned parallel to the face of the array plate 362. By having the markers 18 located on the edge of the array play 362 with the posts positioned parallel to the face of the array plate 362, the markers 18 may be visible from both directions normal to the front and back faces of the array plate 362. In FIG. 28C, a symmetrical configuration is shown with the array plate 362 aligned with the body of the instrument 366. In FIG. 28D, an asymmetric configuration is shown with the array plate 362 offset relative to the body of the instrument 366. In both cases, each array 360 is an inline array 360 with markers 18 located on the edge of the array plate 362 with posts positioned parallel to the array plate 362.

For asymmetric array patterns, the array configuration allows the tracking camera 30 and software to distinguish which side of the array plate 362 and instrument 366 is facing the camera 30. Asymmetric array configurations may include a pattern offset from the instrument axis A, as shown in FIG. 28D. It is envisioned that other asymmetric patterns could be used. For example, an asymmetric pattern may include three posts for markers 18 that are the same length and one that is longer or shorter. The fourth, different marker 18 may indicate the orientation of the tool 366 depending on which side of the tool the camera 30 determines the array 362 is located. In this manner, the software may automatically reorient the displayed CAD model when the instrument 366 is flipped 180 degrees during use.

Turning to FIGS. 29A-29G, embodiments of navigable trials 370 are shown. In interbody fusion, an implant is placed in the vertebral disc space to attempt to restore lost disc height. To ensure that the size of the implant accurately restores the height, trials that match the geometry of implants in the set may be placed into the disc space. Fluoroscopy (x-ray) may be used to verify that the trial is in the correct location and determine which implant size to use. However, the patient, surgeon, and surgical staff may be exposed to potentially harmful radiation due to the amount of fluoroscopy required for trialing. In addition, complications may arise from an inaccurately placed instrument and/or the trialing may be time consuming, which reduces surgical efficiency and patient safety. According to one embodiment, surgical robotic navigation technology may be used to navigate the navigable trial instruments 370 while greatly reducing or eliminating the need for intraoperative fluoroscopy, increasing accuracy, and/or increasing intraoperative efficiency.

Figure 29A:
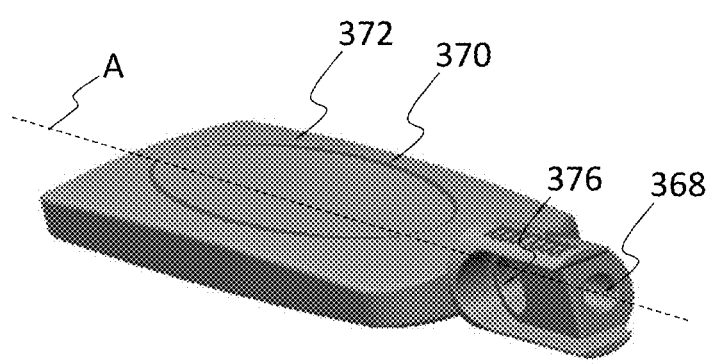
FIGS. 29A-29G include embodiments of navigable modular trials.
Figure 29B:
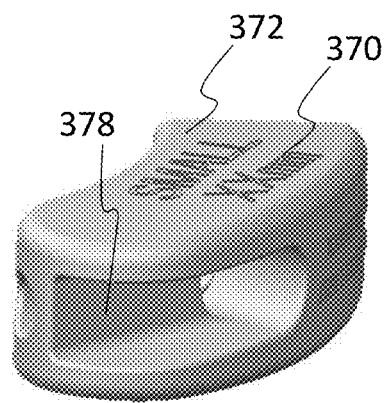
Figure 29C:
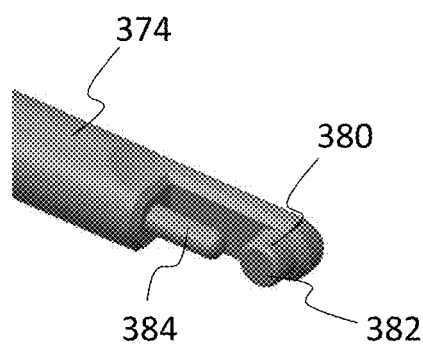
Figure 29D:
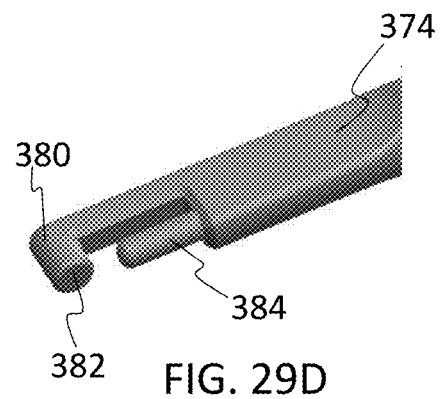

The navigable trial 370 may include a modular trial 370 with a removable trial head 372 couplable to an inserter shaft 374. Rather than having the head welded to a rigid shaft, the head 372 of the modular trial 370 is detachable from the navigated instrument shaft 374. The one or more heads 372 are configured to accurately represent each matching implant and may be easily attached and detached from the navigated inserter shaft 374. The trial head 372 is configured to match the outside geometry of one or more implants. As best seen in FIGS. 29A and 29B, the trial head 372 includes a connection portion with a first opening 368. The first opening 368 may be aligned along the central longitudinal axis A of the instrument 370. The trial head 372 may include a second opening 376 transverse to the first opening 368. The trial head 372 may also include one or more slots 378. The slot 378 may extend along the length of the trial head 372.

The trial head 372 attaches to a hook 380 on the inserter shaft 374. The hook 380 may be positioned at the distal end of the shaft 374. The hook 380 may include a protrusion, pin, or peg 382 extending transverse to the shaft 374. The peg 382 may be configured to be received within the transverse opening 376 in the trial head 372. The shaft 374 may include a moveable plunger 384 running through the inserter shaft 374. The plunger 384 may be configured to extend into the opening 368 in the trial head 372. When the plunger 384 is positioned within opening 368 in trial head 372, the trial head 372 is locked in place. The trial head 372 is fixed rotationally by the hook 380 and plunger 384, which allows the trial 370 to be manipulated inside the disc space.

Figure 29E:
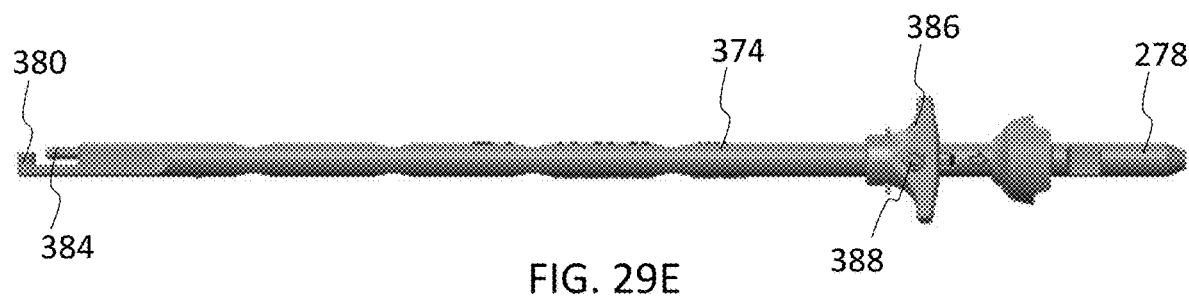
Figure 29F:
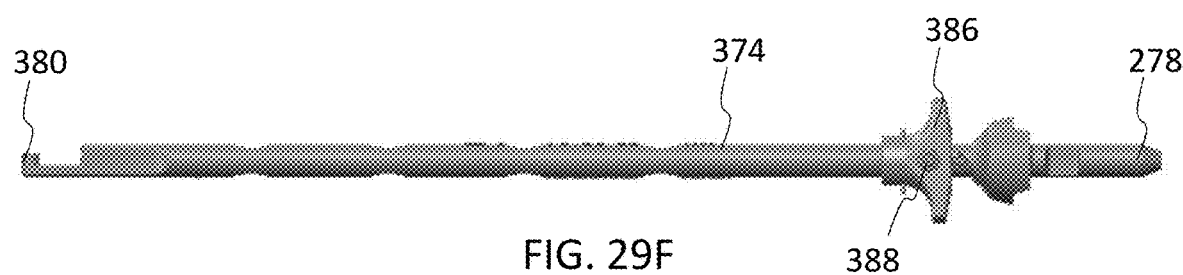
Figure 29G:
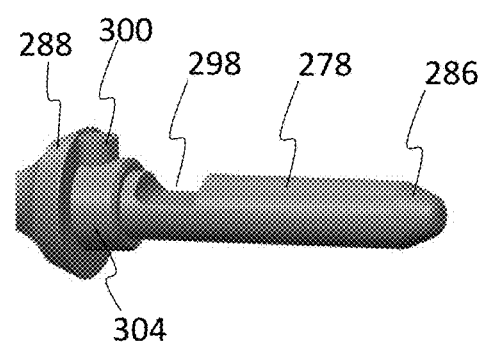

The plunger 384 may be manipulated by a trigger 386. The trigger 386 may be positioned on the outside of the inserter shaft 374. In FIG. 29E, the plunger 384 is deployed by pressing the trigger 386 toward the distal end of the shaft 374. In FIG. 29F, the plunger is retracted by pulling the trigger 386 toward the proximal end of the shaft 374. The trial head 372 may not be placed onto the inserter shaft 374 if the plunger 384 is in its exposed position (shown in FIG. 29E). The trial head 372 may not be removed from the inserter shaft 374 until the plunger 384 is retracted (shown in FIG. 29F). The trigger 386 may incorporate a lock 388, which may be actuated in order to move the plunger 384. The lock 388 may include a push button or a spring-loaded turn and pull mechanism, for example.

The back of the trial inserter 374 may include a quick connector 278, which may correspond to the couplings for the navigated array handles 50, 270. The quick connector 278 may be the same or similar to the quick connectors described herein. This allows for the quick connection of any suitable handle that can be used with the navigation system 10. Navigated modular trials 370 may eliminate the need for a large number of fixed trials. Instead of needing many trial heads with long fixed shafts, a caddy may be included in the set that features all the trial heads 372. The detachable inserter 374 can quickly swap between each size.

Figure 30A:
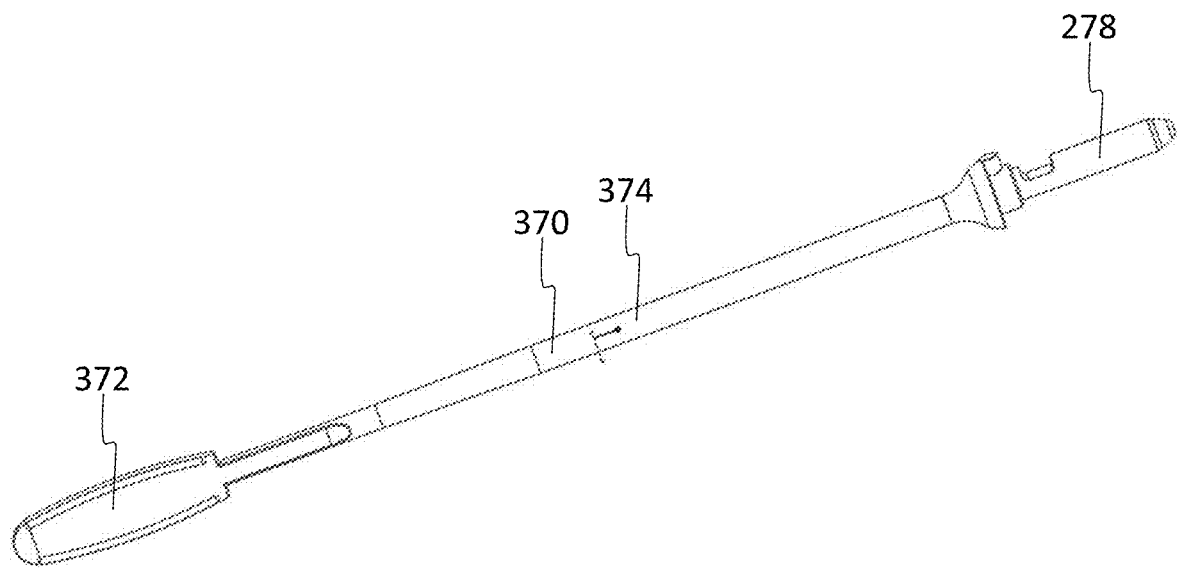
FIGS. 30A-30B show an embodiment of a navigable fixed trial.
Figure 30B:
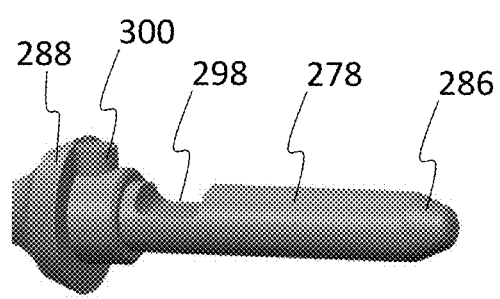

Turning to FIGS. 30A and 30B, another embodiment of the navigable trial 370 may include a fixed trial 370. Navigated fixed trials 370 provide navigation capability to fixed trials. In this embodiment, the distal end of the instrument 370 contains a rigidly attached trial head 372. The proximal end contains a rigidly attached quick connector 278 that permits attachment to any suitable handle with a navigation array. The navigated fixed trial 370 may be desired to reduce the need for fluoroscopic images during a majority of the trialing process. In addition, navigated fixed trials 370 offer a rigid, traditional, and simple option for trialing.

Figure 31A:
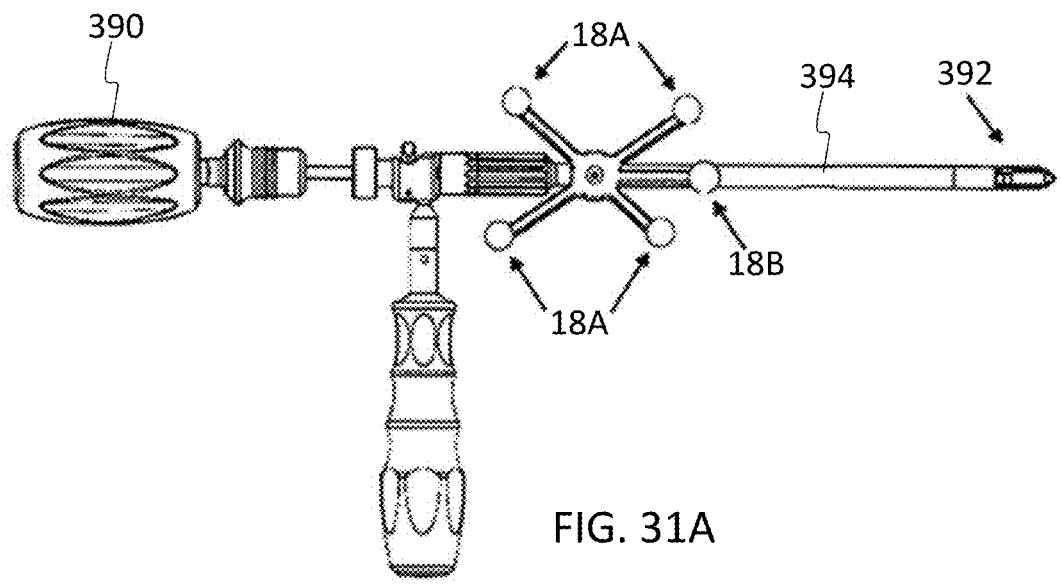
FIGS. 31A-31B show an embodiment of a navigable expandable trial.
Figure 31B:
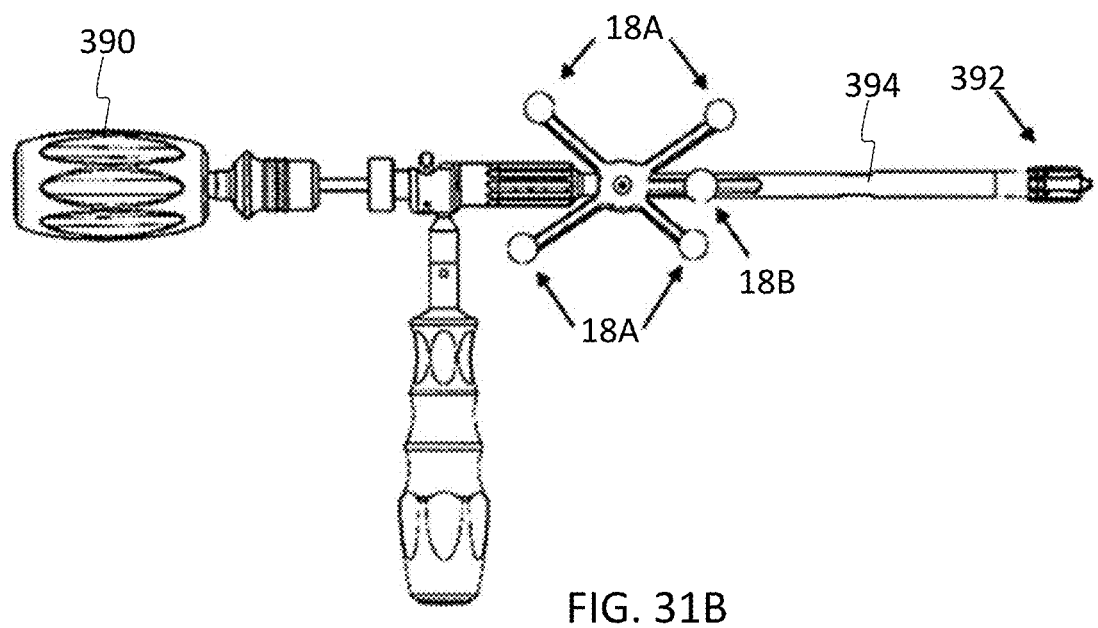

Turning to FIGS. 31A and 31B, embodiments of navigable expandable trials 390 are shown. Navigated expandable trials 390 may eliminate the need for various trial sizes. Instead of needing many trials heads with long fixed shafts, or many modular trial heads, a single expandable trial 390 may be included in the set that encompasses all the trial head sizes. The navigable expandable trial 390 may include an expandable trial head 392 positioned at the end of the instrument shaft 394.

The expandable trial 390 may include a tracking array containing a combination of fixed markers 18A and at least one movable marker 18B. The navigation array may include at least two fixed position markers 18A which are positioned with a known location relative to the trial holder instrument 390. The fixed markers 18A may not be able to move in any orientation relative to the instrument geometry and may be useful in defining where the instrument 390 is in space. At least one moveable marker 18B may be attached to the array or the instrument itself, which is capable of moving within a pre-determined boundary (e.g., sliding, rotating, etc.) relative to the fixed markers as defined above. As the trial is expanded, the movable marker 18B may act as an indication of the extent of expansion to the robotic system 10. Although the movable marker 18B is depicted with respect to sliding, rotation of the marker 18B may be useful to provide information about the implant. Any relative change in position between the set of fixed markers 18A and the movable marker or markers 18B may be used. The corresponding software correlates the opposition of the movable marker 18B to a particular position, orientation, or other attribute of the trial (such as height of an expandable interbody spacer or angle of an articulating interbody spacer).

FIGS. 31A and 31B shown an example where four fixed markers 18A are used to define the expandable trial 390 and a fifth moveable marker 18B is permitted to slide within a pre-determined path to provide feedback on the trial height. FIG. 31A shows the expandable trial head 392 at its initial height and FIG. 31B shows the trial head 392 in an expanded state with the moveable marker 18B translated to a different position. The translation of the marker 18B may correspond to the height of the trial head 392. Although only two positions are shown, it will be appreciated that the movement is a continuous function whereby any given expansion height may be correlated to a specific position of the movable marker 18B.

In one embodiment, the movable marker 18B slides continuously to provide feedback about an attribute of the trial based on position. It is also contemplated that the movable marker 18B may have discreet positions that the moveable marker 18B are positioned into, which may also be able to provide further information about a trial attribute. With discreet positions, the software is configured to determine each discreet configuration of all markers 18A, 18B, which correlates to a specific geometry of the implant holder and/or implant in a specific orientation or at a specific height. In addition, any motion of the movable marker 18B may be used for other variable attributes of the navigated trial 390. The navigated expandable trial 390 allows for a single trial instrument that may account for multiple sizes of implants.

Figure 32A:
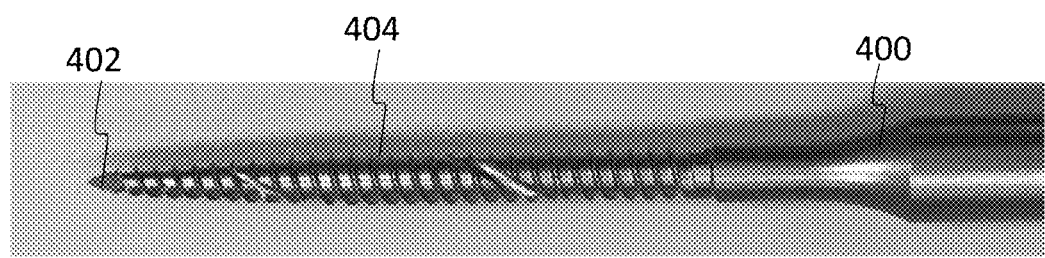
FIGS. 32A-32B show embodiments of navigable awl-tip taps.
Figure 32B:
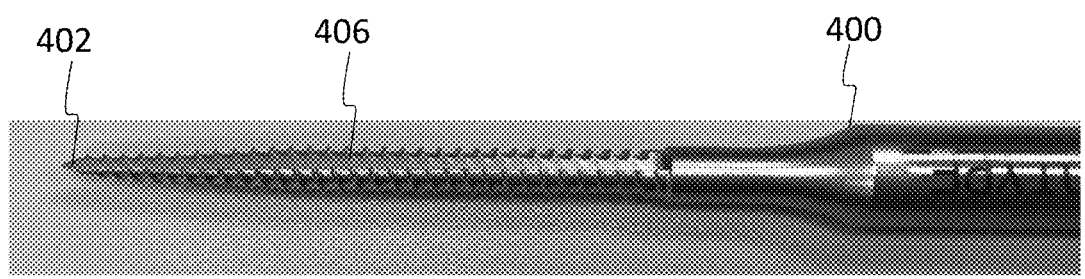

Turning to FIGS. 32A and 32B, embodiments of navigable awl-tip taps 400 are shown. During spine surgical procedures, in which screws are placed within the anatomy of the spine, drilling and tapping are steps within the procedure that may occur prior to placing the screw. In the embodiments, a sharp tip 402 at the end of the tap may assist during tapping of the screw hole. The awl-tip 402 may assist with partial or full drilling of the screw hole. Navigation of the awl-tip tap 400 may help to ensure the sharp tip 402 of the tap 400 does not pierce unwanted areas of the anatomy.

The goal may be to perform the surgical procedure as quickly and accurately as possible. With this, surgeons may prefer to combine steps prior to inserting the implant, if possible. The awl-tip tap 400 may allow the surgeon to combine the drilling and tapping phase, thus eliminating a step and eliminating some time. The taps 400 may be used to add threads to a hole in bone intended for a screw or threaded device. During surgical spinal procedures, the tap 400 may be used after drilling into the bone to add threads, which allow the screw to be placed and anchor inside the screw hole. The sharp tip 402 may assist with anchoring the tap 400 to the bone and/or drilling through the bone if drilling is not fully completed. The awl-tip tap 400 may have a spiral flute 404 (shown in FIG. 32A) or a straight flute 406 (shown in FIG. 32B). The spiral flute 404 may assist with pulling the chips of threaded material to the surface, away from the direction of tapping. The spiral flute 404 may help evacuate the bone chips from the hole during use, which may be advantageous if the surgeon is eliminating the drilling step of the procedure. The straight flute 406 may be used for general purpose. The threads may be lengthened up the shaft of the tap 400, which may help with the removal of the tap 400 while it is being navigated and constrained by the end effector. A taper along the length of the tap 400 may assist the surgeon with gradually easing into thread forming. The awl-tip taps 400 may be navigated in the same manner described for other instruments.

Figure 33A:
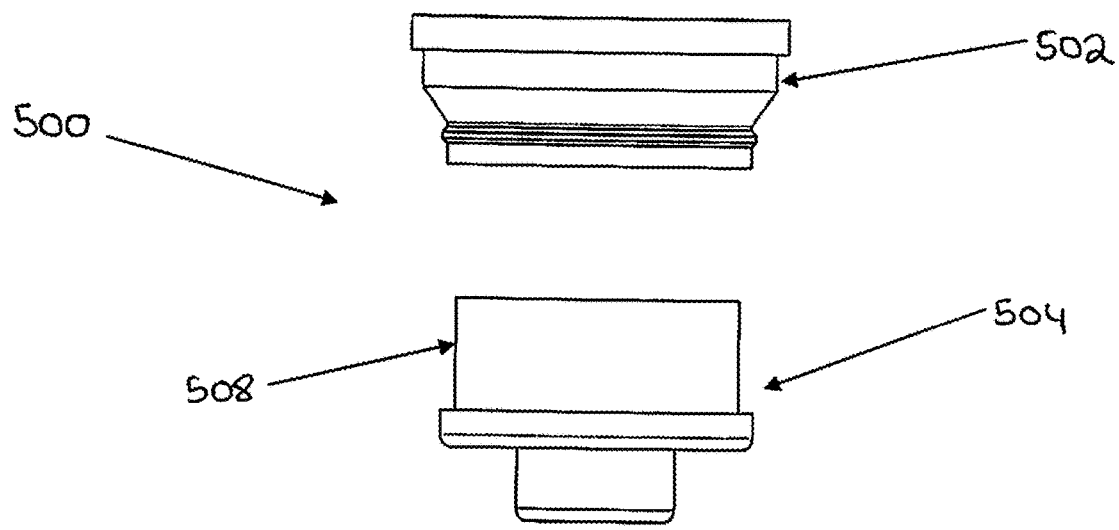
FIGS. 33A and 33B illustrate an embodiment of a preferred trackable disk assembly.
Figure 33B:
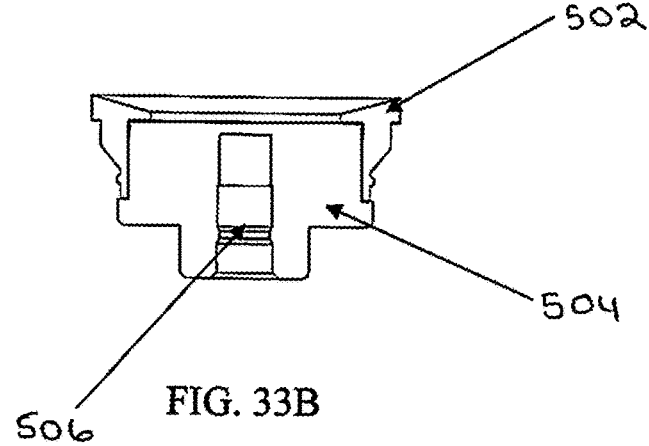

Now turning to FIGS. 33A and 33B, another embodiment of a preferred optical marker is shown. As discussed above, instruments are generally tracked using a spherical marker that is attached to an instrument, however, in some cases retro-reflective spheres tracking may be limited due to the retro-reflective spheres blocking other spheres when tracking off-axis. To overcome the loss of tracking or the tracking accuracy, FIGS. 33A and 33B illustrate another embodiments of a novel retro-reflective disk 500.

FIGS. 33A and 33B illustrate an embodiment of a retro-reflective disk 500 configured as a two-piece assembly. The two-piece assembly includes an upper portion 502 and a lower portion 504. The upper portion 502 is coupled to the lower portion 504. The upper portion 502 includes a black chamfered border, allowing the instrument to the be tracked. In other embodiments, various other geometric shapes may be utilized as a black border that can be visualized by a camera system. The lower portion 504 is configured to be snapped into the top of an array 506, and configured to be positioned inside the array, as to reduce contact or snagging on to other objects within the surgical field. The inner portion 504 includes an upper element having a reflective surface for near infrared (NIR) tracking or a white surface for tracking via visible light. The inner portion 504 is configured to be received within upper portion 502 as illustrated in FIG. 33B. The upper portion 502 includes an outer diameter that is greater than largest diameter of the lower portion 504. The chamfered end of the upper portion 502 is configured with a black border allowing the camera system to track the retro-reflective disk continuously. In another embodiment, upper portion 502 and the lower portion 504 may be permanently joined, using methods such as ultrasonic welding or epoxy, for ease of user installation into the array body.

Figure 34A:
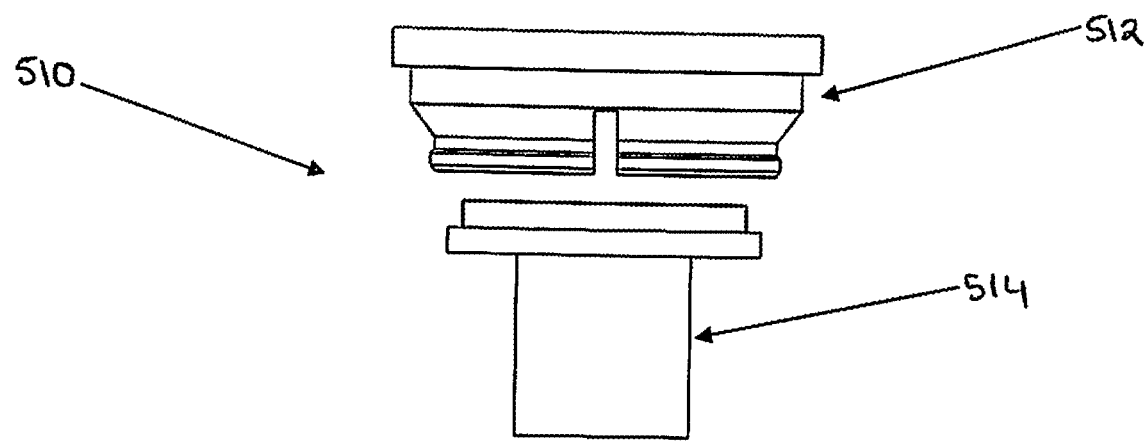
FIGS. 34A and 34 B illustrate another embodiment of a trackable disk assembly.
Figure 34B:
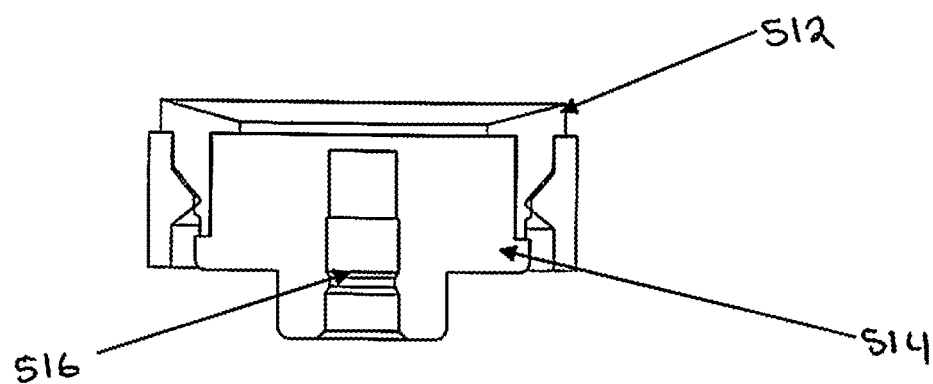

FIGS. 34A and 34B illustrate another embodiment of a retro-reflective disk 510. Disk 510 includes a upper portion 512 and a lower portion 514. The upper portion 512 includes a through hole extending from a proximal end to the distal end. The upper portion 512 is tapered from the proximal end to the distal end. The distal end of the upper portion 512 includes a plurality of slots 528, enabling the distal end to be flexible. The distal end is configured to receive the upper element of the lower portion 514. The upper element of the lower portion is configured with a reflective film to allow the camera system to track the disk 510. FIG. 34B illustrates the assembly of the upper portion 512 and the lower portion 514. The lower portion 514 receives a portion of the array 518. Disk 510 is configured to attach to the array 518 body using a snap feature, in which the disk 510 may be pushed into the array 518, and there would be an interference between the disk 510 and the array 518 which would lock the disk 510 in place. To remove the disk 510 from the array 518, the disk would be pushed out of the array 518 from the back of the array 518.

In other embodiments, the disks may be threaded into the array or magnetics may be utilized to couple the disks to the array.

Figure 35:
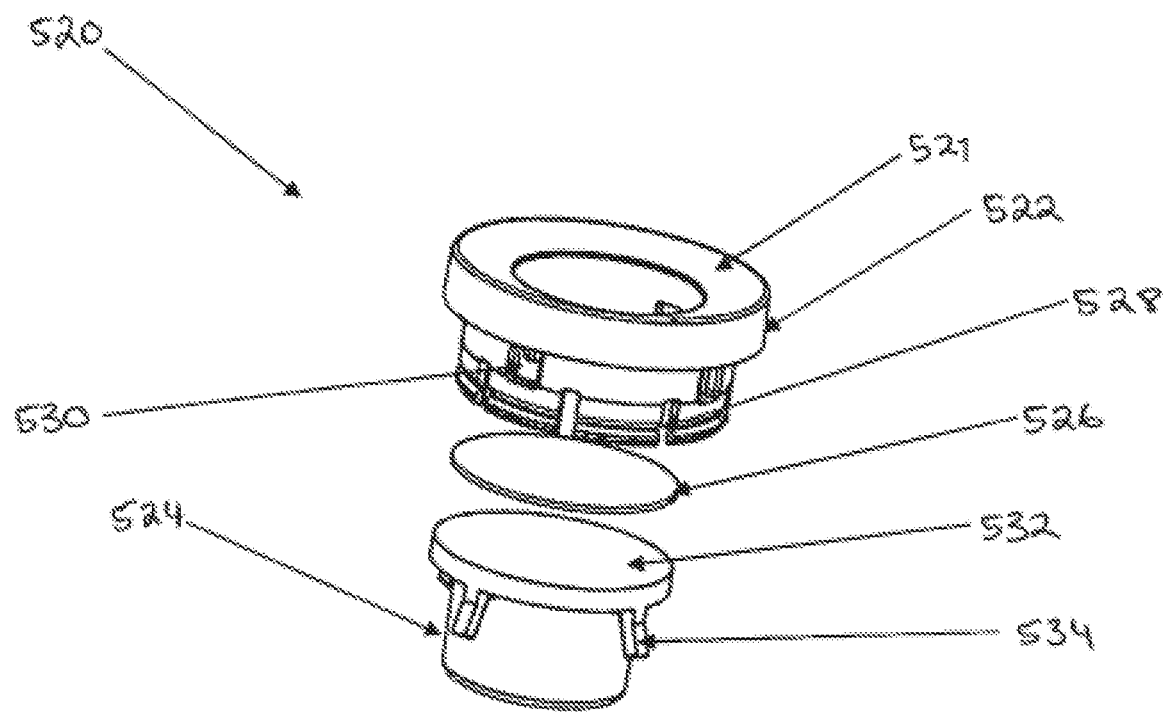
FIG. 35 illustrates yet another preferred embodiment of a trackable disk assembly.

FIG. 35 illustrates yet another embodiment of a retro-reflective disk assembly 520. The disk assembly 520 includes a upper portion 522, a lower portion 524, and a reflective film 526. The upper portion 522 includes a proximal end and a distal end. A through hole extends from the proximal end to the distal end of the upper portion 522. The upper portion further includes a chamfered upper surface 521 on the proximal end of the disk assembly 520. The distal end of the upper portion includes coupling features configured to enable coupling with the lower portion 524. In one embodiment, the upper portion 522 includes a plurality of slots 528 and openings 530. The lower portion 524 includes a upper flat surface 532 for receiving the reflective film 526. The reflective film 526 is configured to be adhered to the flat surface 532. The lower portion 524 also includes a plurality of extensions 534 that is configured to be received within the openings 530. The extensions 534 are designed as flexible tabs that when the disk assembly 540 is assembled fits into corresponding openings in the upper portion 522. The lower portion 524 includes a cylindrical lower end that is hollow for receiving a post from an array. In other embodiments, the reflective film 526 may be configured to be any color or shape to be visualized by a camera system.

Figure 36A:
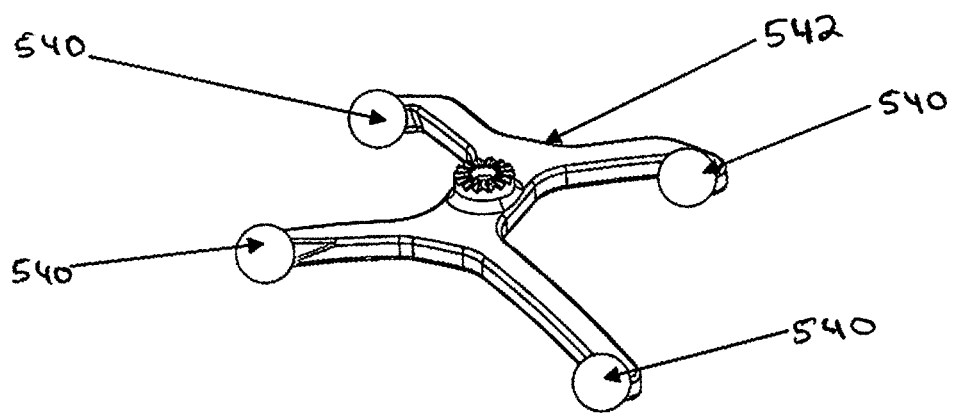
FIGS. 36A and 36B illustrates an embodiment a trackable sphere assembly.
Figure 36B:
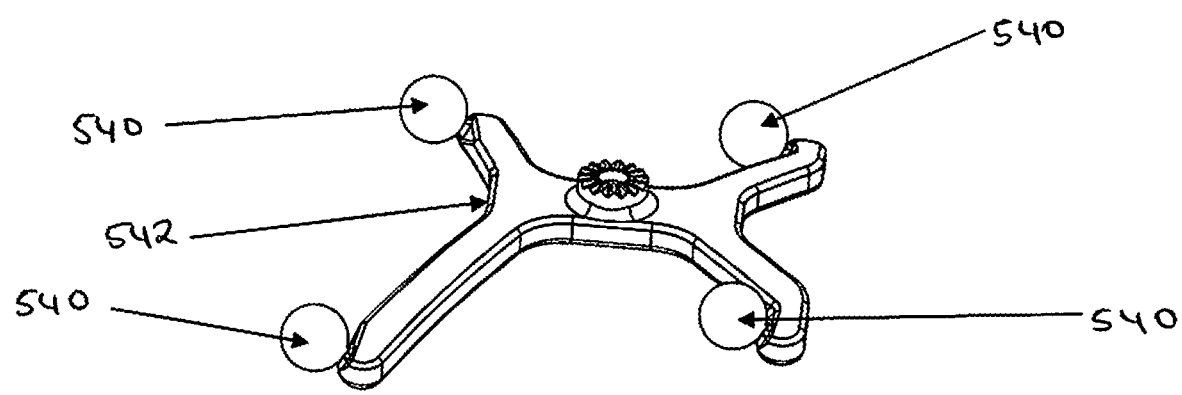

Now turning to FIGS. 36A, 36B, and 36C, another embodiment of an optically trackable reflective sphere that can be detected through image processing within the radiographic CT volume is shown. FIGS. 36A and 36B illustrate trackable reflective spheres 540 that are configured to share the same location in space when optically tracked as when it is detected in CT or imaging scan. In a preferred embodiment, sphere 540 is a unitary body that is both trackable and detectable on CT, sharing a common center location point in either coordinate system (camera or CT volume). Each of the four spheres 540 shown in FIGS. 36A and 36B are individually trackable by tracking cameras and also detectable within a CT volume through image processing. The scaffolding of the array holds the four spheres 540 in a slightly asymmetric pattern to aid in auto-sorting of markers during tracking of individual sphere locations.

The spheres 540 are mounted on posts that extend rearward and downward so that the portion of the sphere facing the cameras is viewed unobstructed and without any part of the mounting post in view. The scaffolding may be made of black or dark plastic for good contrast with the spheres. There is a slight concave bow in the scaffolding from left to right to allow the fixture to be positioned close to the torso, which is expected to be convex.

The sphere fixture provides a scaffold to hold the four spheres, and this fixture provides a known layout of the spheres in space. This known layout can be used by the sphere detection algorithm to improve the speed of processing by limiting the search region to regions expected by the shape of the scaffold.

The reflective sphere 540 in one embodiment is coated with a reflective film and a radio-opaque chemical such as barium sulfate. As a result, the sphere may be tracked via a camera system and detectable on a CT scan. In another embodiment, the tracking sphere 540 may be a hollow sphere that is filled with a radio-opaque liquid or radio-opaque powdered solid. In yet another embodiment, the sphere 540 can be completely formed of a material such as titanium that is radio-opaque and then painted or otherwise treated to make its surface reflective. In another embodiment, a shell of appropriate material such as plastic may be created, within which a metallic sphere is embedded. Such a composite sphere 540 may be produced through an over molding process or by gluing or snapping halves of a shell around a metal sphere. The tracking sphere 540 may be configured with the correct dimensions for the tracking system, thereby allowing a robotic computer system to track and monitor the sphere 540.

In other embodiment, spheres 540 can be used for registering different spaces. For instance, in one embodiment, a sphere 540 may have embedded material that also appears with high contrast on MRI, such as a center filled with Vitamin E or other oil, while also having a reflective outer shell to allow registration of MRI to tracking, or additionally/alternately could have a metal shell to allow co-registration of MRI, CT, and tracking coordinate systems.

Figure 37:
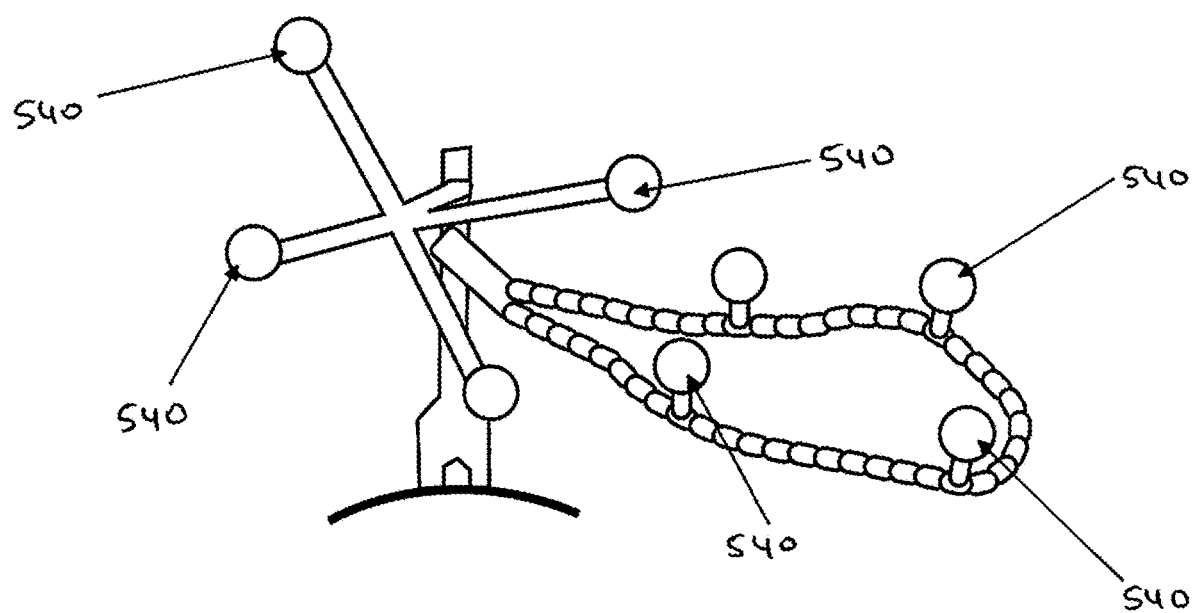
FIG. 37 illustrates yet another embodiment of a trackable sphere assembly.

Spheres 540 may be coupled to fixed arrays as shown in FIGS. 36A and 36B or may be coupled to flexible arrays such as shown in FIG. 37. Attachment to the patient through such a semi-rigid or flexible system would allow the fixture to be easily positioned where desired before obtaining the CT scan.

FIGS. 36A, 36B and 36C illustrate another embodiment of a reflective disk 550. The flat circular reflective disk 550 is configured to be tracking optically and through an imaging modality. The flat circular disk 550 according to embodiment of FIGS. 36A-36C, offers additional accuracy for tracking instruments during a surgical procedure. The present embodiment, provides a reflective disk, as each camera detects the face of the disk 550 as an ellipse. Utilizing the edges of the reflective region of the disk 550 and correlating the elliptical detected shape to the view angle, the disk configuration allows for greater accuracy.

The disk 550 as provided is configured to be detected through image processing within the radiographic CT volume. The disk 550 shares the same location in space when optically tracked as when it is detected in the CT, the disk 550 allows for easier registration between sets of detected points in one modality to corresponding points in another modality. The disks 550 in the preferred embodiment provide tracking markers and the radio-opaque markers in a single body.

Figure 38A:
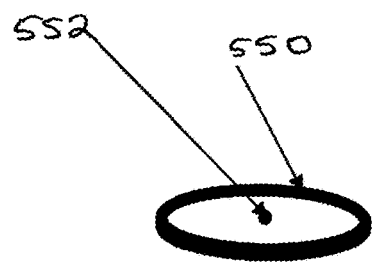
FIGS. 38A, 38B, and 38C illustrates a perspective, top and side view of a trackable disk.
Figure 38B:
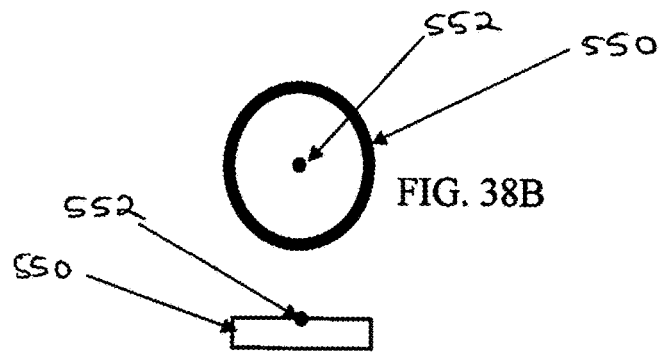
Figure 38C:

As illustrated in FIGS. 38A-38C, the center point 552 of the visible face of the disk 550 is the 3D point localized when tracking the disk 550 through stereophotogrammetry; the same location on the disk 550 must be detected through image processing of the CT volume for registration.

To produce or manufacture a optically tracked disk, a small piece of reflective tape or film or a thin layer of reflective paint is used to coat the flat visible surface, while a high-contrast (typically black) ring 554 containing an exactly known area and a small and having a well-defined lip is placed around the visible area. To make such a disk 550 into a disk of the preferred embodiment, the surface on which the reflective tape or paint is mounted can be formed of radio-opaque metal. The localization algorithm should account for the thickness of the reflective film in relating the tracked disk location to the location detected within the CT volume.

The tracked point of a disk 550 is the center point 552 of the visible face of the disk. An additional radio-opaque detectable feature on the disk, such as a mounting pin that is metallic, may be applied to indicate the non-visible side, eliminating the non-visible disk face.

Figure 39:
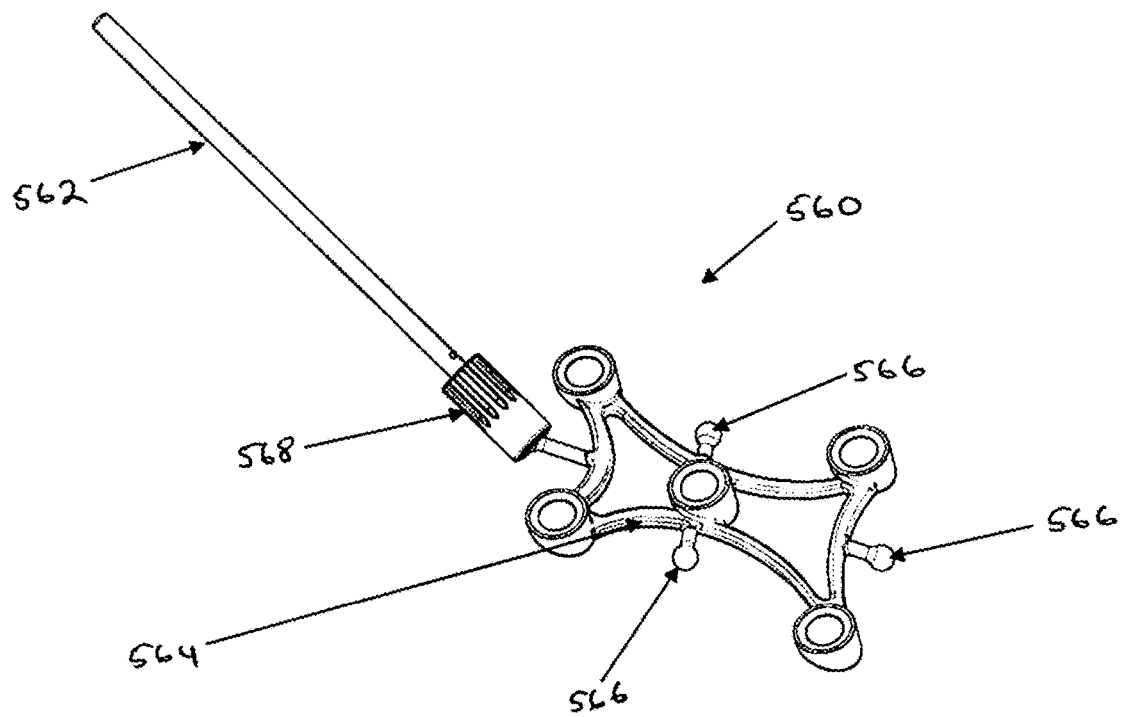
FIG. 39 illustrates an embodiment of a fixture for receiving the trackable disk of FIGS. 38A, 38B, and 38C.

Registration requires six degrees of freedom to be defined in each space (image or tracking), in a preferred embodiment, three or more disks 540 are used for co-registering spaces. As illustrated in FIG. 39, a fixture 560 is contemplated in which 5 disks positioned in a slightly asymmetrical pattern. In a one embodiment, five markers are selected, the increased number of markers provides better localization accuracy in both coordinate systems by providing more data points. The pattern of disk face center locations is asymmetrical to eliminate ambiguity in matching the detected points between the image and tracking space.

The fixture 560 provides an elongated bar 562 coupled to the base 564 that may be rigidly coupled to the patient while also allowing the fixture 560 to be positioned above the surgical site without touching the patient. Four spherical attachment points 566 extending outward from the fixture 560 provide different possible attachment points for the bar 562, allowing the most appropriate attachment point 562 to be selected for the setup of cameras relative to surgical site and patient attachment point. A connector 568 with a tight-enable locking mechanism allows the fixture's angle to be adjusted as needed for positioning. Each disk may be angled by 30° in its housing for better camera visibility.

In an preferred embodiment, the disks are most accurately tracked when they are facing toward the tracking cameras, it is contemplated that the disks should be placed at an angle on wherein each disk tilts toward the expected location of the cameras). In this embodiment, the angle is set at 30°. In other embodiments, the angle the disks may be fixed can range from 0° and 90°, or wherein each disk can be independently swiveled in is attachment to the fixture's scaffold.

In detecting the locations of the visible faces of the disks in the CT space, In one embodiment, the location of the radio-opaque objects of approximately the known size contrasting with radiolucent regions of the image volume may be used. The algorithm utilizes the one or more flat surfaces and localize the center of any flat surface as a candidate for a localized trackable point.

In another embodiment for tracking of the optical and radiolucent markers, the CT detection algorithm may use the known shapes of detected disks, scanning the volume for objects having an approximate match to the expected disk shape and then performing a best fit of the detected shape to the expected shape. The disk fixture provides a scaffold to hold at least five disks, and this fixture provides a known layout of the disks in space. This known layout may then be utilized by a preferred algorithm to improve the speed of processing by limiting the search region to regions expected by the shape of the scaffold on the fixture. The preferred algorithm utilizes the accuracy of tracking each independent disk to create the pattern of disk face centers at the time of surgery to match to the CT-detected disk face centers. In another embodiment, one or more of the disks may be partially or fully cropped in the CT image volume.

Figure 40:
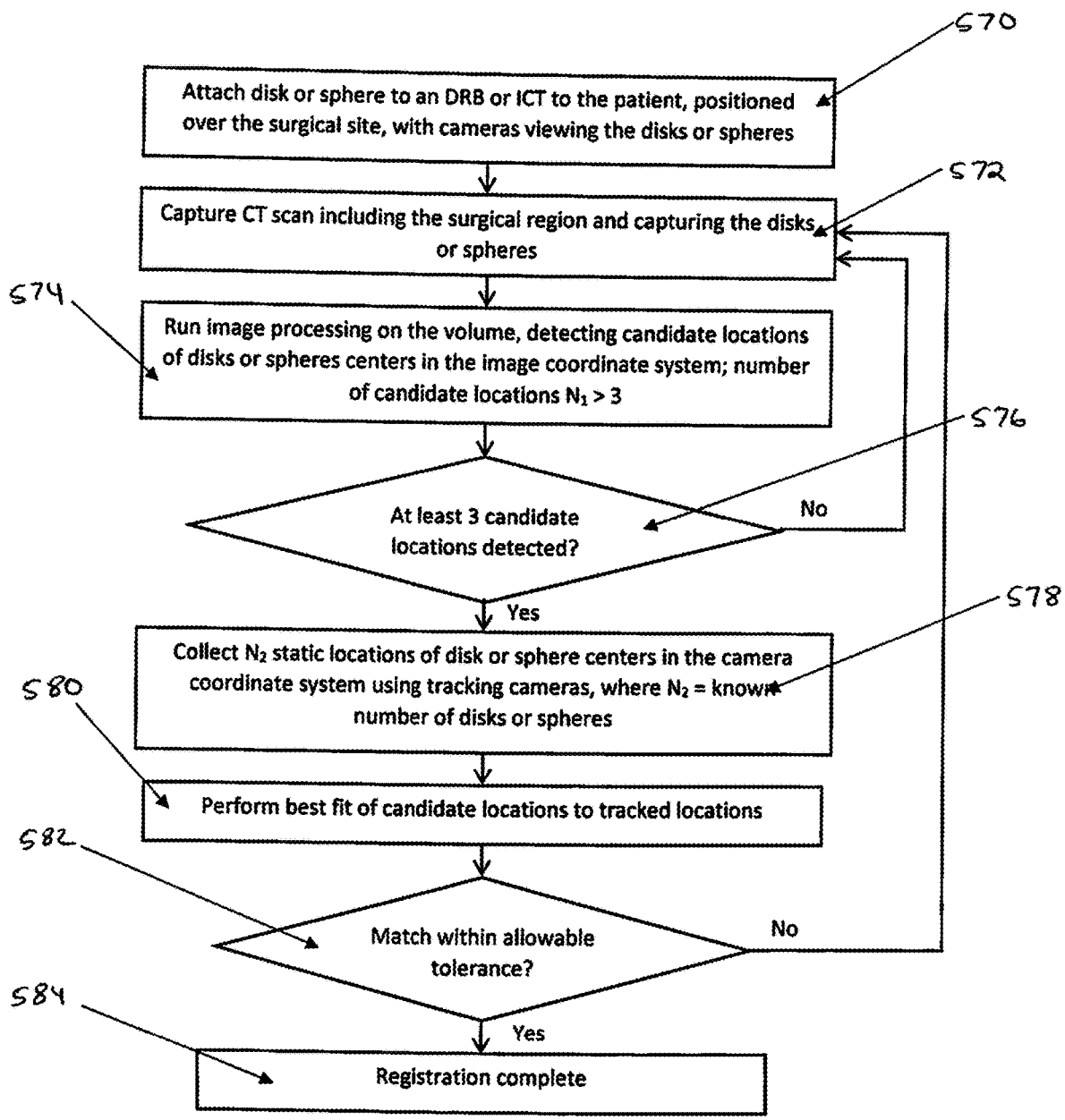
FIG. 40 is a flowchart of an algorithm for processing the location of a disk or sphere using the an optical camera system and an imaging device.

FIG. 40 is a flowchart for a registration algorithm using the disk fixture, according to the preferred embodiment. First, a plurality of discs are attached to a reference base such as a dynamic reference base or ICT 570. Next the ICT or reference base is attached to the patient, and positioned over the surgical site, with the camera system being able to see the trackable disks. Then imaging scan is initiated wherein the scan of the surgical site including the surgical region and the discs is imaged 572. Image processing on the volume, thereby detecting candidate locations of a disk face center in the image coordinate system is completed 574. If at least three candidate locations are detected, then the static locations of the disks in the camera coordinate system using the tracking cameras is applied to the registration process 576. If less the three candidate marker locations are identified, then a new imaging scan is initiated 572. Once three candidate markers locations are identified, then the static locations of the disk or sphere centers in the camera coordinate system are identified 578. Next, the candidate marker locations from the image processing and the tracking locations received from the camera system are processed 580 and the computer system determines if the match is within an allowable tolerance 582. If the match between the imaging scan location and the camera system location of the markers is within the tolerance levels, then the registration is complete. If the tolerance level is not within an allowable level, then the imaging scan is initiated once again 572. It should be noted that in other embodiments, various alternative algorithms may be utilized at different times to determine location of the disks.

Although the robot and associated systems described herein are generally described with reference to spine applications, it is also contemplated that the robot system is configured for use in other surgical applications, including but not limited to, surgeries in trauma or other orthopedic applications (such as the placement of intramedullary nails, plates, and the like), cranial, neuro, cardiothoracic, vascular, colorectal, oncological, dental, and other surgical operations and procedures.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described invention, nor the claims which follow. The entire disclosure of each patent and publication cited herein is incorporated by reference in its entirety, as if each such patent or publication were individually incorporated by reference herein. Various features and advantages of the invention are set forth in the following claims.

What is claimed is:

1. A robotic system comprising:
a base, including a computer;
a display electronically coupled to the computer;
a robot arm electronically coupled to the computer and movable based on commands processed by the computer;
an end-effector electronically coupled to the robot arm;
a dynamic reference base having at least three spaced apart posts;
tracking markers each adapted to be received in a corresponding post of the dynamic reference base;
a camera configured to detect the tracking markers,
wherein each of the tracking markers includes:
a circular disk having a circular reflective surface for passive reflection of light for optical recognition by the camera and a metallic element disposed at a center of the circular reflective surface for recognition by an imaging system;
a lower portion extending downwardly from the reflective surface and including a slot for receiving the corresponding post of the dynamic reference base; and
an annular ring frame circumferentially surrounding the circular disk and configured to provide optical contrast relative to the reflective surface of the circular disk;
wherein the computer includes an image processing application programmed to receive an optical image of the each tracking marker from the camera and to determine a center point of the circular disk which lies on a plane defined by the reflective surface based on the received optical image regardless of the orientation of the circular disk relative to the camera.

2. The system of claim 1, wherein the imaging system is a Computed Tomography imaging scanner.

3. The system of claim 1, wherein the surface of each circular disk is white and the ring frame is black.

4. The system of claim 1, wherein the tracking markers are cylindrical.

5. The system of claim 4, wherein the tracking markers are configured with a metallic outer ring frame and a reflective inner portion.

6. A robotic navigation system comprising:
a robot comprising:
a base, including a computer;
a display electronically coupled to the computer;
a robot arm electronically coupled to the computer and movable based on commands processed by the computer;
an end-effector electronically coupled to the robot arm, the end-effector including a quick-connector;
a camera configured to detect one or more tracking markers; and
a navigable instrument including an array of spaced apart posts, wherein the navigable instrument is configured to access, prepare, and/or place an implant;
wherein each of the one or more tracking markers includes:
a circular disk having a circular reflective surface for passive reflection of light for optical recognition by the camera, the circular disk being made of metal for recognition by an imaging system;
a lower portion extending downwardly from the reflective surface and including a slot for receiving a corresponding post of the navigable instrument; and
an annular ring frame circumferentially surrounding and disposed over the circular disk and configured to provide optical contrast relative to the reflective surface of the circular disk;
wherein the computer includes an image processing application programmed to receive an optical image of the each tracking marker from the camera and to determine a center point of the circular disk which lies on a plane defined by the reflective surface based on the received optical image regardless of the orientation of the circular disk relative to the camera.

7. The system of claim 6, wherein each of the one or more tracking markers is cylindrical.

8. The system of claim 6, wherein the surface of each circular disk is white and the ring frame is black.

9. The system of claim 6, wherein the imaging system is a Computed Tomography imaging scanner.

10. The system of claim 9, wherein each of the one or more tracking markers is configured with a metallic outer ring frame and a reflective inner portion.

11. A robotic system comprising:
a base, including a computer;
a display electronically coupled to the computer;
a robot arm electronically coupled to the computer and movable based on commands processed by the computer;
an end-effector electronically coupled to the robot arm, the end-effector including a quick-connector;
a dynamic reference base having at least three spaced apart posts;
tracking markers each adapted to be received in a corresponding post of the dynamic reference base;
a camera configured to detect the tracking markers,
wherein each of the tracking markers includes a housing having an upper portion and a lower portion;
wherein each of the tracking markers includes:

a circular disk having a circular reflective surface for passive reflection of light for optical recognition by the camera, the circular disk being made of metal for recognition by an imaging system; and an annular ring frame circumferentially surrounding and disposed over the circular disk and configured to provide optical contrast relative to the reflective surface of the circular disk, wherein the circular disk is part of the lower portion and the ring frame is part of the upper portion, wherein the lower portion extends downwardly from the reflective surface and includes a slot for receiving a post of an array fixture; and wherein the upper portion and the lower portion are coupled via a snap-fit connection;

wherein the computer includes an image processing application programmed to receive an optical image of the each tracking marker from the camera and to determine a center point of the circular disk which lies on a plane defined by the reflective surface based on the received optical image regardless of the orientation of the circular disk relative to the camera.

12. The system of claim 11, wherein the upper portion of the housing includes a proximal end and a distal end, the distal end of the upper portion configured with a plurality of slots.

13. The system of claim 11, wherein the lower portion includes a plurality of tabs that is configured to be received within a plurality of opening in the upper portion.

14. The system of claim 11, wherein the upper portion of the housing includes a through hole extending from a proximal portion to a distal portion of the upper portion.

15. The system of claim 14, wherein the upper portion of the housing includes a chamfered upper surface with a marking configured to be visible to a camera system.

* * * * *